(12) United States Patent
Sorrentino et al.

(10) Patent No.: US 11,529,352 B2
(45) Date of Patent: Dec. 20, 2022

(54) PRESERVATION OF IMMUNE RESPONSE DURING CHEMOTHERAPY REGIMENS

(71) Applicant: G1 Therapeutics, Inc., Research Triangle Park, NC (US)

(72) Inventors: Jessica A. Sorrentino, Durham, NC (US); Anne Y. Lai, Cary, NC (US); Jay C. Strum, Hillsborough, NC (US); Patrick Joseph Roberts, Durham, NC (US)

(73) Assignee: G1 Therapeutics, Inc., Research Triangle Park, NC (US)

( * ) Notice: Subject to any disclaimer, the term of this patent is extended or adjusted under 35 U.S.C. 154(b) by 595 days.

(21) Appl. No.: 16/432,244

(22) Filed: Jun. 5, 2019

(65) Prior Publication Data
US 2019/0321370 A1 Oct. 24, 2019

Related U.S. Application Data

(63) Continuation of application No. PCT/US2017/064775, filed on Dec. 5, 2017.
(Continued)

(51) Int. Cl.
*A61K 31/519* (2006.01)
*A61P 35/00* (2006.01)
(Continued)

(52) U.S. Cl.
CPC .......... *A61K 31/519* (2013.01); *A61K 31/365* (2013.01); *A61K 33/243* (2019.01); *A61K 38/1774* (2013.01); *A61P 35/00* (2018.01)

(58) Field of Classification Search
None
See application file for complete search history.

(56) References Cited

U.S. PATENT DOCUMENTS 8,598,186 B2  12/2013  Tavares et al.
8,598,197 B2  12/2013  Tavares et al.
(Continued)

FOREIGN PATENT DOCUMENTS

WO  WO 2005/052147 A2  6/2005
WO  WO 2007/124252 A2  11/2007
(Continued)

OTHER PUBLICATIONS

Rocha Lima et al., Cancer Research, 2016, 76(14), CT151, 107th Annual Meeting of the American Association of Cancer Research (AACR), New Orleans, LA Apr. 16-20, 2016 (Year: 2016).*
(Continued)

*Primary Examiner* — Karl J Puttlitz
(74) *Attorney, Agent, or Firm* — Knowles Intellectual Property Strategies, LLC

(57) ABSTRACT

The addition of a selective, fast-acting, short half-life CDK 4/6 inhibitor in a very specific dosage regimen to the combination of chemotherapy with a checkpoint inhibitor provides superior results in the treatment of a tumor or cancer. The unexpected discovery is that the short pulsatile specifically-timed administration of a selective, fast-acting, short half-life CDK 4/6 inhibitor during administration of the chemotherapy portion of the triple combination therapy has a profound effect on the immune cells in the cancer microenvironment.

51 Claims, 21 Drawing Sheets

Related U.S. Application Data

(60) Provisional application No. 62/479,605, filed on Mar. 31, 2017, provisional application No. 62/430,302, filed on Dec. 5, 2016.

(51) Int. Cl.
*A61K 33/243* (2019.01)
*A61K 31/365* (2006.01)
*A61K 38/17* (2006.01)

(56) References Cited

U.S. PATENT DOCUMENTS

| | | |
|---|---|---|
| 8,691,830 B2 | 4/2014 | Tavares et al. |
| 8,822,683 B2 | 9/2014 | Tavares et al. |
| 8,829,012 B2 | 9/2014 | Tavares et al. |
| 9,102,682 B2 | 8/2015 | Tavares et al. |
| 9,260,442 B2 | 2/2016 | Tavares |
| 9,464,092 B2 | 10/2016 | Strum et al. |
| 9,481,691 B2 | 11/2016 | Tavares et al. |
| 9,487,530 B2 | 11/2016 | Strum et al. |
| 9,499,564 B2 | 11/2016 | Tavares et al. |
| 9,527,857 B2 | 12/2016 | Strum et al. |
| 9,683,048 B2 | 6/2017 | Freeman et al. |
| 9,717,735 B2 | 8/2017 | Strum et al. |
| 9,745,316 B2 | 8/2017 | Tavares |
| 2011/0009353 A1 | 1/2011 | Chen-Kiang et al. |
| 2011/0224221 A1 | 9/2011 | Sharpless et al. |
| 2011/0224227 A1 | 9/2011 | Sharpless et al. |
| 2012/0100100 A1 | 4/2012 | Sharpless et al. |
| 2014/0107114 A1 | 4/2014 | Kim et al. |
| 2014/0271460 A1 | 9/2014 | Sharpless et al. |
| 2014/0271466 A1 | 9/2014 | Sharpless et al. |
| 2014/0274896 A1 | 9/2014 | Sharpless et al. |
| 2014/0275066 A1 | 9/2014 | Sharpless et al. |
| 2014/0275067 A1 | 9/2014 | Sharpless et al. |
| 2015/0031880 A1 | 1/2015 | Tavares et al. |
| 2015/0246925 A1 | 9/2015 | Tavares et al. |
| 2015/0246926 A1 | 9/2015 | Tavares et al. |
| 2015/0297606 A1 | 10/2015 | Strum et al. |
| 2015/0297607 A1 | 10/2015 | Strum et al. |
| 2015/0297608 A1 | 10/2015 | Strum et al. |
| 2015/0299212 A1 | 10/2015 | Strum et al. |
| 2016/0045509 A1 | 2/2016 | Strum et al. |
| 2016/0185870 A1 | 6/2016 | Van Eenennaam |
| 2016/0220569 A1 | 8/2016 | Strum et al. |
| 2016/0310499 A1 | 10/2016 | Strum et al. |
| 2017/0037051 A1 | 2/2017 | Strum et al. |
| 2017/0057971 A1 | 3/2017 | Tavares et al. |
| 2017/0057972 A1 | 3/2017 | Tavares |
| 2017/0065597 A1 | 3/2017 | Strum et al. |
| 2017/0100405 A1 | 4/2017 | Strum et al. |
| 2017/0119774 A1 | 5/2017 | Strum et al. |
| 2017/0182043 A1 | 6/2017 | Strum et al. |
| 2017/0209574 A1 | 7/2017 | Cao et al. |
| 2017/0246171 A1 | 8/2017 | Strum et al. |
| 2017/0296659 A1 | 10/2017 | Lebwohl et al. |

FOREIGN PATENT DOCUMENTS

| | | |
|---|---|---|
| WO | WO 2008/079933 A2 | 7/2008 |
| WO | WO 2009/061345 A2 | 5/2009 |
| WO | WO 2010/012777 A1 | 2/2010 |
| WO | WO 2010/020675 A1 | 2/2010 |
| WO | WO 2010/039997 A2 | 4/2010 |
| WO | WO 2010/051127 A2 | 5/2010 |
| WO | WO 2010/132725 A2 | 11/2010 |
| WO | WO 2012/061156 A2 | 10/2012 |
| WO | WO 2013/148748 A1 | 10/2013 |
| WO | WO 2013/163239 A1 | 10/2013 |
| WO | WO 2014/144326 A1 | 9/2014 |
| WO | WO 2014/144596 A2 | 9/2014 |
| WO | WO 2014/144740 A2 | 9/2014 |
| WO | WO 2014/144847 A2 | 9/2014 |
| WO | WO 2014/168975 A1 | 10/2014 |
| WO | WO 2015/061407 A1 | 4/2015 |
| WO | WO 2015/142675 A2 | 9/2015 |
| WO | WO 2015/161283 A1 | 10/2015 |
| WO | WO 2015/161285 A1 | 10/2015 |
| WO | WO 2015/161287 A1 | 10/2015 |
| WO | WO 2015/161288 A1 | 10/2015 |
| WO | WO 2015/176033 A1 | 11/2015 |
| WO | 2016040848 * | 3/2016 |
| WO | 2016040858 * | 3/2016 |
| WO | WO 2016/040848 A1 | 3/2016 |
| WO | WO 2016/040858 A1 | 3/2016 |
| WO | WO 2016/040892 A1 | 3/2016 |
| WO | WO 2016/100561 A2 | 6/2016 |
| WO | WO 2016/126889 A1 | 8/2016 |
| WO | WO 2017/222958 A1 | 12/2017 |
| WO | WO 2018/089518 A1 | 5/2018 |
| WO | WO 2018/091999 A1 | 5/2018 |
| WO | WO 2018/099952 A1 | 6/2018 |
| WO | WO 2018/106729 A1 | 6/2018 |
| WO | WO 2018/183479 A1 | 10/2018 |
| WO | WO 2019/108589 A1 | 6/2019 |

OTHER PUBLICATIONS

Lesterhuis et al., PLoS One, 2013, 8 (4) abstract; pp. 8 (Year: 2013).*
Testing the PD-1 Inhibitor Pembrolizumab as Maintenance Therapy After Initial Chemotherapy in Metastatic Bladder Cancer, 2015, downloaded Mar. 8, 2022 from https://clinicaltrials.gov/ct2/show/NCT02500121 (Year: 2016).*
Hamilton et al., Journal of Cancer Therapy, 2013, 4, 47-53 (Year: 2013).*
U.S. Pat. No. 8,598,186, B2, U.S. Appl. No. 13/869,520, Tavares et al., Dec. 3, 2013.
U.S. Pat. No. 8,598,197, B2, U.S. Appl. No. 13/869,576, Tavares et al., Dec. 3, 2013.
U.S. Pat. No. 8,691,830, B2, U.S. Appl. No. 13/869,594, Tavares et al., Apr. 8, 2014.
U.S. Pat. No. 8,822,683, B2, U.S. Appl. No. 14/162,637, Tavares et al., Sep. 2, 2014.
U.S. Pat. No. 8,829,012, B2, U.S. Appl. No. 14/162,649, Tavares et al., Sep. 9, 2014.
U.S. Pat. No. 9,102,682, B2, U.S. Appl. No. 14/452,296, Tavares et al., Aug. 11, 2015.
U.S. Pat. No. 9,260,442, B2, U.S. Appl. No. 14/498,796, Tavares, Jan. 27, 2016.
U.S. Pat. No. 9,464,092, B2, U.S. Appl. No. 14/212,911, Strum et al., Oct. 11, 2016.
U.S. Pat. No. 9,481,691, B2, U.S. Appl. No. 14/712,630, Tavares et al., Nov. 1, 2016.
U.S. Pat. No. 9,487,530, B2, U.S. Appl. No. 14/212,430, Strum et al., Nov. 8, 2016.
U.S. Pat. No. 9,499,564, B2, U.S. Appl. No. 14/712,582, Tavares et al., Nov. 22, 2016.
U.S. Pat. No. 9,527,857, B2, U.S. Appl. No. 14/214,048, Strum et al., Dec. 27, 2016.
U.S. Pat. No. 9,717,735, B2, U.S. Appl. No. 14/690,180, Strum et al., Aug. 1, 2017.
U.S. Pat. No. 9,745,316, B2, U.S. Appl. No. 14/982,443, Tavares, Aug. 29, 2017.
U.S. Pat. No. 9,856,268, B2, U.S. Appl. No. 15/348,862, Tavares, Jan. 2, 2018.
U.S. Pat. No. 9,931,345, B2, U.S. Appl. No. 15/288,878, Strum et al., Apr. 3, 2018.
U.S. Pat. No. 9,957,276, B2, U.S. Appl. No. 15/348,770, Tavares et al., May 1, 2018.
U.S. Pat. No. 10,076,523, B2, U.S. Appl. No. 15/387,083, Strum et al., Sep. 18, 2018.
U.S. Pat. No. 10,085,992, B2, U.S. Appl. No. 15/342,990, Strum et al., Oct. 2, 2018.
U.S. Pat. No. 10,189,849, B2, U.S. Appl. No. 15/918,834, Tavares et al., Jan. 29, 2019.
U.S. Pat. No. 10,189,850, B2, U.S. Appl. No. 15/918,852, Tavares et al., Jan. 29, 2019.

(56) References Cited

OTHER PUBLICATIONS

U.S. Pat. No. 10,189,851, B2, U.S. Appl. No. 15/918,877, Tavares et al., Jan. 29, 2019.
U.S. Pat. No. 10,231,969, B2, U.S. Appl. No. 15/457,699, Strum, et al., Mar. 19, 2019.
U.S. Pat. No. 10,376,519, B2, U.S. Appl. No. 15/665,071, Strum, et al., Aug. 13, 2019.
2018/0127431, A1, U.S. Appl. No. 15/860,483, Tavares et al., May 10, 2018.
2018/0221378, A1, U.S. Appl. No. 15/943,278, Strum, et al., Aug. 9, 2018.
2018/0360840, A1, U.S. Appl. No. 16/112,360, Strum, et al., Dec. 20, 2018.
2018/0360841, A1, U.S. Appl. No. 16/112,362, Strum, et al., Dec. 20, 2018.
2019/0030034, A1, U.S. Appl. No. 16/142,574, Strum, et al., Jan. 31, 2019.
2019/0070185, A1, U.S. Appl. No. 16/178,419, Strum, et al., Mar. 7, 2019.
2019/0119292, A1, U.S. Appl. No. 16/226,430, Tavares et al., Apr. 25, 2019.
2019/0119294, A1, U.S. Appl. No. 16/230,412, Strum, et al., Apr. 25, 2019.
2019/0125752, A1, U.S. Appl. No. 16/228,308, Strum, et al., May 2, 2019.
2019/0135784, A1, U.S. Appl. No. 16/230,388, Strum, et al., May 9, 2019.
2019/0135811, A1, U.S. Appl. No. 16/230,396, Strum, et al., May 9, 2019.
2019/0135820, A1, U.S. Appl. No. 16/230,308, Smith et al., May 9, 2019.
2019/0151311, A1, U.S. Appl. No. 16/254,364, Strum, et al., May 23, 2019.
2019/0167691, A1, U.S. Appl. No. 16/268,317, Strum, et al., Jun. 6, 2019.
Bisi et al., Preclinical Characterization of G1T28: A Novel CDK4/6 Inhibitor for Reduction of Chemotherapy-Induced Myelosuppression, Mol. Cancer Therap. (2016) (15)5: 783-793.
Bisi et al., Preclinical development of G1T38: A novel, potent and selective inhibitor of cyclin dependent kinases 4/6 for use as an oral antineoplastic in patients with CDK4/6 sensitive tumors, Oncotarget. Mar. 15, 2017: doi:10.18632/oncotarget.16216.
Bucher, N. and C. D. Britten "G2 checkpoint abrogation and checkpoint kinase-1 targeting in the treatment of cancer" Br J Cancer, Feb. 12, 2008; 98(3): 523-528.
Chou, A. et al., Tailored first-line and second-line CDK4-targeting treatment combinations in mouse models of pancreatic cancer, Gut 2017; 0:1-14. Published online Oct. 28, 2017 doi:10.1136.gutjnl-2017-315144.
Deep, G. et al. "New Combination Therapies with Cell Cycle Agents" Current Opinion in Investigational Drugs, 2008; 9: 591-605.
Deng et al., CDK4/6 Inhibition Augments Antitumor Immunity by Enhancing T-cell Activation, Cancer Discovery Feb. 2018. Published online Nov. 3, 2017; doi: 10.1158/2159-8290.CD-17-0915.
Disis, ML., Mechanism of Action of Immunotherapy, Seminars in Oncology, vol. 41 (5), Suppl. 5, pp. S3-S13, 2014; p. S8, col. 1, paragraph 4.
Goel, S. et al., CDK4/6 Inhibition Triggers Anti-Tumour Immunity; Nature. Aug. 24, 2017; 548 (7668): 471-475. doi: 10.1038/nature23465. Epub Aug. 16, 2017.
Hamilton et al., Synergistic Anticancer Activity of Topotecan—Cyclin-Dependent Kinase Inhibitor Combinations against Drug-Resistant Small Cell Lung Cancer (SCLC) Cell Lines, Journal of Cancer Therapy (2013) 4: 47-53.
Hamilton et al., Synergism of Cyclin-Dependent Kinase Inhibitors with Camptothecin Derivatives in Small Cell Lung Cancer Cell Lines, Molecules (2014), 19(2): 2077-2088.
International Search Report and Written Opinion for International Application No. PCT/US17/64775 dated Feb. 13, 2018.
International Search Report and Written Opinion for International Application No. PCT/US15/049756 dated Feb. 16, 2016.
International Search Report and Written Opinion for International Application No. PCT/US15/049777 dated Dec. 10, 2015.
Johnson, D. G. and C. L. Walker "Cyclins and Cell Cycle Checkpoints" Annual Review of Pharmacology and Toxicology, Apr. 1999; 39: 295-312.
Johnson, N. and G. Shapiro "Cyclin-dependent kinase 4/6 inhibition in cancer therapy" Cell Cycle, Nov. 1, 2012; 11(21): 3913-3918.
Matsui, K. et al., Phase II trial of carboplatin plus oral etoposide for elderly patients with small-cell lung cancer, British Journal of Cancer 77(11), pp. 1961-1965, 1998; abstract.
Menu, E. et al. "A novel therapeutic combination using PD 0332991 and bortezomib: study in the 5T33MM myeloma model" Cancer Res, Jul. 15, 2008; 68(14): 5519-5523.
Mirati Therapeutics, The Rationale and Therapeutic Promis of Combining HDAC Inhibitors with Immune Checkpoint Inhibitors, Mocetinostat + Checkpoint Inhibitors [online publication].
NCT02079636—A Study of Abemaciclib (LY2835219) in Combination With Another Anticancer Drug in Participants With Lung Cancer (NSCLC); Mar. 6, 2014.
NCT02693535—TAPUR: Testing the Use of Food and Drug Administration (FDA) Approved Drugs That Target a Specific Abnormality in a Tumor Gene in People With Advanced Stage Cancer (TAPUR); Feb. 26, 2016.
NCT02779751—A Study of Abemaciclib (LY2835219) in Participants With Non-Small Cell Lung Cancer or Breast Cancer; May 20, 2016.
NCT03294694—Ribociclib + PDR001 in Breast Cancer and Ovarian Cancer; Sep. 27, 2017.
NCT03041311—Carboplatin, Etoposide, and Atezolizumab with or without Trilaciclib; Jul. 26, 2019.
Ottensmeier, et al., A Novel Phase II Trial of Ipilimumab, Carboplatin and Etoposide (ICE) for the First Line Treatment of Extensive Stage Small Cell Lung Cancer (SCLC) Annals of Oncology 25 (Supplement 4): iv511-iv516, 2014.
Reck et al., Phase III Randomized Trial of Ipilimumab Plus Etoposide and Platinum Versus Placebo Plus Etoposide and Platinum in Extensive-Stage Small-Cell Lung Cancer. J Clin Oncol 34:3740-3748.
Roberts et al. "Multiple Roles of Cyclin-Dependent Kinase 4/6 Inhibitors in Cancer Therapy" JNCI, 2012; 104(6):476-487.
Tavares et al. "CDK Inhibitors" Unpublished U.S. Appl. No. 14/712,582, filed May 14, 2015.
Tavares et al. "CDK Inhibitors" Unpublished U.S. Appl. No. 14/712,630, filed May 14, 2015.
Zhang, et al., Cyclin D-CDK4 kinase destabilizes PD-L1 via Cul3SPOP to control cancer immune surveillance; Nature, Accelerated Article Preview; Nov. 8, 2017.
Daniel, Davey, et al.; Trilaciclib prior to chemotherapy and atezolizumab in patients with newly diagnosed extensive-stage small cell lung cancer: A multicentre, randomised, double-blind, placebo-controlled Phase II trial, Cancer Therapy and Prevention, International Journal of Cancer, 2021;148:2557-2570.
G1 Therapeutics to Evaluate Trilaciclib (G1T28) in Combination with Immune Checkpoint Inhibitor in Small-Cell Lung Cancer, Dec. 5, 2016, 2 pages.
Horn et al., A Phase III study of atezolizumab with carboplatin plus estoposide in patients with extensive-stage small cell lunch cancer (IMpower133), Annals of Oncology, vol. 27, Suppl. 6: vi493-vi496, 1 page, 2016 https.//www.sciencedirect.com/science/article/pii/S0923753419450497?via%3Dihub.
Sorrentio, Jessica et al., "Trilaciclib (G1T28), a CDK4/6 Inhibitor, Enhances the Efficacy of Combination Chemotherapy and Immune Checkpoint Inhibitor Treatment in Preclinical Models," Abstract #5628, AACR Annual Meeting, Apr. 1-5, 2017, Washington DC (2017), 2 pages.
Tan, Antoinette R. et al., "Trilaciclib plus chemotherapy versus chemotherapy alone in patients with metastatic triple-negative breast cancer: a multicentre, randomised, open-label, phase 2 trial," Lancet Oncol 2019; 20: 1587-601.
Weiss, J.M., et al., "Myelopreservation with the CDK4/6 inhibitor Trilaciclib in patients with small-cell lung cancer receiving first-line

(56) References Cited

OTHER PUBLICATIONS chemotherapy: a phase Ib/randomized phase II trial," ESMO Annals of Oncology 30: 1613-1621, 2019.

Lima Caio Max S Rocha et al., "G1T28, a cyclin dependent kinase 4/6 inhibitor, in combination with etoposide and carboplatin for extensive stage small cell lung cancer (ES-SCLC): preliminary results", Cancer Research, 2016, 76(14), CT151, XP002799585; & 107th Annual Meeting of the American Association of Cancer Research (AACR), New Orleans, LA Apr. 16-20, 2016.

Sorrentino Jessica et al., "G1T28-1, a novel CDK 4/6 inhibitor, protects murine hematopoietic stem and progenitor cells from cytotoxic chemotherapy", Cancer Research, 2015, 75(15), 941, XP002799586; & 106th Annual Meeting of the American Association for Cancer Research (AACR), Philadelphia, PA, Apr. 18-22, 2015.

Sorrentino Jessica et al., "Trilaciclib (G1T28), a CDK 4/6 inhibitor, enhances the efficacy of combination therapy and immune checkpoint inhibitor treatment in preclinical models", Cancer Research, 2017, 77(13), Supplement 1, XP002799587.

Tao Z et al., "Coadministration of trametinib and palbociclib radiosensitizers KRAS-Mutant non-small cell lung cancers in vitro and in vivo", Cancer Therapy, 2016, 22(1), 122-133.

He et al., "Transient CDK4/6 inhibition protects hematopoietic stem cells from chemotherapy-induced exhaustion", Science Translational Medicine, 2017, 9, eaal3986.

U.S. Pat. No. 10,413,547, B2, U.S. Appl. No. 16/142,574, Strum, et al., Sep. 17, 2019.

U.S. Pat. No. 10,434,104, B2, U.S. Appl. No. 16/112,362, Strum, et al., Oct. 8, 2019.

U.S. Pat. No. 10,464,940, B2, U.S. Appl. No. 15/860,483, Tavares et al., Nov. 5, 2019.

U.S. Pat. No. 10,618,905, B2, U.S. Appl. No. 16/230,412, Strum, et al., Apr. 14, 2020.

U.S. Pat. No. 10,654,831, B2, U.S. Appl. No. 16/230,388, Strum, et al., May 19, 2020.

U.S. Pat. No. 10,660,896, B2, U.S. Appl. No. 15/943,278, Strum, et al., May 26, 2020.

U.S. Pat. No. 10,696,682, B2, U.S. Appl. No. 16/226,430, Tavares et al., Jun. 30, 2020.

U.S. Pat. No. 10,709,711, B2, U.S. Appl. No. 16/228,308, Strum, et al., Jul. 14, 2020.

U.S. Pat. No. 10,829,490, B2, U.S. Appl. No. 16/230,396, Strum, et al., Nov. 10, 2020.

2019/0321332, A1, U.S. Appl. No. 16/460,502, Strum et al., Oct. 24, 2019.

2019/0374545, A1, U.S. Appl. No. 16/547,342, Sorrentino, et al., Dec. 12, 2019.

2020/0022983, A1, U.S. Appl. No. 16/572,418, Strum, et al., Jan. 23, 2020.

2020/0123168, A1, U.S. Appl. No. 16/721,631, Smith et al., Apr. 23, 2020.

2020/0216406, A1, U.S. Appl. No. 16/824,290, Strum, et al., Jul. 9, 2020.

2020/0239486, A1, U.S. Appl. No. 16/847,426, Strum, et al., Jul. 30, 2020.

2020/0277300, A1, U.S. Appl. No. 15/931,330, Tavares et al., Sep. 3, 2020.

2020/0283406, A1, U.S. Appl. No. 16/877,249, Strum, et al., Sep. 10, 2020.

2020/0331925, A1, U.S. Appl. No. 16/918,985, Strum, et al., Oct. 22, 2020.

2020/0345742, A1, U.S. Appl. No. 16/886,309, Strum, et al., Nov. 5, 2020.

2020/0345743, A1, U.S. Appl. No. 16/926,035, Strum, et al., Nov. 5, 2020.

U.S. Appl. No. 16/924,033, Beelen et al., filed Jul. 8, 2020.

U.S. Appl. No. 17/067,549, Strum, et al., filed Oct. 9, 2020.

U.S. Appl. No. 17/088,298, Strum, et al., filed Nov. 3, 2020.

U.S. Appl. No. 17/153,516, Tavares et al., filed Jan. 20, 2021.

U.S. Appl. No. 17/181,638, Strum et al., filed Feb. 22, 2021.

U.S. Appl. No. 17/403,577, Strum et al., filed Aug. 16, 2021.

U.S. Appl. No. 17/554,940, Roberts et al., filed Dec. 17, 2021.

2021/0047328, A1, U.S. Appl. No. 17/088,298, Strum et al., Feb. 18, 2021.

2021/0077498, A1, U.S. Appl. No. 17/102,311, Strum et al., Mar. 18, 2021.

2021/0122755, A1, U.S. Appl. No. 17/121,392, Smith et al., Apr. 29, 2021.

2021/0179567, A1, U.S. Appl. No. 17/184,354, Schneider et. al., Jun. 17, 2021.

U.S. Appl. No. 17/222,873, Strum et al., filed Apr. 5, 2021.

U.S. Appl. No. 17/236,687, Schneider et. al., filed May 7, 2021.

U.S. Appl. No. 17/315,011, Sorrentino et al., filed May 7, 2021.

Stice, James P. et al., "CDK4/6 Therapeutic Intervention and viable alternative to taxane in CRPC", Molecular Cancer Research, 2017, 15(6), 660-669, XP55457140.

Lesterhuis WJ et al. Synergistic Effect of CTLA-4 Blockade and Cancer Chemotherapy in the Induction of Anti-Tumor Immunity. PLoS One, 2013, 8 (4): e61895, abstract); pp. 8.

Schaer, et al.; "The CDK4/6 Inhibitor Abemaciclib Induces a T Cell Inflamed Tumor Microenvironment and Enhances the Efficacy of PD-L1 Checkpoint Blockade"; Cell Reports 22, 2978-2994, Mar. 13, 2018.

Daniel, D et al., "Trilaciclib prior to chemotherapy and atezolizumab in patients with newly diagnosed extensive-stage small cell lung cancer: A multicentre, randomised, double-blind, placebo-controlled Phase II trial", Int J Cancer, 2021, 148(10), 2557-70.

Deng, J et al., "CDK4/6 Inhibition Augments Antitumor Immunity by Enhancing T-cell Activation", Cancer Discov., 2018, 8(2), 217-33.

Lai, Ay et al., "CDK4/6 inhibition enhances antitumor efficacy of chemotherapy and immune checkpoint inhibitor combinations in preclinical models and enhances T-cell activation in patients with SCLC receiving chemotherapy". Journal for ImmunoTherapy of Cancer, 2020, 8(2), e000847.

Zhang, J et al., "Cyclin D-CDK4 kinase destabilizes PD-L1 via Cul3SPOP to control cancer immune surveillance", Nature, 2018, 553(7686), 91-5.

2020/0405721, A1, U.S. Appl. No. 16/924,033, Beelen et al., Dec. 31, 2020.

2021/0030758, A1, U.S. Appl. No. 17/067,549, Strum et al., Feb. 4, 2021.

2021/0395259, A1, U.S. Appl. No. 17/153,516, Tavares et al., Dec. 23, 2021.

2021/0213022, A1, U.S. Appl. No. 17/181,638, Strum et al., Jul. 15, 2021.

2021/0299130, A1, U.S. Appl. No. 17/222,873, Strum et al., Sep. 30, 2021.

2022/0175780, A1, U.S. Appl. No. 17/403,577, Strum et al., Jun. 9, 2022.

2022/0175787, A1, U.S. Appl. No. 17/554,940, Roberts et al., Jun. 9, 2022.

U.S. Appl. No. 17/234,686, Strum et al., filed Apr. 19, 2021.

U.S. Appl. No. 17/718,052, Strum et al., filed Apr. 11, 2022.

U.S. Appl. No. 17/839,215, Beelen et al., filed Jun. 13, 2022.

\* cited by examiner

PRESERVATION OF IMMUNE RESPONSE DURING CHEMOTHERAPY REGIMENS

STATEMENT OF RELATED APPLICATIONS

This application is a continuation of International Patent Application No. PCT/US2017/064775, filed Dec. 5, 2017, which claims benefit of U.S. Provisional Application No. 62/430,302, filed Dec. 5, 2016, and U.S. Provisional Application No. 62/479,605, filed Mar. 31, 2017. These applications are hereby incorporated by reference for all purposes.

FIELD OF THE INVENTION

This invention is in the area of improvements in anti-cancer and anti-tumor treatment regimens that alter the tumor microenvironment in a manner that promotes a pro-inflammatory microenvironment.

BACKGROUND

Cancer immunotherapy uses the host's innate immune system to fight the cancer or tumor by stimulating the immune system to work harder and smarter. An important part of the immune system is the ability to distinguish normal from foreign cells. To do this, the immune system uses "checkpoints" which are molecule on certain cells that have to be activated (or inactivated) to start the response. Cancer and tumors can find ways to use these checkpoints to avoid attack by the immune system. Examples of "off-switches" are the proteins PD-1, PDL-1 and CTLA-4. Recent advances in cancer treatment include the administration of antibodies to one of these checkpoint "off-switches" to deactivate the off-switch and allow the host's immune system to increase its ability to attack the diseased cell.

Several immune checkpoint inhibitors have been approved by the Food and Drug Administration (FDA). The first such drug to receive approval, ipilimumab (Yervoy®, Bristol-Myers Squibb), for the treatment of advanced melanoma, blocks the activity of cytotoxic T-lymphocyte-associated protein 4 (CTLA-4), a checkpoint protein which is expressed on the surface of activated immune cells called cytotoxic T lymphocytes. CTLA-4 acts as a "switch" to inactivate these T cells, thereby reducing the strength of immune responses; ipilimumab binds to CTLA-4 and prevents it from sending its inhibitory signal.

Two other FDA-approved checkpoint inhibitors, nivolumab (Opdivo®, Bristol-Myers Squibb) and pembrolizumab (Keytruda®, Merck), work in a similar way, but target a different checkpoint protein on activated T cells, programmed cell death protein 1 (PD-1). Nivolumab is approved to treat some patients with advanced melanoma or advanced lung cancer, and pembrolizumab is approved to treat some patients with advanced melanoma. Additional inhibitors targeted to PD-1 currently in development include pidulizumab (Medivation), MGA012 (MacroGenics), and BGB-A317 (BeiGene). PD-1 inhibitors have also been described by Novartis AG in U.S. Pat. Nos. 9,683,048, and 9,683,048. Checkpoint inhibitors that disrupt the interaction of PD-1 with its ligand on the surface of cancer cells known as PD-L1 and PD-L2, which downregulate the activity of PD-1, have also been developed, namely durvalumab (Imfinzi®, Astrazeneca), avelumab (Bavencio®, Pfizer) and atezolizumab (Tecentriq®, Genentech/Roche)). Additional inhibitors targeted to PD-L1 currently in development include Ca-170 (Curis) and LY3300054 (Eli Lilly). PD-L1 inhibitors have also been described by Novartis AG in US 2017/0296659 and WO 2016/040892.

While some immune checkpoint inhibitors have been shown to be efficacious and lead to durable responses in patients with various cancers, only a minority of patients respond. Furthermore, a number of checkpoint immune inhibitors, for example the anti-PD-L1 compound BMS-936559, have not been further developed due to poor response rates. An approach to increase the response rate of immune checkpoint inhibitors is to combine them with chemotherapy in order to enhance immunogenic cell death and "prime" the immune system. However, chemotherapy itself can cause damage to various cell types of the immune system, including hematopoietic stem and progenitor cells (HSPCs) and immune effector cells such as T-lymphocytes, diminishing the efficacy of the chemotherapy/checkpoint inhibitor combination.

It is an object of the present invention to provide a therapeutic approach to treat a host with a cancer or tumor that increases the preservation of the host's innate immune system during and/or after chemotherapy in a manner that enhances the body's ability to use its own immune machinery to destroy the diseased cells on a short-term and/or long-term basis.

SUMMARY OF THE INVENTION

It has been surprisingly and unexpectedly discovered that the addition of a selective, fast acting, short half-life CDK 4/6 inhibitor in a very specific dosage regimen to the combination of chemotherapy with a checkpoint inhibitor provides superior results in the treatment of a tumor or cancer. The unexpected discovery is that the specifically-timed administration of the CDK 4/6 inhibitor prior to each administration of the chemotherapy portion of the triple combination therapy has a profound effect on the immune cells in the cancer microenvironment. The result is remarkable in that the administration of the CDK 4/6 inhibitor as described herein provides one or more of: (i) protection of immune tumor cell infiltrates from damage, (ii) an increased durability of the immune response via a higher frequency of tumor-specific memory T-cells, (iii) a greater decrease in immune suppressor intra-tumor Treg cells; and/or (iv) a change in the gene expression of pro-inflammatory agents. The expression of genes functionally enriched for lymphocyte activation and upregulation of the pro-inflammatory cytokine interferon-γ is significantly enhanced. In parallel, several genes involved in immunosuppressive reactive oxygen species metabolic processes are down-regulated. These findings indicate that the timing of the administration of the CDK 4/6 inhibitor leads to modulation of gene expression, resulting in a pro-inflammatory tumor microenvironment that is favorable for decreasing the deleterious effects of chemotherapy while increasing the efficacy of the checkpoint inhibitor activity. This improvement provides a significant advance in the state of the art of cancer treatment.

The net result of this effect on the microenvironment of the tumor is an improvement in the ability of the host's innate immune response to effectively combat the cancer or tumor, increasing the ability to achieve short term (up to approximately 1, 2, 3, 4, 5, or 6 months), long term (up to 7, 8, 9, 10, 11 or 12 months or greater) or complete responses.

In contrast, it has been discovered that the profound benefits of this specific dosage regime in the triple combination therapy of a chemotherapeutic agent, a checkpoint inhibitor and a CDK 4/6 inhibitor are not achieved when the CDK 4/6 inhibitor is administered in a continuous or substantially continuous fashion resulting in continuous CDK4/6 inhibition of immune effector cells, wherein the immune effector cells of the tumor microenvironment remain suppressed for a sufficient time such that they have a markedly decreased ability to destroy the diseased cells.

Specific benefits of this therapy include one or more of:

Short-term intra-tumor immune cell types (CD4+T, CD8+ T, Tregs, NK, and MDSC subsets) are highly proliferative and sensitive to CDK4/6 inhibition, allowing transient cell-cycle arrest by the CDK 4/6 inhibitor which protect immune infiltrates from damage by chemotherapy similarly to hematopoietic progenitors in the bone marrow. With specifically-timed administration according to the invention, proliferation of one or more of these cell types, for example, can be maximally inhibited by up to about 50, 60, 70, 75 or 80% or more in approximately 6 to 24 hours, and recover in approximately equal to or less than about 30, 40, 45, 48, 50 or 60 hours.

Preservation of intra-tumor immune cells by the specifically-timed administration of the CDK 4/6 inhibitor when added to chemotherapy/checkpoint inhibitor combinations leads to increased durability of treatment response. A higher frequency of tumor-specific memory T cells can be observed. In some examples, the median frequency on day 50 post-treatment may be at least approximately 1.2, 1.4, 1.6, 1.8, 2.0, 2.2, 2.4, or 2.6 or more-fold higher in specifically-timed CDK 4/6 inhibitor/chemotherapy/checkpoint inhibitor regimen than in the chemotherapy/checkpoint inhibitor regimen alone. The longer durability of memory T-cells provides longer term protection to the host against the diseased cells.

Addition of specifically-timed administration of the CDK 4/6 inhibitor to chemotherapy/checkpoint inhibitor combination regimen leads to a greater decrease in intra-tumor Treg population. In certain embodiments, the proportion of intra-tumor Tregs in CD4+ T cell population using this improved regimen can be up to about 10, 20, 25, 30, 35, 40 or 50% lower compared to chemotherapy/checkpoint inhibitor therapy alone, after at least 7, 8, 9, 10 or 15 days or more after treatment. In certain embodiments, the kinetics of inhibition in Treg proliferation is delayed compared to CD8+ T cells, indicating that CD8+ T cells are better protected.

In one non-limiting embodiment, the specifically-timed administration of a CDK 4/6 inhibitor includes the selective, fast-acting, short half-life CDK 4/6 inhibitor Compound I (see below), a chemotherapeutic agent cytotoxic to immune effector cells, for example oxaliplatin, and an antibody to PD1, PD-L1 or CTLA4. In another embodiment, the specifically-timed administration of a CDK 4/6 inhibitor includes Compound I, carboplatin and an antibody to PD1, PD-L1 or CTLA4. In one aspect of this invention, the cancer is small cell lung carcinoma (SCLC). In yet another embodiment, the specifically-timed administration of a CDK 4/6 inhibitor includes Compound I, etoposide and an antibody to PD1, PD-L1 or CTLA4. In one aspect of these embodiments, the cancer is small cell lung carcinoma. In another aspect, carboplatin and etoposide are used in combination.

A summary of embodiments of the invention is described in further detail below.

In aspects, the present invention provides methods for treating a cancer or tumor in a subject by enhancing the pro-inflammatory microenvironment through the use of a regimented treatment protocol comprising the specifically-timed administration of a CDK4/6 inhibitor, for example a selective, fast-acting, short half-life CDK4/6 inhibitor, in combination with a chemotherapeutic agent, for example a chemotherapeutic agent that is cytotoxic to immune effector cells, and an immune checkpoint inhibitor. It has been found that by using a CDK4/6 inhibitor during a chemotherapeutic agent/immune checkpoint inhibitor combination therapy regimen, immune effector cells such as T lymphocytes are protected from chemotherapeutic agent toxicity and released from a transient cell-cycle arrest in the presence of chemotherapy-induced immunogenic cell death, in a manner that provides for significantly improved priming and activation of an anti-cancer immune response and anti-cancer effect than without the use of a CDK4/6 inhibitor. It has also been found that by using a CDK4/6 inhibitor during a chemotherapeutic agent/immune checkpoint inhibitor therapy regimen, anti-tumor activity is enhanced by cell cycle independent and dependent mechanisms, including the selective reduction of intra-tumoral Treg populations, preservation of pro-inflammatory immune effector cells such as tumor infiltrating lymphocytes, and an increased durability in treatment response. The controlled inhibition of CDK4/6 with a CDK4/6 inhibitor, for example a selective, short half-life CDK4/6 inhibitor, in combination with a chemotherapeutic agent and immune checkpoint inhibitor as described herein, provides a significant increase in anti-tumor effects compared to the administration of a chemotherapeutic agent and immune checkpoint inhibitor alone, or the continuous inhibition of CDK4/6 with a CDK4/6 inhibitor dosed daily, including longer acting CDK4/6 inhibitors, in combination with an immune checkpoint inhibitor.

Many chemotherapeutic agents, for example, but not limited to, protein synthesis inhibiting or DNA-damaging chemotherapeutic agents, tend to be non-specific and toxic to normal, rapidly dividing cells, including immune effector cells, and hematological toxicities such as myelosuppression are a common side effect of chemotherapeutic treatment. Immune effector cells generally require the activity of CDK4/6 for proliferation, i.e., they are CDK4/6-replication dependent (see Roberts et al. Multiple Roles of Cyclin-Dependent Kinase 4/6 Inhibitors in Cancer Therapy. JNCI 2012; 104(6):476-487). All major intra-tumor immune cell types, for example CD4+ T-cells, CD8+ T-cells, natural killer (NK) cells, and myeloid derived suppressor cells (MDSCs), are sensitive to CDK4/6 inhibition. By using a selective, fast-acting, short half-life CDK4/6 inhibitor during chemotherapy treatment, immune effector cells, which are sensitive to the damaging effects of chemotherapeutic agents during proliferation, are transiently arrested in the G0/G1 phase of the cell cycle. By protecting these cells from the damaging effects of chemotherapeutic agents, the use of specifically-timed administration of a CDK4/6 inhibitor preserves immune function, enhances T-cell activation, and increases the efficacy of immune checkpoint inhibitors, significantly improving the anti-cancer immune response.

In non-limiting illustrative embodiments, Example 5 and 9, FIGS. 10, 11, 19, 20 confirm that specifically-timed dosing of a CDK4/6 inhibitor in combination with a chemotherapeutic agent and an immune checkpoint inhibitor, selectively protects pro-inflammatory intra-tumoral immune cell infiltrates while selectively decreasing the intra-tumoral population of anti-inflammatory infiltrates such as CD4+/CD25+ Treg cells. This indicates that controlled inhibition of the CDK4/6 pathway leads to a loss of suppressive function in Treg cells and alters their ability to inhibit T-cell proliferation. Again, as an illustrative embodiment, Example 5, FIG. 11 shows that the proportion of intra-tumoral Treg cells was 40% lower in animals receiving a specifically-timed CDK4/6 inhibitor/chemotherapeutic agent/immune checkpoint inhibitor combination compared to animals receiving a chemotherapeutic agent and immune checkpoint inhibitor without specifically-timed dosing with a CDK4/6 inhibitor. Accordingly, incorporating the specifically-timed dosing with a selective, fast-acting, short half-life CDK4/6 inhibitor as described herein provides for a targeted approach of eliminating undesirable Treg cells and increasing pro-inflammatory immune effector cell infiltrates.

While specifically-timed administration of a CDK4/6 inhibitor leads to an initial significant reduction in immune cell proliferation (see Example 10 where the reduction is more than 75%), and proliferation of the beneficial T cells in animal models are fully restored typically by at least 1.5, 2, 2.5 or 3 days later. Furthermore, the overall expression of genes associated with lymphocyte activation and upregulation of the pro-inflammatory cytokine interferon γ is significantly enhanced (see non-limiting illustrative Examples 12 and 13, FIGS. 25-31). Comparatively, genes associated with immunosuppressive oxygen species metabolic processes are down-regulated, indicating that transient cell-cycle arrest in tumor immune infiltrates can lead to modulation of gene expression, resulting in a pro-inflammatory tumor microenvironment that is favorable for increasing immune checkpoint inhibitor activity (see non-limiting illustrative Example 14, FIGS. 32 to 37).

Importantly, the specifically-timed dosing with a selective, fast-acting, short half-life CDK4/6 inhibitor in combination with a chemotherapeutic agent and immune checkpoint inhibitor leads to increased durability of treatment response. A non-limiting illustrative example is provided in Example 11, FIGS. 23 and 24, which confirms a higher frequency of tumor-specific memory T-cells is observed in tumor models when a CDK4/6 inhibitor is added to a chemotherapeutic agent/immune checkpoint inhibitor combination therapy, in this illustrative example, resulting in a two-fold increase in the population of tumor specific memory T cells compared to the chemotherapeutic agent/immune checkpoint inhibitor combination treatment without a CDK4/6 inhibitor. In addition, tumor progression delay is significantly improved using specifically-timed dosing of a selective, fast-acting, short half-life CDK4/6 inhibitor in combination with a chemotherapeutic agent and immune checkpoint inhibitor compared to treatment of a chemotherapeutic agent and an immune checkpoint inhibitor without a CDK4/6 inhibitor or the continuous inhibition of CDK4/6 with a CDK4/6 inhibitor dosed daily in combination with an immune checkpoint inhibitor. (See Example 7 and 16, FIGS. 14, 15, and 38).

Accordingly, in one aspect of the invention, the invention provides an improved method of treating a host, for example a human, with cancer or a tumor that includes providing to the subject a specifically-timed administration of a selective CDK4/6 inhibitor in combination with a treatment regime of a chemotherapeutic agent, and an immune checkpoint inhibitor. In one embodiment, the dosing of the selective CDK4/6 inhibitor is specifically-timed prior to or at the time of chemotherapeutic agent administration. In one embodiment, the CDK4/6 inhibitor is only administered prior to or at the time of chemotherapeutic agent administration. In one embodiment, the treatment includes a multi-day treatment cycle comprising an induction phase and a maintenance phase, wherein the induction phase includes the specifically-timed administration of a selective CDK4/6 inhibitor, chemotherapy agent, and a checkpoint inhibitor, wherein the selective CDK4/6 inhibitor is only administered concomitantly or prior to, for example less than about 8 hours, less than about 7 hours, less than about 6, hours, less than about 5 hours, less than about 4 hours, less than about 3 hours, less than about 2 hours, less than about 1 hour, or about 30 minutes, administration of the chemotherapy agent; wherein the maintenance phase includes the administration of the checkpoint inhibitor alone, and wherein the maintenance phase occurs subsequent to one or more induction phases. In one embodiment, the maintenance phase includes the administration of an immune checkpoint inhibitor one or more times. In one embodiment, the CDK4/6 inhibitor is a selective, fast-acting, short half-life inhibitor, which provides transient protection of immune effector cells, allowing for the rapid re-entry of the immune effector cells into the cell cycle allowing for activation and proliferation following the dissolution of the chemotherapeutic effect during the induction phase. In one embodiment, the chemotherapeutic agent is an agent that is cytotoxic or cytostatic to immune effector cells, for example but not limited to, a protein synthesis inhibitor, a DNA-damaging chemotherapeutic, an alkylating agent, a topoisomerase inhibitor, an RNA synthesis inhibitor, a DNA complex binder, a thiolate alkylating agent, a guanine alkylating agent, a tubulin binder, DNA polymerase inhibitor, an anticancer enzyme, RAC1 inhibitor, thymidylate synthase inhibitor, oxazophosphorine compound, integrin inhibitor such as cilengitide, camptothecin or homocamptothecin, antifolate or a folate antimetabolite, or combination thereof.

In another aspect of the invention, the invention provides a method of increasing a pro-inflammatory immune effector cell population in an intra-tumoral immune cell infiltrate population in a subject with cancer or a tumor comprising the specifically-timed administration to the subject, such as a human, of an effective amount of a selective CDK4/6 inhibitor in the course of treatment with a chemotherapeutic agent, and an immune checkpoint inhibitor as described herein. In one embodiment, the pro-inflammatory immune effector cell population is increased by up to 10%, 20%, 30%, 40%, 50% or more compared to the pro-inflammatory immune effector cell population in an intra-tumoral immune cell infiltrate population without the specifically-timed administration of a selective CDK4/6 inhibitor. In one embodiment, the selective CDK4/6 inhibitor is a fast-acting, short half-life CDK4/6 inhibitor.

In another aspect of the invention, the invention provides a method of increasing T-cell activation in an intra-tumoral immune cell infiltrate population in a subject with cancer or a tumor comprising administering to the subject an effective amount of a selective CDK4/6 inhibitor, a chemotherapeutic agent, and an immune checkpoint inhibitor as described herein. In one embodiment, the activated T-cell is a CD4+ T-cell. In one embodiment, the activated T-cell is a CD8+ T-cell. In one embodiment, the activated T-cells produce interferon γ. In one embodiment, the percent of activated T cells in an intra-tumoral immune cell infiltrate population is about 5%, 10%, 15%, 20%, or more. In one embodiment, the production of interferon γ is increased due to upregulation of the INFG gene. In one embodiment, the production of interferon γ is increased due to upregulation of the IL2 gene. In one embodiment, the production of interferon γ is increased due to upregulation of the IL18 gene. In one embodiment, the production of interferon γ is increased due to upregulation of the LTA gene. In one embodiment, the selective CDK4/6 inhibitor is a fast-acting, short half-life CDK4/6 inhibitor.

In one aspect of the present invention, provided herein is a method of reducing the population of regulatory T-cells (Tregs) in an intra-tumoral immune cell infiltrate population in a subject suffering from cancer comprising administering to the subject an effective amount of a CDK4/6 inhibitor, a chemotherapeutic agent, and an immune checkpoint inhibitor as described herein. In one embodiment, the Treg is a CD4+CD25+ Treg. In one embodiment, the population of regulatory T cells in an intratumoral cell infiltrate population is decreased by about 10%, 20%, 30%, 40% or more compared to an intra-tumoral cell infiltrate population from a subject not receiving a CDK4/6 inhibitor, a chemotherapeutic agent, and an immune checkpoint inhibitor in a therapeutic regimen as described herein. In one embodiment, the selective CDK4/6 inhibitor is a fast-acting, short half-life CDK4/6 inhibitor.

In one aspect of the present invention, the invention provides a method of inhibiting the immune-suppressive function of regulatory T-cells in an intra-tumoral immune cell infiltrate population in a subject with cancer or a tumor comprising administering to the subject an effective amount of a selective CDK4/6 inhibitor, a chemotherapeutic agent, and an immune checkpoint inhibitor as described herein. In one embodiment, the Treg is a CD4+CD25+ Treg. In one embodiment, the decreased immune-suppressive function of regulatory T cells is measured by a decrease in Phospho-Rb. In one embodiment, the levels of Phospho-Rb in a regulatory T cell are decreased by at least approximately 5%, 10%, 15%, 20% or more compared to untreated regulatory T cells. In one embodiment, the decreased immune-suppressive function of regulatory T cells leads to increased proliferation of CD8+ T cells by, for example, at least 10%, 20%, 30%, 40%, 50% or more compared to an intra-tumoral cell infiltrate population from a subject not receiving a specifically-timed, selective CDK4/6 inhibitor, a chemotherapeutic agent, and an immune checkpoint inhibitor in a therapeutic regimen as described herein. In one embodiment, the selective CDK4/6 inhibitor is a fast-acting, short half-life CDK4/6 inhibitor.

In one aspect of the present invention, the invention provides a method of enhancing the generation of tumor-specific memory T-cells in a subject with cancer or a tumor comprising administering to the subject an effective amount of a specifically-timed, selective CDK4/6 inhibitor, a chemotherapeutic agent, and an immune checkpoint inhibitor as described herein. In one embodiment, the percentage of tumor-specific memory T cells found in the spleen of the subject is increased by at least approximately 0.25%, 0.5%, 0.75%, 1% or more out of the total T cell population. In one embodiment, the percentage of tumor-specific memory T cells found in the blood of the subject is increased by at least approximately 0.5%, 1%, 1.5% or more out of the total T cell population. In one embodiment, the selective CDK4/6 inhibitor is a fast-acting, short half-life CDK4/6 inhibitor.

In one aspect of the present invention, the invention provides a method of protecting intra-tumor immune cells from chemotherapy in a subject with cancer or a tumor comprising administering to the subject an effective amount of a specifically-timed, selective CDK4/6 inhibitor, a chemotherapeutic agent, and an immune checkpoint inhibitor as described herein. The protection of intra-tumor immune cells from the toxicity of chemotherapy leads to an enhanced anti-tumor immune response. In one embodiment, the protected intra-tumor immune cells are selected from CD8+ T cells, CD4+ T cells, natural killer (NK) cells, monocytic myeloid derived suppressor cells (mMDSCs), and granulocytic myeloid derived suppressor cells (gMDSCs). In one embodiment, the percent proliferation of the intra-tumor immune cells is at least approximately 5%, 10%, 15%, 20%, 25%, or 30% higher than the proliferation of immune cells found in the spleen. In one embodiment, the selective CDK4/6 inhibitor is a fast-acting, short half-life CDK4/6 inhibitor.

The CDK4/6 inhibitor used in this treatment regimen can be any selective CDK4/6 inhibitor that achieves the desired purpose, for example, but not limited to trilaciclib (G1 Therapeutics, Inc.), ribociclib (Novartis), palbociclib (Pfizer), or abemaciclib (Eli Lily). In one embodiment, the CDK4/6 inhibitor is a selective, fast-acting, short half-life, transient CDK4/6 inhibitor, for example selected from Compound I (trilaciclib), II, III, or IV, as described herein, or a pharmaceutically acceptable composition, salt, isotopic analog, or prodrug thereof:

I

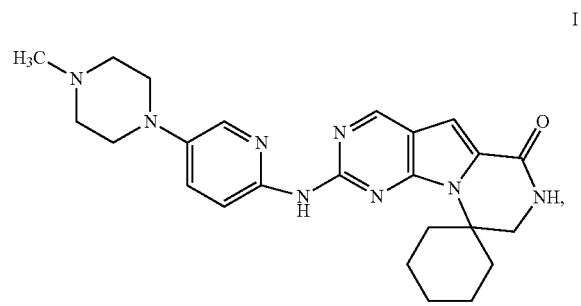

II

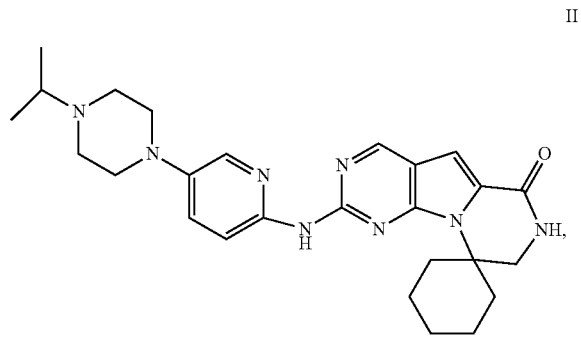

III

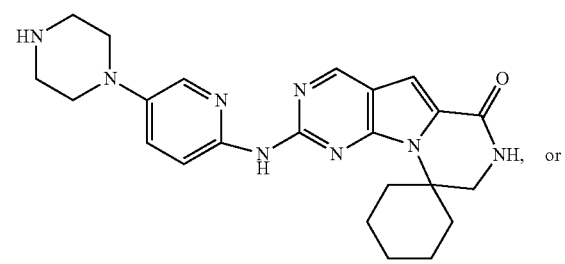

IV

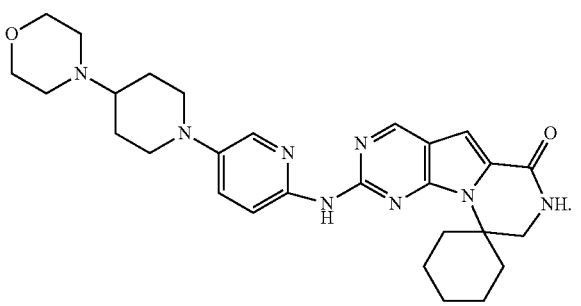

In one embodiment, the selective, fast-acting, short half-life CDK4/6 inhibitor is Compound I (trilaciclib), or a pharmaceutically acceptable composition, salt, isotopic analog, or prodrug thereof.

As provided herein, the selective CDK4/6 inhibitor is administered in a specifically-timed therapeutic regimen that includes a chemotherapeutic agent and an immune checkpoint inhibitor. The chemotherapeutic agent can be any chemotherapeutic agent effective or useful to treat a cancer, tumors, or abnormal cellular proliferation. In one embodiment, the selective CDK4/6 inhibitor is administered prior to or concomitantly with the administration of the chemotherapeutic agent so that immune effector cells are arrested during the chemotherapeutic agent's therapeutic window, reducing or eliminating the toxic effects of the chemotherapeutic on the immune effector cells. In one embodiment, the selective CDK4/6 inhibitor is administered to the subject less than about 24 hours, about 20 hours, about 16 hours, about 12 hours, about 8 hours, about 4 hours, about 2.5 hours, about 2 hours, about 1 hour, about ½ hour or less prior to treatment with the chemotherapeutic agent. In a particular embodiment, the selective CDK4/6 inhibitor is administered about ½ hour prior to administration of the chemotherapeutic agent. Typically, the selective CDK4/6 inhibitor is administered to the subject prior to treatment with the chemotherapeutic agent such that the CDK4/6 inhibitor reaches peak serum levels before or during treatment with the chemotherapeutic agent, allowing for the inhibition of proliferation of immune effector cells, thus protecting them from the harmful effects of chemotherapy. In one embodiment, the CDK4/6 inhibitor is administered concomitantly, or closely thereto, with the chemotherapeutic agent exposure. Alternatively, the CDK4/6 inhibitor described herein can be administered following exposure to the chemotherapeutic agent if desired to mitigate immune effector cell damage associated with chemotherapeutic agent exposure. In one embodiment, the selective CDK4/6 inhibitor is a fast-acting, short half-life CDK4/6 inhibitor.

As contemplated herein, the specifically-timed administration of the selective, fast-acting, short half-life CDK4/6 inhibitor as described herein can be added to any chemotherapeutic agent/immune checkpoint inhibitor combination therapy protocol. For example, the selective, fast-acting, short half-life CDK4/6-inhibitor can be administered so that CDK4/6-replication dependent HSPCs and immune effector cells are arrested at the G1 phase during chemotherapeutic agent exposure wherein, due to the rapid dissipation of the G1-arresting effect of the selective, fast-acting, short half-life CDK4/6 inhibitors described herein, a significant number of immune effector cells reenter the cell-cycle and are capable of replicating and being activated shortly after chemotherapeutic agent exposure when chemotherapeutic induced cancer cell death and tumor antigen exposure is highest. In certain embodiments, the selective, fast-acting, short half-life CDK4/6-inhibitor is administered prior to or concomitantly with the administration of a chemotherapeutic agent, wherein the chemotherapeutic agent is administered: for example, on day 1-3 every 21 days; on days 1-3 every 28 days; on day 1 every 3 weeks; on day 1, day 8, and day 15 every 28 days, on day 1 and day 8 every 28 days; on days 1 and 8 every 21 days; on days 1-5 every 21 days; 1 day a week for 6-8 weeks; on days 1, 22, and 43; days 1 and 2 weekly; days 1-4 and 22-25; 1-4; 22-25, and 43-46; and similar type chemotherapeutic regimens. In one embodiment, the selective, fast-acting, short half-life CDK4/6 inhibitor is administered prior to or concomitantly with at least one administration of the chemotherapeutic agent during a chemotherapeutic treatment regimen. In one embodiment, the selective, fast-acting, short half-life CDK4/6 is administered prior to or concomitantly with one or more administrations of the chemotherapeutic agent during a chemotherapeutic treatment regimen. In one embodiment, the selective, fast-acting, short half-life CDK4/6 inhibitor is administered prior to or concomitantly with each administration of the chemotherapeutic agent during a chemotherapeutic treatment regimen.

The present invention includes the administration of an immune checkpoint inhibitor. Immune checkpoint inhibitors are known in the art and include, for example but are not limited to, PD-1 inhibitors, PD-L1 inhibitors, and CTLA-4 inhibitors, and others as described herein, and wherein the inhibitor may be a small molecule, an antibody, other protein, or biologic. In one embodiment, the immune checkpoint inhibitor is administered concomitantly with the administration of the CDK4/6 inhibitor and chemotherapeutic agent. In one embodiment, the immune checkpoint inhibitor is administered concomitantly with the administration of the CDK4/6 inhibitor and chemotherapeutic agent, and then administered at regular intervals thereafter, for example, one time a week, two times a week, three times a week or more in order to maintain the immune checkpoint inhibitor effect. In other embodiments, the immune checkpoint inhibitor can be administered according to a predetermined therapeutic cycle, for example on day 1 of a 21-day cycle, day 1, 8, and 15 of a 21-day cycle, and so forth.

In one aspect of the invention, provided is a method of treating a cancer in a subject comprising administering to the subject a dosing regimen that includes the administration of a chemotherapeutic agent in combination with a CDK4/6 inhibitor and an immune checkpoint inhibitor. The CDK4/6 inhibitor is administered in a specifically-timed manner prior to or concomitantly with the administration of the chemotherapeutic agent. In one embodiment, the immune checkpoint inhibitor is administered prior to or concomitantly with each administration of the chemotherapeutic agent. In one embodiment, the immune checkpoint inhibitor is administered prior to or concomitantly with at least one administration of the chemotherapeutic agent and a CDK4/6 inhibitor. In one embodiment, the immune checkpoint inhibitor is administered prior to or concomitantly with each administration of the chemotherapeutic agent. In one embodiment, the immune checkpoint inhibitor is administered to the subject one or more times in combination with the chemotherapeutic agent and CDK4/6 inhibitor during an initial induction phase. In one embodiment, the immune checkpoint inhibitor is administered to the subject one or more times in combination with the chemotherapeutic agent and CDK4/6 inhibitor during an induction phase, and one or more times alone, for example without concomitant administration of a chemotherapeutic agent and CDK4/6 inhibitor, during a maintenance phase. In one embodiment, the selective CDK4/6 inhibitor is a fast-acting, short half-life CDK4/6 inhibitor.

In one embodiment, the CDK4/6 inhibitor is administered prior to or concomitantly with each administration of a chemotherapeutic agent for example during a standard chemotherapeutic protocol such as, for example, a 21-day cycle, and the checkpoint inhibitor is administered on day 1. Following cessation of the standard chemotherapeutic protocol, the immune checkpoint inhibitor is further administered alone in a maintenance dose. In one embodiment, the immune checkpoint inhibitor is further administered one time, two times, three times a week, or more, for at least 3, 4, 5, 6, 7, 8, 9, 10, 11, 12, 13, 14, 15, or 16 weeks, or longer. In one embodiment, the checkpoint inhibitor is administered once every 21 days. In one embodiment, both the induction phase and maintenance phase are repeated at least 2 times, at least 3 times, at least 4 times or more. In one embodiment, the induction phase is repeated at least 4 times, and the maintenance phase is repeated four or more times, for example, 4, 5, 6, 7, 8, 9, 10, 11, 12 or more times. In one embodiment, the selective CDK4/6 inhibitor is a fast-acting, short half-life CDK4/6 inhibitor.

As contemplated herein, a CDK4/6 inhibitor, for example a fast-acting, short half-life CDK4/6 inhibitor, which is specifically-timed as described herein is administered in combination with a chemotherapeutic agent and an immune checkpoint inhibitor. In one embodiment, the immune checkpoint inhibitor is a PD-L1 inhibitor, a PD-1 inhibitor, or a CTLA-4 inhibitor. In one embodiment, the immune checkpoint inhibitor is administered concomitantly with the administration of the chemotherapeutic agent. In one embodiment, the immune checkpoint inhibitor is administered subsequent to administration of the CDK4/6 inhibitor and the chemotherapeutic agent. In one embodiment, the immune checkpoint inhibitor is administered one time, two times, three times, or more during the chemotherapeutic cycle. In one embodiment, the selective CDK4/6 inhibitor is a fast-acting, short half-life CDK4/6 inhibitor.

Also contemplated herein is the specifically-timed administration of a CDK4/6 inhibitor in combination with an immune checkpoint inhibitor such as a PD-L1 inhibitor, PD-1 inhibitor, or CTLA-4 inhibitor, wherein the CDK4/6 inhibitor/immune checkpoint inhibitor combination is administered to maintain immune effector cell response following the end of a CDK4/6 inhibitor/chemotherapeutic agent/immune checkpoint inhibitor treatment regimen. For example, following the completion of a CDK4/6 inhibitor/chemotherapeutic agent/immune checkpoint inhibitor treatment regimen (i.e., an induction phase), a CDK4/6 inhibitor in combination with the immune checkpoint inhibitor can be administered to the subject at periodic intervals for the maintenance of the immune effector cell response (i.e., a maintenance phase). In one embodiment, the maintenance regimen of CDK4/6 inhibitor/immune checkpoint inhibitor combination is administered at least one or more times following cessation of the original therapeutic regimen. In one embodiment, the maintenance regimen is administered once a week, twice a month, once a month, once every six weeks, or from time to time as necessary. In one embodiment, the selective CDK4/6 inhibitor is a fast-acting, short half-life CDK4/6 inhibitor.

In certain aspects, following the completion of a CDK4/6 inhibitor/chemotherapeutic agent/immune checkpoint inhibitor treatment regimen (i.e., an induction phase), the immune checkpoint inhibitor alone can be administered to the subject at periodic intervals for the maintenance of the immune effector cell response (i.e., a maintenance phase).

As contemplated herein, the subject can have any type of cancer, tumor, or abnormal cell proliferation. In one embodiment, the subject has a CDK4/6-replication independent cancer. The CDK4/6 replication independent cancer may be one of, but not limited to, small cell lung cancer, triple-negative breast cancer, HPV-positive head and neck cancer, retinoblastoma, Rb-negative bladder cancer, Rb negative prostate cancer, osteosarcoma, or cervical cancer. In one embodiment, the subject has small cell lung carcinoma.

In one embodiment, the subject has a CDK4/6-replication dependent cancer. The CDK4/6-replication dependent cancer may be one of, but not limited to, non-small cell lung carcinoma, Rb-positive breast cancer, colon cancer, ovarian cancer, non-small cell lung cancer, prostate cancer, and glioblastoma. In one embodiment, the CDK4/6-replication dependent cancer is Rb-positive breast cancer. In one embodiment, the CDK4/6-replication dependent cancer is non-small cell lung carcinoma.

In one embodiment, the subject has a cancer that expresses PD-L1. In one embodiment, the PD-L1 expressing cancer is selected from small cell lung carcinoma, non-small cell lung carcinoma, bladder cancer, renal cell carcinoma, gastric cancer, head and neck cancer, mesothelioma, Merkel-cell carcinoma, ovarian, melanoma, or other solid tumors.

In one embodiment, the subject has bladder cancer, gastroesophageal cancer, soft tissue sarcoma, cholangio/gall bladder cancer, ovarian cancer, or cervical cancer.

In one embodiment, the subject has small cell lung cancer and is administered a chemotherapeutic agent selected from the group consisting of carboplatin, cisplatin, etoposide, and topotecan, or a combination thereof, in combination with the specifically-timed administration of a CDK4/6 inhibitor and also an immune checkpoint inhibitor. In one embodiment, the CDK4/6 inhibitor is Compound I and the immune checkpoint inhibitor is selected from a PD-L1 inhibitor, PD-1 inhibitor, or CTLA-4 inhibitor. In one embodiment, the immune checkpoint inhibitor is a PD-L1 inhibitor. In one embodiment, the PD-L1 inhibitor is atezolizumab. In one embodiment, the chemotherapeutic agent is etoposide. In one embodiment, the chemotherapeutic agent is carboplatin. In one embodiment, the chemotherapeutic agent is a combination therapeutic regime comprising carboplatin and etoposide. In one embodiment, the chemotherapeutic agent is cisplatin. In one embodiment, the chemotherapeutic agent is topotecan.

In one embodiment, the subject has melanoma and is administered a chemotherapeutic agent selected from the group consisting of dacarbazine, temozolomide, nab-paclitaxel, paclitaxel, cisplatin, oxaliplatin, carboplatin, vinblastine, or a combination thereof, in combination with a CDK4/6 inhibitor and an immune checkpoint inhibitor. In one embodiment, the CDK4/6 inhibitor is Compound I. In one embodiment, the immune checkpoint inhibitor is a PD-L1 inhibitor, PD-1 inhibitor, or CTLA-4 inhibitor. In one embodiment, the immune checkpoint inhibitor is a PD-L1 inhibitor. In one embodiment, the PD-L1 inhibitor is atezolizumab. In one embodiment, the chemotherapeutic agent is dacarbazine. In one embodiment, the chemotherapeutic agent is temozolomide. In one embodiment, the chemotherapeutic agent is nab-paclitaxel. In one embodiment, the chemotherapeutic agent is paclitaxel. In one embodiment, the chemotherapeutic agent is cisplatin. In one embodiment, the chemotherapeutic agent is carboplatin. In one embodiment, the chemotherapeutic agent is vinblastine. In one embodiment, the chemotherapeutic agent is platinum drug.

In one embodiment, the subject has renal cell carcinoma and is administered a chemotherapeutic agent selected from the group consisting of vinblastine, floxuridine, 5-fluorouracil (5-FU), capecitabine, and gemcitabine, or a combination thereof, in combination with a CDK4/6 inhibitor and an immune checkpoint inhibitor. In one embodiment, the CDK4/6 inhibitor is Compound I. In one embodiment the immune checkpoint inhibitor is selected from a PD-L1 inhibitor, a PD-1 inhibitor, and a CTLA-4 inhibitor. In one embodiment, the immune checkpoint inhibitor is a PD-L1 inhibitor. In one embodiment, the PD-L1 inhibitor is atezolizumab. In one embodiment, the chemotherapeutic agent is vinblastine. In one embodiment, the chemotherapeutic agent is floxuridine. In one embodiment, the chemotherapeutic agent is 5-fluorouracil. In one embodiment, the chemotherapeutic agent is capecitabine. In one embodiment, the chemotherapeutic agent is gemcitabine.

In one embodiment, the subject has bladder cancer and is administered a chemotherapeutic agent selected from the group consisting of carboplatin, oxaliplatin, cisplatin, fluorouracil, mitomycin, methotrexate, vinblastine, doxorubicin, gemcitabine, paclitaxel, or a combination thereof in combination with a CDK4/6 inhibitor and an immune checkpoint inhibitor. In one embodiment, the CDK4/6 inhibitor is Compound I. In one embodiment, the immune checkpoint inhibitor is selected from a PD-L1, PD-1 inhibitor, and a CTLA-4 inhibitor. In one embodiment, the immune checkpoint inhibitor is a PD-L1 inhibitor. In one embodiment, the PD-L1 inhibitor is atezolizumab. In one embodiment, the chemotherapeutic agent is cisplatin. In one embodiment, the chemotherapeutic agent is a combination therapeutic regime comprising cisplatin and 5-fluorouracil. In one embodiment, the chemotherapeutic agent is a combination therapeutic regime comprising mitomycin and 5-fluorouracil. In one embodiment, the chemotherapeutic agent is a combination therapeutic regime comprising cisplatin and gemcitabine. In one embodiment, the chemotherapeutic agent is a combination therapeutic regime comprising cisplatin, methotrexate, vinblastine and doxorubicin. In one embodiment, the chemotherapeutic agent is a combination therapeutic regime comprising cisplatin, methotrexate, and vinblastine. In one embodiment, the chemotherapeutic agent is a combination therapeutic regime comprising carboplatin and paclitaxel. In one embodiment, the chemotherapeutic agent is oxaliplatin.

In one embodiment, the subject has urothelial carcinoma and is administered a chemotherapeutic agent selected from the group consisting of carboplatin, cisplatin, oxaliplatin, fluorouracil, mitomycin, methotrexate, vinblastine, doxorubicin, gemcitabine, paclitaxel, or a combination thereof, in combination with a CDK4/6 inhibitor and an immune checkpoint inhibitor. In one embodiment, the CDK4/6 inhibitor is Compound I. In one embodiment, the immune checkpoint inhibitor is selected from a PD-L1 inhibitor, PD-1 inhibitor, or CTLA-4 inhibitor. In one embodiment, the immune checkpoint inhibitor is a PD-L1 inhibitor. In one embodiment, the PD-L1 inhibitor is atezolizumab. In one embodiment, the chemotherapeutic agent is cisplatin. In one embodiment, the chemotherapeutic agent is a combination therapeutic regime comprising cisplatin and 5-fluorouracil. In one embodiment, the chemotherapeutic agent is a combination therapeutic regime comprising mitomycin and 5-fluorouracil. In one embodiment, the chemotherapeutic agent is a combination therapeutic regime comprising cisplatin and gemcitabine. In one embodiment, the chemotherapeutic agent is a combination therapeutic regime comprising cisplatin, methotrexate, vinblastine and doxorubicin. In one embodiment, the chemotherapeutic agent is a combination therapeutic regime comprising cisplatin, methotrexate, and vinblastine. In one embodiment, the chemotherapeutic agent is a combination therapeutic regime comprising carboplatin and paclitaxel. In one embodiment, the chemotherapeutic agent is oxaliplatin.

In one embodiment, the subject has breast cancer and is administered a chemotherapeutic agent selected from the group consisting of carboplatin, oxaliplatin, cisplatin, doxorubicin, 5-fluorouracil, paclitaxel, cyclophosphamide, gemcitabine or a combination thereof, in combination with a CDK4/6 inhibitor and a checkpoint inhibitor. In one embodiment, the CDK4/6 inhibitor is Compound I. In one embodiment, the immune checkpoint inhibitor is a PD-L1 inhibitor, PD-1 inhibitor, or CTLA-4 inhibitor. In one embodiment, the immune checkpoint inhibitor is a PD-L1 inhibitor. In one embodiment, the PD-L1 inhibitor is atezolizumab. In one embodiment, the chemotherapeutic agent is carboplatin. In one embodiment, the chemotherapeutic agent is cisplatin. In one embodiment, the chemotherapeutic agent is a combination therapeutic regime comprising cisplatin and 5-fluorouracil. In one embodiment, the chemotherapeutic agent is a combination therapeutic regime comprising cisplatin and gemcitabine. In one embodiment, the chemotherapeutic agent is doxorubicin. In one embodiment, the chemotherapeutic agent is cyclophosphamide. In one embodiment, the chemotherapeutic agent is paclitaxel. In one embodiment, the chemotherapeutic agent is oxaliplatin.

In one embodiment, the subject has colorectal cancer and is administered a chemotherapeutic agent selected from the group consisting of 5-fluorouracil, capecitabine, irinotecan, oxaliplatin, trifluridinen, and tipiracil, or a combination thereof in combination with a CDK4/6 inhibitor and an immune checkpoint inhibitor. In one embodiment, the CDK4/6 inhibitor is Compound I. In one embodiment, the immune checkpoint inhibitor is a PD-L1 inhibitor, PD-1 inhibitor, or CTLA-4 inhibitor. In one embodiment, the immune checkpoint inhibitor is a PD-L1 inhibitor. In one embodiment, the PD-L1 inhibitor is atezolizumab. In one embodiment, the chemotherapeutic agent is 5-fluorouracil. In one embodiment, the chemotherapeutic agent is capecitabine. In one embodiment, the chemotherapeutic agent is a combination therapeutic regime comprising trifluridinen and tipiracil. In one embodiment, the chemotherapeutic agent is irinotecan. In one embodiment, the chemotherapeutic agent is oxaliplatin.

In one embodiment, the subject has castration-resistant prostate cancer and is administered a chemotherapeutic agent selected from the group consisting of docetaxel, cabazitaxel, mitoxantrone, and estramustine, or a combination thereof in combination with a CDK4/6 inhibitor and an immune checkpoint inhibitor. In one embodiment, the CDK4/6 inhibitor is Compound I. In one embodiment, the immune checkpoint inhibitor is a PD-L1 inhibitor, PD-1 inhibitor, or CTLA-4 inhibitor. In one embodiment, the immune checkpoint inhibitor is a PD-L1 inhibitor. In one embodiment, the PD-L1 inhibitor is atezolizumab. In one embodiment, the chemotherapeutic agent is docetaxel. In one embodiment, the chemotherapeutic agent is cabazitaxel. In one embodiment, the chemotherapeutic agent is mitoxantrone. In one embodiment, the chemotherapeutic agent is estramustine.

In one embodiment, the subject has PD-L1-expressing tumors and is being administered a chemotherapeutic agent selected from the group consisting of carboplatin, cisplatin, gemcitabine, etoposide, 5-fluorouracil, paclitaxel, oxaliplatin, and topotecan, or a combination thereof in combination with Compound I and atezolizumab. In one embodiment, the chemotherapeutic agent is etoposide. In one embodiment, the chemotherapeutic agent is carboplatin. In one embodiment, the chemotherapeutic agent is a combination therapeutic regime comprising carboplatin and etoposide. In one embodiment, the chemotherapeutic agent is cisplatin. In one embodiment, the chemotherapeutic agent is topotecan. In one embodiment, the chemotherapeutic agent is oxaliplatin. In one embodiment, the chemotherapeutic agent is a combination therapeutic regime comprising cisplatin and 5-fluorouracil. In one embodiment, the chemotherapeutic agent is doxorubicin.

In one aspect of the present invention, provided is a method of treating a subject having cancer comprising administering to the subject a therapeutic regimen comprising an induction phase and a maintenance phase, the induction phase comprising: administering to the subject an effective amount of a selective CDK4/6 inhibitor, administering to the subject an effective amount of a chemotherapeutic agent, and administering to the subject an effective amount of an immune checkpoint inhibitor; wherein the CDK4/6 inhibitor is administered prior to or concomitantly to the administration of the chemotherapeutic agent; and wherein the chemotherapeutic agent is cytotoxic to immune effector cells; and the maintenance phase comprising administering to the subject at least one dose of an effective amount of the immune checkpoint inhibitor, wherein the maintenance phase is administered following the cessation of the induction phase. In one embodiment, the selective CDK4/6 inhibitor is a fast-acting, short half-life CDK4/6 inhibitor.

In one embodiment, provided is a method of treating a subject having small cell lung cancer comprising administering to the subject a therapeutic regimen comprising a 21-day induction phase and a 21-day maintenance phase, the induction phase comprising: administering to the subject an effective amount of carboplatin on day 1 of the 21-day cycle; administering to the subject an effective amount of etoposide on days 1, 2, and 3 of the 21-day cycle; administering to the subject an effective amount of a selective CDK4/6 inhibitor on days 1, 2, and 3 of the 21-day cycle; and administering to the subject an effective amount of an immune checkpoint inhibitor on day 1 of the 21-day cycle; and the maintenance phase comprising administering to the subject an effective amount of the immune checkpoint inhibitor on day 1 of the 21-day cycle, wherein the maintenance phase is administered following the cessation of the induction phase. In one embodiment, the selective CDK4/6 inhibitor is a fast-acting, short half-life CDK4/6 inhibitor.

In one embodiment, provided is a method of treating a subject having small cell lung cancer comprising administering to the subject a therapeutic regimen comprising a 21-day induction phase and a 21-day maintenance phase, the induction phase comprising: administering to the subject an effective amount of carboplatin on day 2 of the 21-day cycle; administering to the subject an effective amount of etoposide on days 2, 3, and 4 of the 21-day cycle; administering to the subject an effective amount of a selective CDK4/6 inhibitor on days 1 to 4 of the 21-day cycle; and administering to the subject an effective amount of an immune checkpoint inhibitor on day 1 of the 21-day cycle; and the maintenance phase comprising administering to the subject an effective amount of the immune checkpoint inhibitor on day 1 of the 21-day cycle, wherein the maintenance phase is administered following the cessation of the induction phase. In one embodiment, the selective CDK4/6 inhibitor is a fast-acting, short half-life CDK4/6 inhibitor.

In one embodiment, provided is a method of treating a subject having small cell lung cancer comprising administering to the subject a therapeutic regimen comprising a 21-day induction phase and a 21-day maintenance phase, the induction phase comprising: administering to the subject an effective amount of topotecan on days 1 to 5 of the 21-day cycle; administering to the subject an effective amount of a selective CDK4/6 inhibitor on days 1 to 5 of the 21-day cycle; and administering to the subject an effective amount of an immune checkpoint inhibitor on day 1 of the 21 day cycle; and the maintenance phase comprising administering to the subject an effective amount of the immune checkpoint inhibitor on day 1 of the 21-day cycle, wherein the maintenance phase is administered following the cessation of the induction phase. In one embodiment, the selective CDK4/6 inhibitor is a fast-acting, short half-life CDK4/6 inhibitor.

In one embodiment, provided is a method of treating a subject having small cell lung cancer comprising administering to the subject a therapeutic regimen comprising a 21-day induction phase and a 21-day maintenance phase, the induction phase comprising: administering to the subject an effective amount of topotecan on days 2 to 6 of the 21-day cycle; administering to the subject an effective amount of a CDK4/6 inhibitor on days 1 to 6 of the 21-day cycle; and administering to the subject an effective amount of an immune checkpoint inhibitor on day 1 of the 21 day cycle; and the maintenance phase comprising administering to the subject an effective amount of the immune checkpoint inhibitor on day 1 of the 21-day cycle, wherein the maintenance phase is administered following the cessation of the induction phase. In one embodiment, the selective CDK4/6 inhibitor is a fast-acting, short half-life CDK4/6 inhibitor. In one embodiment, the CDK4/6 inhibitor is Compound I.

In one embodiment, provided is a method of treating a subject having Stage IV triple-negative breast cancer comprising administering to the subject a therapeutic regimen comprising a 21-day induction phase and a 21-day maintenance phase, the induction phase comprising: administering to the subject an effective amount of carboplatin on day 1 and day 8 of the 21-day cycle; administering to the subject an effective amount of gemcitabine on day 1 and day 8 of the 21-day cycle; and administering to the subject an effective amount of a selective CDK4/6 inhibitor on day 1 and day 8 of the 21-day cycle; and the maintenance phase comprising administering to the subject an effective amount of the immune checkpoint inhibitor on day 1 of the 21-day cycle, wherein the maintenance phase is administered following the cessation of the induction phase. In one embodiment, the selective CDK4/6 inhibitor is a fast-acting, short half-life CDK4/6 inhibitor.

In one embodiment, provided is a method of treating a subject having Stage IV triple-negative breast cancer comprising administering to the subject a therapeutic regimen comprising a 21-day induction phase and a 21-day maintenance phase, the induction phase comprising: administering to the subject an effective amount of carboplatin on day 2 and day 9 of the 21-day cycle; administering to the subject an effective amount of gemcitabine on day 2 and day 9 of the 21-day cycle; and administering to the subject an effective amount of a CDK4/6 inhibitor on day 1, day 2, day 8 and day 9 of the 21-day cycle; and the maintenance phase comprising administering to the subject an effective amount of the immune checkpoint inhibitor on day 1 of the 21-day cycle, wherein the maintenance phase is administered following the cessation of the induction phase. In one embodiment, the selective CDK4/6 inhibitor is a fast-acting, short half-life CDK4/6 inhibitor.

In one embodiment, provided is a method of treating a subject having small cell lung cancer comprising administering to the subject a therapeutic regimen comprising a 21-day induction phase and a 21-day maintenance phase, wherein the induction phase may be repeated up to 4 times, the induction phase comprising: administering to the subject an effective amount of carboplatin on day 1 of each 21-day cycle; administering to the subject an effective amount of etoposide on days 1, 2, and 3 of each 21-day cycle; administering atezolizumab on day 1 of each 21-day cycle; and administering a CDK4/6 inhibitor on days 1, 2, and 3 of each 21-day cycle; and the maintenance phase comprising administering atezolizumab on day 1 of the 21-day cycle, wherein the maintenance phase is administered following the cessation of the final induction phase. In one embodiment, the selective CDK4/6 inhibitor is a fast-acting, short half-life CDK4/6 inhibitor.

In one embodiment, provided is a method of treating a subject having small cell lung cancer comprising administering to the subject a therapeutic regimen comprising a 21-day induction phase and a 21-day maintenance phase, wherein the induction phase may be repeated up to 4 times, the induction phase comprising: administering to the subject an effective amount of carboplatin on day 2 of each 21-day cycle; administering to the subject an effective amount of etoposide on days 2, 3, and 4 of each 21-day cycle; administering atezolizumab on day 1 of each 21-day cycle; and administering a CDK4/6 inhibitor on days 1 to 4 of each 21-day cycle; and the maintenance phase comprising administering atezolizumab on day 1 of the 21-day cycle, wherein the maintenance phase is administered following the cessation of the final induction phase. In one embodiment, the selective CDK4/6 inhibitor is a fast-acting, short half-life CDK4/6 inhibitor.

In one embodiment, provided is a method of treating a subject having advanced or metastatic nonsquamous non-small cell lung cancer comprising administering to the subject a therapeutic regimen comprising a 21-day induction phase and a 21-day maintenance phase, wherein the induction phase may be repeated up to 4 times, the induction phase comprising: administering to the subject an effective amount of carboplatin on day 1 of each 21-day cycle; administering to the subject an effective amount of pemetrexed on day one of each 21-day cycle; administering to the subject an effective amount of pembrolizumab on day 1 of each 21-day cycle; and administering to the subject an effective amount of a CDK4/6 inhibitor on day 1 of each 21-day cycle; and the maintenance phase comprising administering to the subject an effective amount of pembrolizumab on day 1 of each 21-day cycle, wherein the maintenance phase is administered following the cessation of the final induction phase. In one embodiment, the selective CDK4/6 inhibitor is a fast-acting, short half-life CDK4/6 inhibitor.

In one embodiment, provided is a method of treating a subject having stage IIIB or Stage IV non-squamous non-small cell lung cancer without targetable EGFR or ALK genetic aberrations comprising administering to the subject a therapeutic regimen comprising a 21-day induction phase and a 21-day maintenance phase, wherein the induction phase may be repeated up to 4 times, the induction phase comprising: administering to the subject an effective amount of carboplatin on day 2 of each 21-day cycle; administering to the subject an effective amount of pemetrexed on day 2 of each 21-day cycle; administering to the subject an effective amount of pembrolizumab on day 1 of each 21-day cycle; and administering to the subject an effective amount of a CDK4/6 inhibitor on days 1 and 2 of each 21-day cycle; and the maintenance phase comprising administering to the subject an effective amount of pembrolizumab on day 1 of each 21-day cycle, wherein the maintenance phase is administered following the cessation of the final induction phase. In one embodiment, the selective CDK4/6 inhibitor is a fast-acting, short half-life CDK4/6 inhibitor.

In one embodiment, provided is a method of treating a subject having metastatic relapsed or refractory colorectal cancer comprising administering to the subject a therapeutic regimen comprising a 21 day induction phase and a 21-day maintenance phase, the induction phase comprising: administering to the subject an effective amount of irinotecan on day 1 of the 21-day cycle; administering to the subject an effective amount of a CDK4/6 inhibitor on day 1 of the 21-day cycle; and administering to the subject an effective amount of an immune checkpoint inhibitor on day 1 of the 21-day cycle; and the maintenance phase comprising administering to the subject an effective amount of the immune checkpoint inhibitor on day 1 of the 21-day cycle, wherein the maintenance phase is administered following the cessation of the induction phase. In one embodiment, the selective CDK4/6 inhibitor is a fast-acting, short half-life CDK4/6 inhibitor.

In one embodiment, provided is a method of treating a subject having metastatic relapsed or refractory colorectal cancer comprising administering to the subject a therapeutic regimen comprising a 21 day induction phase and a 21-day maintenance phase, the induction phase comprising: administering to the subject an effective amount of irinotecan on day 2 of the 21-day cycle; administering to the subject an effective amount of a CDK4/6 inhibitor on days 1 and 2 of the 21-day cycle; and administering to the subject an effective amount of an immune checkpoint inhibitor on day 1 of the 21-day cycle; and the maintenance phase comprising administering to the subject an effective amount of the immune checkpoint inhibitor on day 1 of the 21-day cycle, wherein the maintenance phase is administered following the cessation of the induction phase. In one embodiment, the selective CDK4/6 inhibitor is a fast-acting, short half-life CDK4/6 inhibitor.

In one embodiment, provided is a method of treating a subject having metastatic relapsed or refractory colorectal cancer comprising administering to the subject a therapeutic regimen comprising a 6 week induction phase and a 6 week maintenance phase, the induction phase comprising: administering to the subject an effective amount of irinotecan on days 1, 8, 15, and 22 of the 6 week cycle; administering to the subject an effective amount of a CDK4/6 inhibitor on days 1, 8, 15 and 22 of the 6 week cycle; and administering an immune checkpoint inhibitor on day 1 and 22 of the 6 week cycle, and the maintenance phase comprising administering an effective amount of the checkpoint days 1 and 22 of the 6 week cycle, wherein the maintenance phase is administered following the cessation of the induction phase. In one embodiment, the selective CDK4/6 inhibitor is a fast-acting, short half-life CDK4/6 inhibitor.

In one embodiment, provided is a method of treating a subject having metastatic relapsed or refractory colorectal cancer comprising administering to the subject a therapeutic regimen comprising a 6 week induction phase and a 6 week maintenance phase, the induction phase comprising: administering to the subject an effective amount of irinotecan on days 2, 9, 16, and 23 of the 6 week cycle; administering to the subject an effective amount of a CDK4/6 inhibitor on days 1, 2, 8, 9, 15, 16, 22 and 23 of the 6 week cycle; and administering an immune checkpoint inhibitor on day 1 and 22 of the 6 week cycle, and the maintenance phase comprising administering an effective amount of the checkpoint days 1 and 22 of the 6 week cycle, wherein the maintenance phase is administered following the cessation of the induction phase. In one embodiment, the selective CDK4/6 inhibitor is a fast-acting, short half-life CDK4/6 inhibitor.

In one embodiment, provided is a method of treating a subject having recurrent platinum-sensitive ovarian cancer comprising administering to the subject a therapeutic regimen comprising a 21-day induction phase and a 21-day maintenance phase, wherein the induction phase may be repeated up to 6 times, the induction phase comprising: administering to the subject an effective amount of carboplatin on day 1 of each 21-day cycle; administering to the subject an effective amount of docetaxel on day 1 of each 21-day cycle; administering to the subject an effective amount of a CDK4/6 inhibitor on day 1 of each 21-day cycle; and administering to the subject an effective amount of an immune checkpoint inhibitor on day 1 of each 21-day cycle; and the maintenance phase comprising administering to the subject an effective amount of the immune checkpoint inhibitor on day 1 of the 21-day cycle, wherein the maintenance phase is administered following the cessation of the final induction phase. In one embodiment, the selective CDK4/6 inhibitor is a fast-acting, short half-life CDK4/6 inhibitor.

In one embodiment, provided is a method of treating a subject having recurrent platinum-sensitive ovarian cancer comprising administering to the subject a therapeutic regimen comprising a 21-day induction phase and a 21-day maintenance phase, wherein the induction phase may be repeated up to 6 times, the induction phase comprising: administering to the subject an effective amount of carboplatin on day 2 of each 21-day cycle; administering to the subject an effective amount of docetaxel on day 2 of each 21-day cycle; administering to the subject an effective amount of a CDK4/6 inhibitor on days 1 and 2 of each 21-day cycle; and administering to the subject an effective amount of an immune checkpoint inhibitor on day 1 of each 21-day cycle; and the maintenance phase comprising administering to the subject an effective amount of the immune checkpoint inhibitor on day 1 of the 21-day cycle, wherein the maintenance phase is administered following the cessation of the final induction phase. In one embodiment, the selective CDK4/6 inhibitor is a fast-acting, short half-life CDK4/6 inhibitor.

In one embodiment, provided is a method of treating a subject having metastatic pancreatic cancer comprising administering to the subject a therapeutic regimen comprising a 14-day induction phase and a 14-day maintenance phase, the induction phase comprising: administering to the subject an effective amount of the combination of 5-FU and leucovorin on days 1 and 2 of the 14-day cycle; administering to the subject an effective amount of oxaliplatin on day 1 of the 14-day cycle; administering to the subject an effective amount of irinotecan on day 1 of the 14-day cycle; administering to the subject an effective amount of a CDK4/6 inhibitor on days 1 and 2 of the 14-day cycle; and administering to the subject an effective amount of an immune checkpoint inhibitor on day 1 of the 14-day cycle; and the maintenance phase comprising administering to the subject an effective amount of the immune checkpoint inhibitor on day 1 of the 14-day cycle, wherein the maintenance phase is administered following the cessation of the induction phase. In one embodiment, the selective CDK4/6 inhibitor is a fast-acting, short half-life CDK4/6 inhibitor.

In one embodiment, provided is a method of treating a subject having metastatic pancreatic cancer comprising administering to the subject a therapeutic regimen comprising a 14-day induction phase and a 14-day maintenance phase, the induction phase comprising: administering to the subject an effective amount of the combination of 5-FU and leucovorin on days 2 and 3 of the 14-day cycle; administering to the subject an effective amount of oxaliplatin on day 2 of the 14-day cycle; administering to the subject an effective amount of irinotecan on day 2 of the 14-day cycle; administering to the subject an effective amount of a CDK4/6 inhibitor on days 1 to 3 of the 14-day cycle; and administering to the subject an effective amount of an immune checkpoint inhibitor on day 1 of the 14-day cycle; and the maintenance phase comprising administering to the subject an effective amount of the immune checkpoint inhibitor on day 1 of the 14-day cycle, wherein the maintenance phase is administered following the cessation of the induction phase. In one embodiment, the selective CDK4/6 inhibitor is a fast-acting, short half-life CDK4/6 inhibitor.

In one embodiment, provided is a method of treating a subject having metastatic pancreatic cancer comprising administering to the subject a therapeutic regimen comprising a 28-day induction phase and a 28-day maintenance phase, the induction phase comprising: administering to the subject an effective amount of gemcitabine on days 1, 8, and 15 of the 28-day cycle; administering to the subject an effective amount of abraxane on days 1, 8, and 15 of the 28-day cycle; administering to the subject an effective amount of the CDK4/6 inhibitor on days 1, 8, and 15 of the 28-day cycle; and administering to the subject an effective amount of an immune checkpoint inhibitor on day 1 of the 28 day cycle; and the maintenance phase comprising administering to the subject an effective amount of the immune checkpoint inhibitor on day 1 of the 28-day cycle, wherein the maintenance phase is administered following the cessation of the induction phase. In one embodiment, the selective CDK4/6 inhibitor is a fast-acting, short half-life CDK4/6 inhibitor.

In one embodiment, provided is a method of treating a subject having metastatic pancreatic cancer comprising administering to the subject a therapeutic regimen comprising a 28-day induction phase and a 28-day maintenance phase, the induction phase comprising: administering to the subject an effective amount of gemcitabine on days 2, 9, and 16 of the 28-day cycle; administering to the subject an effective amount of abraxane on days 2, 9, and 16 of the 28-day cycle; administering to the subject an effective amount of the CDK4/6 inhibitor on days 1, 2, 8, 9, 15 and 16 of the 28-day cycle; and administering to the subject an effective amount of an immune checkpoint inhibitor on day 1 of the 28 day cycle; and the maintenance phase comprising administering to the subject an effective amount of the immune checkpoint inhibitor on day 1 of the 28-day cycle, wherein the maintenance phase is administered following the cessation of the induction phase. In one embodiment, the selective CDK4/6 inhibitor is a fast-acting, short half-life CDK4/6 inhibitor.

In one embodiment, provided is a method of treating a subject having a soft tissue sarcoma comprising administering to the subject a therapeutic regimen comprising a 21-day induction phase and a 21-day maintenance phase, the induction phase comprising: administering to the subject an effective amount of doxorubicin on day 1 of the 21-day cycle; administering to the subject an effective amount of ifosfamide on days 1 to 4 of the 21-day cycle; administering to the subject an effective amount of a CDK4/6 inhibitor on days 1 to 4 of the 21-day cycle; and administering to the subject an effective amount of an immune checkpoint inhibitor on day 1 of the 21-day cycle; and the maintenance phase comprising administering to the subject an effective amount of the immune checkpoint inhibitor on day 1 of the 21-day cycle, wherein the maintenance phase is administered following the cessation of the induction phase. In one embodiment, the selective CDK4/6 inhibitor is a fast-acting, short half-life CDK4/6 inhibitor.

In one embodiment, provided is a method of treating a subject having a soft tissue sarcoma comprising administering to the subject a therapeutic regimen comprising a 21-day induction phase and a 21-day maintenance phase, the induction phase comprising: administering to the subject an effective amount of doxorubicin on day 2 of the 21-day cycle; administering to the subject an effective amount of ifosfamide on days 2 to 5 of the 21-day cycle; administering to the subject an effective amount of a CDK4/6 inhibitor on days 1 to 5 of the 21-day cycle; and administering to the subject an effective amount of an immune checkpoint inhibitor on day 1 of the 21-day cycle; and the maintenance phase comprising administering to the subject an effective amount of the immune checkpoint inhibitor on day 1 of the 21-day cycle, wherein the maintenance phase is administered following the cessation of the induction phase. In one embodiment, the selective CDK4/6 inhibitor is a fast-acting, short half-life CDK4/6 inhibitor. In one embodiment, the CDK4/6 inhibitor is Compound I.

In one embodiment, the selective, fast-acting, short half-life CDK4/6 inhibitor dosed as described herein is combined in a single dosage form with an immune checkpoint inhibitor. In one embodiment, the immune checkpoint inhibitor is a PD-L1 inhibitor. In one embodiment, the PD-L1 inhibitor is atezolizumab.

In one embodiment, the selective, fast-acting, short half-life CDK4/6 inhibitor is combined in a single dosage form with the CTLA-4 inhibitor. In one embodiment the CTLA-4 inhibitor is ipilimumab (Yervoy®).

In one embodiment, the selective, fast-acting, short half-life CDK4/6 inhibitor is combined in a single dosage form with the PD-1 inhibitor. In one embodiment the PD-1 inhibitor is nivolumab (Opdivo®). In one embodiment, the PD-1 inhibitor is pembrolizumab (Keytruda®).

In one embodiment, the subject or host is a mammal, including a human.

DETAILED DESCRIPTION

Figure 1:
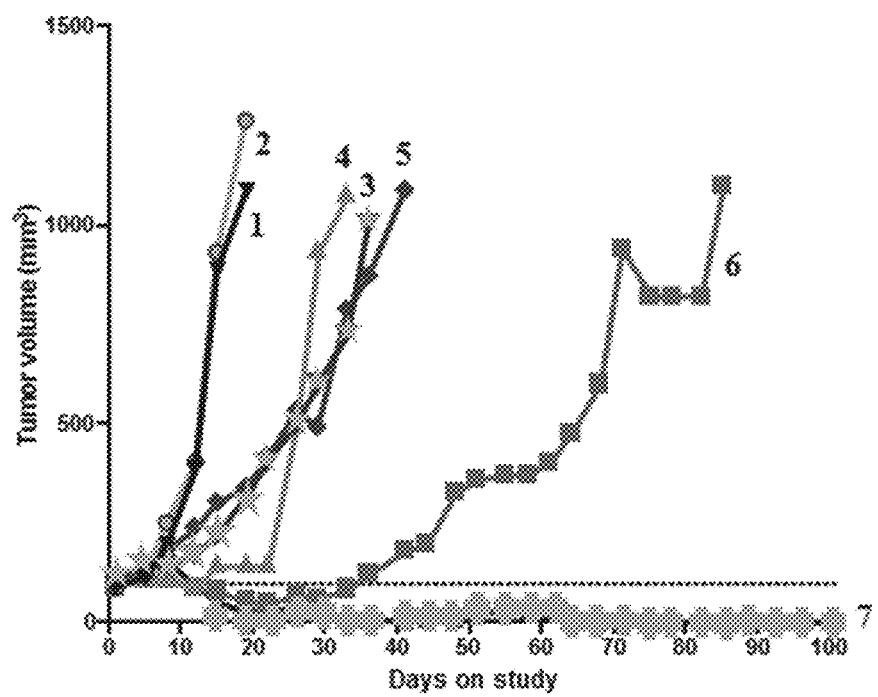
FIG. 1 depicts tumor growth rate over 100 days in a syngeneic MC38 mouse tumor model following treatment with (1) vehicle, (2) Compound I (100 mg/kg), (3) oxaliplatin, (4) anti-mouse PD-L1, (5) Compound I+oxaliplatin, (6) oxaliplatin (administered on days 1, 8, and 15) and anti-mouse PD-L1 (administered on days 1, 4, 8, and 11), and (7) Compound I+oxaliplatin (administered on days 1, 8, 15)+anti-mouse PD-L1 (administered on days 1, 4, 8, and 11). The x-axis represents study length measured in days and the y-axis represents tumor volume measured in $mm^3$.

It has been surprisingly and unexpectedly discovered that the addition of a CDK 4/6 inhibitor in a very specific dosage regimen to the combination of chemotherapy with a checkpoint inhibitor provides superior results in the treatment of a tumor or cancer. The unexpected discovery is that the specifically-timed administration of a selective CDK 4/6 inhibitor during administration of the chemotherapy portion of the triple combination therapy has a profound effect on the immune cells in the cancer microenvironment. The result is remarkable in that the very specific timed administration of the selective, fast-acting, short half-life CDK 4/6 inhibitor provides one or more of: protection of immune tumor cell infiltrates from damage, an increased durability of the immune response via a higher frequency of tumor-specific memory T-cells, a deeper decrease in immune suppressor intra-tumor Treg cells; and/or a change in the gene expression of pro-inflammatory agents. The expression of genes functionally enriched for lymphocyte activation and upregulation of the pro-inflammatory cytokine interferon-γ is significantly enhanced. In parallel, several genes involved in immunosuppressive reactive oxygen species metabolic processes are down-regulated. These findings indicate that the specific timed administration of a CDK 4/6 inhibitor, for example a fast-acting, short half-life CDK4/6 inhibitor, leads to modulation of gene expression, resulting in a pro-inflammatory tumor microenvironment that is favorable for increasing checkpoint inhibitor activity. This improvement provides a significant advance in the state of the art of cancer treatment.

Non-limiting examples of CDK4/6 inhibitors contemplated for use herein, are for example, but not limited to, Compounds I, II, III, and IV, which are highly potent and selective, reversible, cyclin-dependent kinase (CDK)4/6 inhibitors that transiently produce a G0/G1 cell cycle arrest of HSPCs and immune effector cells. These cells are dependent upon CDK4/6 for proliferation and are arrested in the G0/G1 phase of the cell cycle upon exposure to, for example, Compound I. When HSPCS and other immune effector cells are transiently arrested in G0/G1, they are more resistant to the DNA damaging effects of chemotherapy, thus reducing subsequent immune cell toxicity. Furthermore, it has been found that the use of a CDK4/6 inhibitor in combination with a chemotherapeutic agent and an immune checkpoint inhibitor for the treatment of cancer augments the anti-cancer immune response. By specific timing of the administration of the CDK4/6 inhibitor, the immune effector cells are protected from chemotherapeutic agent damage, and are allowed to reenter cell replication shortly after the DNA-damaging effects of the chemotherapeutic agent has dissipated, providing improved immune responsiveness when compared to strategies using CDK4/6 inhibitors which are administered in a daily manner, which results in complete and durable inhibition of CDK4/6.

Initial attempts at immunotherapies focused on the use of cytokines in combination with chemotherapy, so-called "chemoimmunotherapy." This approach, however, was hampered by high rates of toxicity without significant improvement in survival outcomes (Atzpodien, J.; Kirchner, H.; Rebmann, U.; Soder, M.; Gertenbach, U.; Siebels, M.; Roigas, J.; Raschke, R.; Salm, S.; Schwindi, B.; et al. Interleukin-2/interferon-alpha2a/13-retinoic acid-based chemoimmunotherapy in advanced renal cell carcinoma: Results of a prospectively randomised trial of the German Cooperative Renal Carcinoma Chemoimmunotherapy Group (DGCIN). Br. J. Cancer 2006, 95, 463-469). Interestingly, cytokine therapies provided robust benefit only in a subset of patients, mostly in those who developed clinical or serologic evidence of autoimmunity (Gogas, H.; Ioannovich, J.; Dafni, U.; Stavropoulou-Giokas, C.; Frangia, K.;

Tsoutsos, D.; Panagiotou, P.; Polyzos, A.; Papadopoulos, O.; Stratigios, A.; et al. Prognostic significance of autoimmunity during treatment of melanoma with interferon. N. Engl. J. Med. 2006, 354, 709-718). Other immunomodulating agents have been administered with mixed results. For example, Levamisole, an antihelminthic drug, was found to have immune potentiation properties and was approved in colorectal cancer as an adjunct to 5-fluorouracil (5-FU) but later studies seemed to show no benefit. (Wolmark, N.; Rockette, H.; Mamounas, E.; Jones, J.; Wieand, S.; Wickerham, D. L.; Bear, H. D.; Atkins, J. N.; Dimitrov, N. V.; Glass, A. G.; et al. Clinical trial to assess the relative efficacy of fluorouracil and leucovorin, fluorouracil and levamisole, and fluorouracil, leucovorin, and levamisole in patients with Dukes' B and C Carcinoma of the colon: Results from National Surgical Adjuvant Breast and Bowel Project C-04. J. Clin. Oncol. 1999, 17, 3553-3559). *Bacillus* Calmette-Guerin (BCG) was developed as a vaccine against Tuberculosis but provided robust anti-cancer responses when given intravesically in bladder cancer and continues to be the standard of care for superficially invasive bladder cancer since it was first approved in 1990 for this indication. (Mungan, N. A.; Witjes, J. A. Bacille Calmette-Guérin in superficial transitional cell carcinoma. Br. J. Urol. 1998, 82, 213-223; Sylvester, R. J.; van der Meijden, A. P.; Witjes, J. A.; Kurth, K. *Bacillus* calmette-guerin versus chemotherapy for the intravesical treatment of patients with carcinoma in situ of the bladder: A meta-analysis of the published results of randomized clinical trials. J. Urol. 2005, 174, 86-91).

A more recent approach has focused on blocking the ability of certain proteins, called immune checkpoint proteins, to limit the strength and duration of immune responses. These proteins normally keep immune responses in check by preventing overly intense responses that might damage normal cells as well as abnormal cells; however, cancers expressing these proteins are capable of suppressing immune responses (See Menon, S.; Shin, S.; Dy, G.; Advances in Cancer Immunotherapy in Solid Tumors, Cancers 2016, 8(12), 106). Blocking the activity of immune checkpoint proteins increases the ability of immune effector cells to destroy cancer cells.

Terminology

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

In non-limiting embodiments, the CDK4/6 inhibitors, for example but not limited to Compound I, Compound II, Compound III, or Compound IV, chemotherapy, or checkpoint inhibitor can be used in a form that has at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into the CDK4/6 inhibitor, chemotherapy, or checkpoint inhibitor for use in the invention include isotopes of hydrogen, carbon, nitrogen, oxygen, phosphorous, fluorine, chlorine and iodine such as $^2H$, $^3H$, $^{11}C$, $^{13}C$, $^{14}C$, $^{15}N$, $^{18}F$ $^{31}P$, $^{32}P$, $^{35}S$, $^{36}Cl$, and $^{125}I$ respectively. In one non-limiting embodiment, isotopically labelled compounds can be used in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2H$) and tritium ($^3H$) may be used anywhere in described structures that achieves the desired result. Alternatively, or in addition, isotopes of carbon, e.g., $^{13}C$ and $^{14}C$, may be used.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

The CDK4/6 inhibitor for use in the present invention may form a solvate with solvents (including water). Therefore, in one non-limiting embodiment, the invention includes a solvated form of the compound. The term "solvate" refers to a molecular complex of a compound of the present invention (including a salt thereof) with one or more solvent molecules. Non-limiting examples of solvents are water, ethanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO. A solvate can be in a liquid or solid form.

As generally contemplated herein, the term hematopoietic stem and progenitor cell (HSPC) includes, but are not limited to, long term hematopoietic stem cells (LT-HSCs), short term hematopoietic stem cells (ST-HSCs), hematopoietic progenitor cells (HPCs), multipotent progenitors (MPPs), oligodendrocyte pre-progenitors (OPPs), monocyte progenitors, granulocyte progenitors, common myeloid progenitors (CMPs), common lymphoid progenitors (CLPs), granulocyte-monocyte progenitors (GMPs), granulocyte progenitors, monocyte progenitors, and megakaryocyte-erythroid progenitors (MEPs), megakaryocyte progenitors, erythroid progenitors, HSC/MPPs (CD45dim/CD34+/CD38−), OPPs (CD45dim/CD34+/CD38+), monocyte progenitors (CD45+/CD14+/CD11b+), granulocyte progenitors (CD45+/CD14−/CD11b+), erythroid progenitors (CD45−/CD71+), and megakaryocyte progenitors (CD45+/CD61+).

The term "immune effector cell" generally refers to an immune cell that performs one or more specific functions. Immune effector cells are known in the art and include for example, but are not limited to, T-cells, including Naïve T-cells, Memory T-cells, Activated T-cells (Thelper (CD4+) and Cytotoxic T cells (CD8+)), TH1 activated T-cells, TH2 activated T-cells, TH17 activated T-cells, Naïve B cells, Memory B cells, plasmablasts, dendritic cells, monocytes, myeloid derived suppressor cells (MDSCs), and natural killer (NK) cells.

The term "selective CDK4/6 inhibitor" as used in the context of the compounds described herein includes compounds that inhibit CDK4 activity, CDK6 activity, or both CDK4 and CDK6 activity at an $IC_{50}$ molar concentration at least about 50, 100, 200, 300, 400, 500, 1000, 1500, 1800, 2000, 5000 or 10,000 times less than the $IC_{50}$ molar concentration necessary to inhibit to the same degree of CDK2 activity in a standard phosphorylation assay.

The term "fast-acting CDK4/6 inhibitor" refers to a rapid onset of biological activity and short time to reach $C_{max}$ upon administration of the compound. For example, a fast-acting CDK4/6 inhibitor may have a $T_{max}$ less than about 2 hours, about 1 hour, about 30 minutes, or about 15 minutes or less following initiation of administration.

The term "short half-life CDK4/6 inhibitor" refers to a compound with a half-life of less than, for example, about 16 hours, 15 hours, 14 hours, 13 hours, 12 hours, 11 hours, 10 hours, 9 hours, or about less than 8 hours. In medical terms, the half-life of a drug is the time it takes for the plasma concentration of a drug to reach half of its original concentration.

The subject treated is typically a human subject, although it is to be understood the methods described herein are effective with respect to other animals, such as mammals and vertebrate species. More particularly, the term subject can include animals used in assays such as those used in preclinical testing including but not limited to mice, rats, monkeys, dogs, pigs and rabbits; as well as domesticated swine (pigs and hogs), ruminants, equine, poultry, felines, bovines, murines, canines, and the like.

In some embodiments, the term "CDK4/6-replication independent cancer" refers to a cancer that does not significantly require the activity of CDK4/6 for replication. Cancers of such type are often, but not always, characterized by (e.g., that has cells that exhibit) an increased level of CDK2 activity or by reduced expression of retinoblastoma tumor suppressor protein or retinoblastoma family member protein(s), such as, but not limited to p107 and p130. The increased level of CDK2 activity or reduced or deficient expression of retinoblastoma tumor suppressor protein or retinoblastoma family member protein(s) can be increased or reduced, for example, compared to normal cells. In some embodiments, the increased level of CDK2 activity can be associated with (e.g., can result from or be observed along with) MYC proto-oncogene amplification or overexpression. In some embodiments, the increased level of CDK2 activity can be associated with overexpression of Cyclin E1, Cyclin E2, or Cyclin A.

In some embodiments, the term "CDK4/6-replication dependent cancer" refers to a cancer that requires the activity of CDK4/6 for replication or proliferation, or which may be growth inhibited through the activity of a selective CDK4/6 inhibitor. Cancers and disorders of such type may be characterized by (e.g., that has cells that exhibit) the presence of a functional Retinoblastoma (Rb) protein. Such cancers and disorders are classified as being Rb-positive. Rb-positive abnormal cellular proliferation disorders, and variations of this term as used herein, refer to disorders or diseases caused by uncontrolled or abnormal cellular division which are characterized by the presence of a functional Retinoblastoma protein, which can include cancers.

CDK4/6 Inhibitors

The present invention is directed to the use of a specifically-timed administration of a CDK4/6-specific inhibitor in combination with a chemotherapeutic agent and an immune checkpoint inhibitor, for example a PD-1 inhibitor, PD-L1 inhibitor, or CTLA-4 inhibitor for treating a subject having a cancer.

The regulation of the cell cycle is governed and controlled by specific proteins, which are activated and deactivated mainly through phosphorylation/dephosphorylation processes in a precisely timed manner. The key proteins that coordinate the initiation, progression, and completion of cell-cycle program are cyclin dependent kinases (CDKs). Cyclin-dependent kinases belong to the serine-threonine protein kinase family. They are heterodimeric complexes composed of a catalytic kinase subunit and a regulatory cyclin subunit. CDK activity is controlled by association with their corresponding regulatory subunits (cyclins) and CDK inhibitor proteins (Cip & Kip proteins, INK4s), by their phosphorylation state, and by ubiquitin-mediated proteolytic degradation (see D. G. Johnson, C. L. Walker, Annu. Rev. Pharmacol. Toxicol 39 (1999) 295-312; D. O. Morgan, Annu. Rev. Cell Dev. Biol. 13 (1997) 261-291; C. J. Sherr, Science 274 (1996) 1672-1677; T. Shimamura et al., Bioorg. Med. Chem. Lett. 16 (2006) 3751-3754).

There are four CDKs that are significantly involved in cellular proliferation: CDK1, which predominantly regulates the transition from G2 to M phase, and CDK2, CDK4, and CDK6, which regulate the transition from G1 to S phase (Malumbres M, Barbacid M. Cell cycle, CDKs and cancer: a changing paradigm. Nat. Rev. Cancer 2009; 9(3):153-166). In early to mid G1 phase, when the cell is responsive to mitogenic stimuli, activation of CDK4-cyclin D and CDK6-cyclin D induces phosphorylation of the retinoblastoma protein (pRb). Phosphorylation of pRb releases the transcription factor E2F, which enters the nucleus to activate transcription of other cyclins which promote further progression of the cell cycle (see J. A. Diehl, Cancer Biol. Ther. 1 (2002) 226-231; C. J. Sherr, Cell 73 (1993) 1059-1065). CDK4 and CDK6 are closely related proteins with basically indistinguishable biochemical properties (see M. Malumbres, M. Barbacid, Trends Biochem. Sci. 30 (2005) 630-641).

Various pyrimidine-based agents have been developed for the treatment of hyperproliferative diseases. U.S. Pat. Nos. 8,822,683; 8,598,197; 8,598,186, 8,691,830, 8,829,102, 9,102,683, and 9,260,442 and corresponding WO 2012/061156 filed by Tavares and Strum and assigned to G1 Therapeutics describe a class of N-(heteroaryl)-pyrrolo[3,2-d]pyrimidin-2-amine cyclin dependent kinase inhibitors including those of the formula (with variables as defined therein):

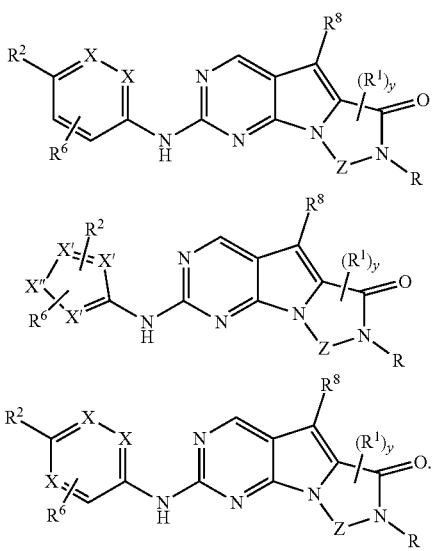

WO 2013/148748 (U.S. Ser. No. 61/617,657) titled "Lactam Kinase Inhibitors", WO 2013/163239 (U.S. Ser. No. 61/638,491) titled "Synthesis of Lactams" and WO 2015/061407 filed by Tavares and also assigned to G1 Therapeutics describes the synthesis of N-(heteroaryl)-pyrrolo[3,2-d]pyrimidin-2-amines and their use as lactam kinase inhibitors.

Other publications include the following: WO 2014/144326 filed by Strum et al. and assigned to G1 Therapeutics describes compounds and methods for protection of normal cells during chemotherapy using pyrimidine-based CDK4/6 inhibitors; WO 2014/144596 filed by Strum et al. and assigned to G1 Therapeutics describes compounds and methods for protection of hematopoietic stem and progenitor cells against ionizing radiation using pyrimidine-based CDK4/6 inhibitors; WO 2014/144847 filed by Strum et al. and assigned to G1 Therapeutics describes HSPC-sparing treatments of abnormal cellular proliferation using pyrimidine-based CDK4/6 inhibitors; WO 2014/144740 filed by Strum et al. and assigned to G1 Therapeutics describes highly active anti-neoplastic and anti-proliferative pyrimidine-based CDK 4/6 inhibitors; WO 2015/161285 filed by Strum et al. and assigned to G1 Therapeutics describes tricyclic pyrimidine-based CDK inhibitors for use in radioprotection; WO 2015/161287 filed by Strum et al. and assigned to G1 Therapeutics describes analogous tricyclic pyrimidine-based CDK inhibitors for the protection of cells during chemotherapy; WO 2015/161283 filed by Strum et al. and assigned to G1 Therapeutics describes analogous tricyclic pyrimidine-based CDK inhibitors for use in HSPC-sparing treatments of RB-positive abnormal cellular proliferation; WO 2015/161288 filed by Strum et al. and assigned to G1 Therapeutics describes analogous tricyclic pyrimidine-based CDK inhibitors for use as anti-neoplastic and anti-proliferative agents; WO 2016/040858 filed by Strum et al. and assigned to G1 Therapeutics describes the use of combinations of pyrimidine-based CDK4/6 inhibitors with other anti-neoplastic agents; WO 2016/040848 filed by Strum et al. and assigned to G1 Therapeutics describes compounds and methods for treating certain Rb-negative cancers with CDK4/6 inhibitors and topoisomerase inhibitors; WO 2016/126889 filed by Strum et al. and assigned to G1 Therapeutics describes the specific dosage formulations for the treatment of cancer with CDK4/6 inhibitors.

WO 2003/062236 identifies a series of 2-(pyridin-2-ylamino-pyrido[2,3]pyrimidin-7-ones for the treatment of Rb positive cancers that show selectivity for CDK4/6, including 6-acetyl-8-cyclopentyl-5-methyl-2-(5-piperazin-1-yl-pyridin-2-ylammino)-8H-pyrido-[2,3-d]-pyrimidin-7-one (PD0332991), which was given fast-track approval by the FDA and is currently sold as Ibrance® (Palbociclib) by Pfizer for the treatment of metastatic breast cancer.

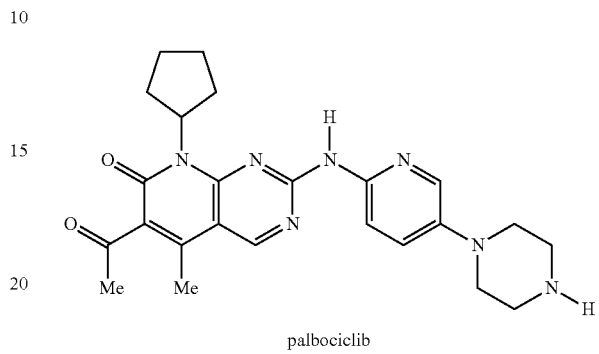

palbociclib

VanderWel et al. describe an iodine-containing pyrido[2,3-d]pyrimidine-7-one (CKIA) as a potent and selective CDK4 inhibitor (see VanderWel et al., J. Med. Chem. 48 (2005) 2371-2387).

WO 2010/020675 filed by Novartis AG describes pyrrolopyrimidine compounds as CDK inhibitors. WO 2011/101409 also filed by Novartis describes pyrrolopyrimidines with CDK 4/6 inhibitory activity. U.S. Pat. Nos. 8,324,225; 8,415,355; 8,685,980; 9,962,630; 9,193,732; and 9,416,136 filed by Novartis AG and Astex Therapeutics Limited describe pyrrrolopyrimidine compounds as CDK inhibitors, including 7-cyclopentyl-N,N-dimethyl-2-((5-(piperidin-4-yl)pyridin-2-yl)amino)-7H-pyrrolo[2,3-d]pyrimidine-6-carboxamide, which was approved by the FDA for the treatment of metastatic breast cancer and is currently sold as Kisqali® (ribociclib).

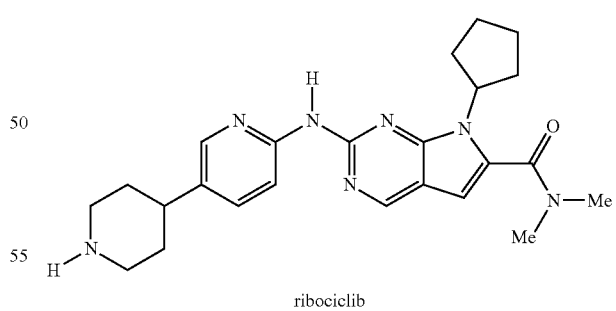

ribociclib

U.S. Pat. No. 7,855,211 described benzimidazole compounds that are useful as CDK4/6 inhibitors, including N-(5-((4-ethylpiperazin-1-yl)methyl)pyridin-2-yl)-5-fluoro-4-(4-fluoro-1-isopropyl-2-methyl-1H-benzo[d]imidazol-6-yl)pyrimidin-2-amine which was approved by the FDA for the treatment of certain types of breast cancer and is currently sold as Verzenio® (abemaciclib) by Eli Lilly and Company.

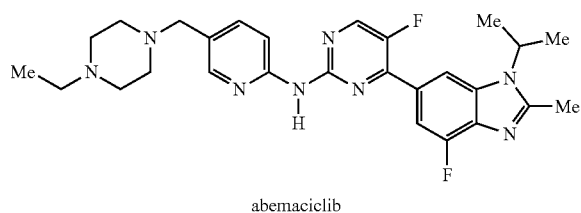 [SMILES: CCN1CCN(Cc2ccc(Nc3ncc(F)c(-c4cc(F)c5nc(C)n(C(C)C)c5c4)n3)nc2)CC1]

abemaciclib

Johnson et al. reported that pharmacological inhibition of CDK4/6 using the CDK4/6 inhibitors 6-acetyl-8-cyclopentyl-5-methyl-2-(5-piperazin-1-yl-pyridin-2-ylammino)-8H-pyrido-[2,3-d]-pyrimidin-7-one (PD0332991) and 2-bromo-12,13-dihydro-5H-indolo[2,3-a]pyrrolo[3,4]carbazole-5,6-dione (2BrIC) exhibited IR protective characteristics in CDK4/6-dependent cell lines. (Johnson et al. Mitigation of hematological radiation toxicity in mice through pharmacological quiescence induced by CDK4/6 inhibition. J Clin. Invest. 2010; 120(7): 2528-2536).

Compounds I, II, III, and IV can be prepared as previously described in WO 2014/144326, incorporated herein in its entirety.

In particular embodiments, as contemplated herein, the CDK4/6 inhibitor is selected from any known CDK4/6 inhibitor, for example trilaciclib, palbociclib, abemaciclib, and ribociclib. In one embodiment, the selective CDK4/6 inhibitor is a fast-acting, short half-life CDK4/6 inhibitor. In one embodiment, the fast acting, short half-life CDK4/6 inhibitor is selected from Compound I (trilaciclib), Compound II, Compound III, or Compound IV, or a pharmaceutically acceptable composition, salt, isotopic analog, or prodrug thereof. In certain embodiments, the CDK4/6 inhibitor is Compound I. In certain embodiments, the CDK4/6 inhibitor is Compound II. In certain embodiments, the CDK4/6 inhibitor is Compound III. In certain embodiments, the CDK4/6 inhibitor is Compound IV.

Immune Checkpoint Inhibitors

Immune checkpoint inhibitors for use in the methods described herein include, but are not limited to PD-1 inhibitors, PD-L1 inhibitors, PD-L2 inhibitors, CTLA-4 inhibitors, LAG-3 inhibitors, TIM-3 inhibitors, and V-domain Ig suppressor of T-cell activation (VISTA) inhibitors, or combinations thereof.

In one embodiment, the immune checkpoint inhibitor is a PD-1 inhibitor that blocks the interaction of PD-1 and PD-L 1 by binding to the PD-1 receptor, and in turn inhibits immune suppression. In one embodiment, the immune checkpoint inhibitor is a PD-1 immune checkpoint inhibitor selected from nivolumab (Opdivo®), pembrolizumab (Keytruda®), pidilizumab, AMP-224 (AstraZeneca and MedImmune), PF-06801591 (Pfizer), MEDI0680 (AstraZeneca), PDR001 (Novartis), REGN2810 (Regeneron), MGA012 (MacroGenics), BGB-A317 (BeiGene) SHR-12-1 (Jiangsu Hengrui Medicine Company and Incyte Corporation), TSR-042 (Tesaro), and the PD-L1/VISTA inhibitor CA-170 (Curis Inc.). In one embodiment, the PD-1 inhibitor is used in combination with the CDK4/6 inhibitor selected from Compound I or Compound II. In one embodiment, the CDK4/6 inhibitor is Compound I.

In one embodiment, the immune checkpoint inhibitor is the PD-1 immune checkpoint inhibitor nivolumab (Opdivo®) administered in an effective amount for the treatment of Hodgkin lymphoma, melanoma, non-small cell lung cancer, hepatocellular carcinoma, or ovarian cancer. Nivolumab has been FDA approved for the use of metastatic melanoma, non-small cell lung cancer, and renal cell carcinoma. In another aspect of this embodiment, the immune checkpoint inhibitor is the PD-1 immune checkpoint inhibitor pembrolizumab (Keytruda®) administered in an effective amount for the treatment of melanoma, non-small cell lung cancer, small cell lung cancer, head and neck cancer, or urothelial cancer. In an additional aspect of this embodiment, the immune checkpoint inhibitor is the PD-1 immune checkpoint inhibitor pidilizumab (Medivation) administered in an effective amount for refractory diffuse large B-cell lymphoma (DLBCL) or metastatic melanoma.

In one embodiment, the immune checkpoint inhibitor is a PD-L1 inhibitor that blocks the interaction of PD-1 and PD-L 1 by binding to the PD-L 1 receptor, and in turn inhibits immune suppression. PD-L1 inhibitors include, but are not limited to, atezolizumab, durvalumab, KN035CA-170 (Curis Inc.), and LY3300054 (Eli Lilly). In one embodiment, the PD-L1 inhibitor is used in combination with the CDK4/6 inhibitor selected from Compound I or Compound II. In one embodiment, the CDK4/6 inhibitor is Compound I. In one embodiment, the PD-L1 inhibitor is atezolizumab. In one embodiment, the PD-L1 inhibitor blocks the interaction between PD-L1 and CD80 to inhibit immune suppression.

In one embodiment, the immune checkpoint inhibitor is the PD-L1 immune checkpoint inhibitor atezolizumab (Tecentriq®) administered in an effective amount for the treatment of metastatic bladder cancer, metastatic melanoma, metastatic non-small cell lung cancer, or metastatic renal cell carcinoma. In another aspect of this embodiment, the immune checkpoint inhibitor is durvalumab (AstraZeneca and MedImmune) administered in an effective amount for the treatment of non-small cell lung cancer or bladder cancer. In yet another aspect of the embodiment, the immune checkpoint inhibitor is KN035 (Alphamab) administered in an effective amount for the treatment of PD-L 1 positive solid tumors. An additional example of a PD-L 1 immune checkpoint inhibitor is BMS-936559 (Bristol-Myers Squibb), although clinical trials with this inhibitor have been suspended as of 2015.

In one aspect of this embodiment, the immune checkpoint inhibitor is a CTLA-4 immune checkpoint inhibitor that binds to CTLA-4 and inhibits immune suppression. CTLA-4 inhibitors include, but are not limited to, ipilimumab, tremelimumab (AstraZeneca and MedImmune), AGEN1884 and AGEN2041 (Agenus). In one embodiment, the CTLA-4 inhibitor is used in combination with the CDK4/6 inhibitor selected from Compound I or Compound II. In one embodiment, the CDK4/6 inhibitor is Compound I.

In one embodiment, the CTLA-4 immune checkpoint inhibitor is ipilimumab (Yervoy®) administered in an effective amount for the treatment of metastatic melanoma, adjuvant melanoma, or non-small cell lung cancer. In one embodiment, the CTLA-4 inhibitor is used in combination with the CDK4/6 inhibitor selected from Compound I or Compound II. In one embodiment, the CDK4/6 inhibitor is Compound I.

In another embodiment, the immune checkpoint inhibitor is a LAG-3 immune checkpoint inhibitor. Examples of LAG-3 immune checkpoint inhibitors include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). In yet another aspect of this embodiment, the immune checkpoint inhibitor is a TIM-3 immune checkpoint inhibitor. A specific TIM-3 inhibitor includes, but is not limited to, TSR-022 (Tesaro).

Other immune checkpoint inhibitors for use in the invention described herein include, but are not limited to, B7-H3/CD276 immune checkpoint inhibitors such as MGA217, indoleamine 2,3-dioxygenase (IDO) immune checkpoint inhibitors such as Indoximod and INCB024360, killer immunoglobulin-like receptors (KIRs) immune checkpoint inhibitors such as Lirilumab (BMS-986015), carcinoembryonic antigen cell adhesion molecule (CEACAM) inhibitors (e.g., CEACAM-1, -3 and/or -5). Exemplary anti-CEACAM-1 antibodies are described in WO 2010/125571, WO 2013/082366 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In other embodiments, the anti-CEACAM antibody binds to CEACAM-5 as described in, e.g., Zheng et al. PLoS One. 2010 Sep. 2; 5(9). pii: e12529 (DOI:10:1371/journal.pone.0021146), or cross-reacts with CEACAM-1 and CEACAM-5 as described in, e.g., WO 2013/054331 and US 2014/0271618. Still other checkpoint inhibitors can be molecules directed to B and T lymphocyte attenuator molecule (BTLA), for example as described in Zhang et al., Monoclonal antibodies to B and T lymphocyte attenuator (BTLA) have no effect on in vitro B cell proliferation and act to inhibit in vitro T cell proliferation when presented in a cis, but not trans, format relative to the activating stimulus, Clin Exp Immunol. 2011 January; 163(1): 77-87.

Chemotherapeutic Agents

As contemplated herein, the specifically-timed administration of a selective, fast-acting, short half-life CDK4/6 inhibitor can be in combination with any standard chemotherapeutic agent treatment modality, in further combination with an immune checkpoint inhibitor.

In one embodiment, the chemotherapeutic agent is toxic to immune effector cells. In one embodiment the chemotherapeutic agent inhibits cell growth. In one embodiment, the cytotoxic chemotherapeutic agent administered is a DNA damaging chemotherapeutic agent. In one embodiment, the chemotherapeutic agent is a protein synthesis inhibitor, a DNA-damaging chemotherapeutic, an alkylating agent, a topoisomerase inhibitor, an RNA synthesis inhibitor, a DNA complex binder, a thiolate alkylating agent, a guanine alkylating agent, a tubulin binder, DNA polymerase inhibitor, an anticancer enzyme, RAC1 inhibitor, thymidylate synthase inhibitor, oxazophosphorine compound, integrin inhibitor such as cilengitide, camptothecin or homo-camptothecin, antifolate or a folate antimetabolite.

Cytotoxic Chemotherapeutic Agents

Cytotoxic, DNA-damaging chemotherapeutic agents tend to be non-specific and, particularly at high doses, toxic to normal, rapidly dividing cells such as HSPC and immune effector cells. As used herein the term "DNA-damaging" chemotherapy or chemotherapeutic agent refers to treatment with a cytostatic or cytotoxic agent (i.e., a compound) to reduce or eliminate the growth or proliferation of undesirable cells, for example cancer cells, wherein the cytotoxic effect of the agent can be the result of one or more of nucleic acid intercalation or binding, DNA or RNA alkylation, inhibition of RNA or DNA synthesis, the inhibition of another nucleic acid-related activity (e.g., protein synthesis), or any other cytotoxic effect. Such compounds include, but are not limited to, DNA damaging compounds that can kill cells. "DNA damaging" chemotherapeutic agents include, but are not limited to, alkylating agents, DNA intercalators, protein synthesis inhibitors, inhibitors of DNA or RNA synthesis, DNA base analogs, topoisomerase inhibitors, telomerase inhibitors, and telomeric DNA binding compounds.

For example, alkylating agents include alkyl sulfonates, such as busulfan, improsulfan, and piposulfan; aziridines, such as a benzodizepa, carboquone, meturedepa, and uredepa; ethylenimines and methylmelamines, such as altretamine, triethylenemelamine, triethylenephosphoramide, triethylenethiophosphoramide, and trimethylol melamine; nitrogen mustards such as chlorambucil, chlornaphazine, cyclophosphamide, estramustine, mechlorethamine, mechlorethamine oxide hydrochloride, melphalan, novembichine, phenesterine, prednimustine, trofosfamide, and uracil mustard; and nitroso ureas, such as carmustine, chlorozotocin, fotemustine, lomustine, nimustine, and ranimustine. Other DNA-damaging chemotherapeutic agents include daunorubicin, doxorubicin, idarubicin, epirubicin, mitomycin, and streptozocin. Chemotherapeutic antimetabolites include gemcitabine, mercaptopurine, thioguanine, cladribine, fludarabine phosphate, fluorouracil (5-FU), floxuridine, cytarabine, pentostatin, methotrexate, azathioprine, acyclovir, adenine β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxynorleucine, dideoxynucleosides, 5-fluorodeoxycytidine, 5-fluorodeoxyuridine, and hydroxyurea.

Chemotherapeutic protein synthesis inhibitors include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim.

Inhibitors of DNA synthesis, include alkylating agents such as dimethyl sulfate, nitrogen and sulfur mustards; intercalating agents, such as acridine dyes, actinomycins, anthracenes, benzopyrene, ethidium bromide, propidium diiodide-intertwining; and other agents, such as distamycin and netropsin. Topoisomerase inhibitors, such as irinotecan, teniposide, coumermycin, nalidixic acid, novobiocin, and oxolinic acid; inhibitors of cell division, including colcemide, mitoxantrone, colchicine, vinblastine, and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin, and streptolydigin also can be used as the DNA damaging compound.

In one embodiment the chemotherapeutic agent is a DNA complex binder such as camptothecin, or etoposide; a thiolate alkylating agent such as nitrosourea, BCNU, CCNU, ACNU, or fotesmustine; a guanine alkylating agent such as temozolomide, a tubulin binder such as vinblastine, vincristine, vinorelbine, vinflunine, cryptophycin 52, halichondrins, such as halichondrin B, dolastatins, such as dolastatin 10 and dolastatin 15, hemiasterlins, such as hemiasterlin A and hemiasterlin B, colchicine, combrestatins, 2-methoxyestradiol, E7010, paclitaxel, docetaxel, epothilone, discodermolide; a DNA polymerase inhibitor such as cytarabine; an anticancer enzyme such as asparaginase; a Rac1 inhibitor such as 6-thioguanine; a thymidylate synthase inhibitor such as capecitabine or 5-FU; a oxazophosphorine compound such as Cytoxan; a integrin inhibitor such as cilengitide; an antifolate such as pralatrexate; a folate antimetabolite such as pemetrexed, or a camptothecin or homocamptothecin such as diflomotecan.

In one embodiment the topoisomerase inhibitor is a type I inhibitor. In another embodiment the topoisomerase inhibitor is a type II inhibitor.

Other DNA-damaging chemotherapeutic agents whose toxic effects can be mitigated by the presently disclosed selective CDK4/6 inhibitors include, but are not limited to, cisplatin, hydrogen peroxide, carboplatin, procarbazine, ifosfamide, bleomycin, plicamycin, taxol, transplatinum, thiotepa, oxaliplatin, and the like, and similar acting-type agents. In one embodiment, the DNA damaging chemotherapeutic agent is selected from the group consisting of cisplatin, carboplatin, camptothecin, and etoposide.

Other suitable chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. General anticancer pharmaceutical agents include: Vincristine (Oncovin®), liposomal vincristine (Marqibo®), doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Prednisone, and Dexamethasone (Decadron). Examples of additional suitable chemotherapeutic agents include but are not limited to 5-fluorouracil, dacarbazine, alkylating agents, anthramycin (AMC)), anti-mitotic agents, cis-dichlorodiamine platinum (II) (DDP) cisplatin), diamino dichloro platinum, anthracyclines, antibiotics, antimetabolites, asparaginase, BCG live (intravesical), bleomycin sulfate, calicheamicin, cytochalasin B, dactinomycin (formerly actinomycin), daunorubicin HCl, daunorubicin citrate, denileukin diftitox, dihydroxy anthracin dione, Docetaxel, doxorubicin HCl, *E. coli* L-asparaginase, *Erwinia* L-asparaginase, etoposide citrovorum factor, etoposide phosphate, gemcitabine HCl, idarubicin HCl, interferon α-2b, irinotecan HCl, maytansinoid, mechlorethamine HCl, melphalan HCl, mithramycin, mitomycin C, mitotane, paclitaxel, polifeprosan 20 with carmustine implant, procarbazine HCl, streptozotocin, teniposide, thiotepa, topotecan HCl, valrubicin, vinblastine sulfate, vincristine sulfate, and vinorelbine tartrate.

Additional cytotoxic chemotherapeutic agents for use with the present invention include: epirubicin, abraxane, taxotere, epothilone, tafluposide, vismodegib, azacytidine, doxifluridine, vindesine, and vinorelbine.

In one embodiment the chemotherapeutic agent is not an aromatase inhibitor. In one embodiment the chemotherapeutic agent is not a steroid. In one embodiment the chemotherapeutic agent is not a BCR-ABL inhibitor.

In one embodiment the chemotherapeutic agent is a DNA complex binder. In one embodiment the chemotherapeutic agent is a tubulin binder. In one embodiment the chemotherapeutic agent is an alkylating agent. In one embodiment the chemotherapeutic agent is a thiolate alkylating agent.

Additional Chemotherapeutic Agents

Additional chemotherapeutic agents that may be used as described herein may include 2-methoxyestradiol or 2ME2, finasunate, etaracizumab (MEDI-522), HLL1, huN901-DM1, atiprimod, saquinavir mesylate, ritonavir, nelfinavir mesylate, indinavir sulfate, plitidepsin, P276-00, tipifarnib, lenalidomide, thalidomide, pomalidomide, simvastatin, and celecoxib. Chemotherapeutic agents useful in the present invention include, but are not limited to, Trastuzumab (Herceptin®), Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Targretin®), Alitretinoin (Panretin®), Tretinoin (Vesanoid®), Carfilzomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

Additional chemotherapeutic agents contemplated include, but are not limited to, a calcineurin inhibitor, e.g. a cyclosporin or an ascomycin, e.g. Cyclosporin A (Neoral®), FK506 (tacrolimus), pimecrolimus, a mTOR inhibitor, e.g. rapamycin or a derivative thereof, e.g. Sirolimus (Rapamune®), Everolimus (Certican®), temsirolimus, zotarolimus, biolimus-7, biolimus-9, a rapalog, e.g. ridaforolimus, campath 1H, a S11$^3$ receptor modulator, a dual mTORC1 and mTORC2 inhibitor, eg. Vistusertib (AZD2014), e.g. fingolimod or an analogue thereof, an anti IL-8 antibody, mycophenolic acid or a salt thereof, e.g. sodium salt, or a prodrug thereof, e.g. Mycophenolate Mofetil (CellCept®), OKT3 (Orthoclone OKT3®), Prednisone, ATGAM®, Thymoglobulin®, Brequinar Sodium, OKT4, T10B9.A-3A, 33B3.1, 15-deoxyspergualin, tresperimus, Leflunomide Arava®, anti-CD25, anti-IL2R, Basiliximab (Simulect®), Daclizumab (Zenapax®), mizoribine, dexamethasone, ISAtx-247, SDZ ASM 981 (pimecrolimus, Elidel®), Abatacept, belatacept, LFA31g, etanercept (sold as Enbrel® by ImmuneXcite), adalimumab (Humira®), infliximab (Remicade®), an anti-LFA-1 antibody, natalizumab (Antegren®), Enlimomab, gavilimomab, Golimumab, antithymocyte immunoglobulin, siplizumab, Alefacept, efalizumab, Pentasa, mesalazine, asacol, codeine phosphate, benorylate, fenbufen, naprosyn, diclofenac, etodolac, indomethacin, dasatinib (Sprycel®) nilotinib (Tasigna®), bosutinib (Bosulif®), Imatinib mesylate (Gleevec®) and ponatinib (Iclusig™) amifostine, dolasetron mesylate, dronabinol, epoetin-α, etidronate, filgrastim, fluconazole, goserelin acetate, gramicidin D, granisetron, leucovorin calcium, lidocaine, Mesna, ondansetron HCl, pilocarpine HCl, porfimer sodium, vatalanib, 1-dehydrotestosterone, allopurinol sodium, Betamethasone, sodium phosphate and betamethasone acetate, calcium leucovorin, conjugated estrogens, Dexrazoxane, Dibromomannitol, esterified estrogens, estradiol, estramustine phosphate sodium, ethinyl estradiol, flutamide, folinic acid, glucocorticoids, leuprolide acetate, levamisole HCl, medroxyprogesterone acetate, megestrol acetate, methyltestosterone, nilutamide, octreotide acetate, pamidronate disodium, procaine, propranolol, testolactone, tetracaine, toremifene citrate, and sargramostim.

In one embodiment the chemotherapeutic agent is an estrogen receptor ligands such as tamoxifen, raloxifene, fulvestrant, anordrin, bazedoxifene, broparestriol, chlorotrianisene, clomiphene citrate, cyclofenil, lasofoxifene, ormeloxifene, or toremifene; an androgen receptor ligand such as bicalutamide, enzalutamide, apalutamide, cyproterone acetate, chlormadinone acetate, spironolactone, canrenone, drospirenone, ketoconazole, topilutamide, abiraterone acetate, or cimetidine; an aromatase inhibitor such as letrozole, anastrozole, or exemestane; an anti-inflammatory such as prednisone; an oxidase inhibitor such as allopurinol; an anticancer antibody; an anticancer monoclonal antibody; an antibody against CD40 such as lucatumumab or dacetuzumab; an antibody against CD20 such as rituximab; an antibody that binds CD52 such as alemtuzumab; an antibody that binds integrin such as volociximab or natalizumab; an antibody against interleukin-6 receptor such as tocilizumab; an interleukin-2 memetic such as aldesleukin; an antibody that targets IGF1 like figitumumab; an antibody that targets DR4 such as mapatumumab; an antibody that targets TRAIL-R2 such as lexatumumab or dulanermin; a fusion protein such as atacicept; a B cell inhibitor such as atacicept; a proteasome inhibitor such as carfilzomib, bortezomib, or marizomib; a HSP90 inhibitor such as tanespimycin; a HDAC inhibitor such as vorinostat, belinostat or panobinostat; a MAPK ligand such as talmapimod; a PKC inhibitor such as enzastaurin; a HER2 receptor ligand such as trastuzumab, lapatinib, or pertuzumab; an EGFR inhibitor such as gefitinib, erlotinib, cetuximab, panitumumab, or vandetanib; a natural product such as romidepsin; a retinoid such as bexarotene, tretinoin, or alitretinoin; a receptor tyrosine kinase (RTK) inhibitor such as sunitinib, regorafenib, or pazopanib; or a VEGF inhibitor such as ziv-aflibercept, bevacizumab or dovitinib.

In one embodiment, the combinations of a CDK4/6 inhibitor, chemotherapeutic agent, and immune checkpoint inhibitor is further combined with the use of hematopoietic growth factors including, but not limited to, granulocyte colony stimulating factor (G-CSF, for example, sold as Neupogen® (filgrastim), Neulasta® (peg-filgrastim), or lenograstim), granulocyte-macrophage colony stimulating factor (GM-CSF, for example sold as molgramostim and sargramostim (Leukine®)), M-CSF (macrophage colony stimulating factor), Thrombopoietin (megakaryocyte growth development factor (MGDF), for example sold as Romiplostim® and Eltrombopag®) interleukin (IL)-12, interleukin-3, interleukin-11 (adipogenesis inhibiting factor or oprelvekin), SCF (stem cell factor, steel factor, kit-ligand, or KL) and erythropoietin (EPO), and their derivatives (sold as for example epoetin-α as Darbepoetin, Epocept, Nanokine, Epofit, Epogen, Eprex, and Procrit; epoetin-β sold as for example NeoRecormon, Recormon and Micera), epoetin-delta (sold as for example Dynepo), epoetin-omega (sold as for example Epomax), epoetin zeta (sold as for example Silapo and Retacrit) as well as for example Epocept, Epotrust, Erypro Safe, Repoitin, Vintor, Epofit, Erykine, Wepox, Espogen, Relipoietin, Shanpoietin, Zyrop and EPIAO). In one embodiment, Compound I, Compound II, Compound III, or Compound IV is administered prior to administration of the hematopoietic growth factor. In one embodiment, the hematopoietic growth factor administration is timed so that the CDK4/6 inhibitor's effect on HSPCs has dissipated. In one embodiment, the growth factor is administered at least 20 hours after the administration of the CDK4/6 inhibitor.

Additional chemotherapeutic agents contemplated herein, particularly in the treatment of abnormal tissue of the female reproductive system such as breast, ovarian, endometrial, or uterine cancer include an estrogen inhibitor including but not limited to a SERM (selective estrogen receptor modulator), a SERD (selective estrogen receptor degrader), a complete estrogen receptor degrader, or another form of partial or complete estrogen antagonist. Partial anti-estrogens like raloxifene and tamoxifen retain some estrogen-like effects, including an estrogen-like stimulation of uterine growth, and also, in some cases, an estrogen-like action during breast cancer progression which actually stimulates tumor growth. In contrast, fulvestrant, a complete anti-estrogen, is free of estrogen-like action on the uterus and is effective in tamoxifen-resistant tumors. Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703,810, as well as US 2015/0005286, WO 2014/205136, and WO 2014/205138. Additional non-limiting examples of anti-estrogen compounds include: SERMS such as anordrin, bazedoxifene, broparestriol, clomiphene citrate, cyclofenil, lasofoxifene, ormeloxifene, raloxifene, tamoxifen, toremifene, and fulvestrant; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, delmadinone acetate, dydrogesterone, medroxyprogesterone acetate, megestrol acetate, nomegestrol acetate, norethisterone acetate, progesterone, and spironolactone.

Additional chemotherapeutic agents contemplated herein, particularly in the treatment of abnormal tissue of the male reproductive system such as prostate or testicular cancer, include, but are not limited to, an androgen (such as testosterone) inhibitor including but not limited to a selective androgen receptor modulator, a selective androgen receptor degrader, a complete androgen receptor degrader, or another form of partial or complete androgen antagonist. In one embodiment, the prostate or testicular cancer is androgen-resistant. Non-limiting examples of anti-androgen compounds are provided in WO 2011/156518 and U.S. Pat. Nos. 8,455,534 and 8,299,112. Additional non-limiting examples of anti-androgen compounds include: chlormadinone acetate, spironolactone, canrenone, drospirenone, ketoconazole, topilutamide, abiraterone acetate, and cimetidine.

The chemotherapeutic agent may include a kinase inhibitor, including but not limited to a phosphoinositide 3-kinase (PI3K) inhibitor, a Bruton's tyrosine kinase (BTK) inhibitor, or a spleen tyrosine kinase (Syk) inhibitor, or a combination thereof.

PI3k inhibitors are well known. Examples of PI3 kinase inhibitors include but are not limited to Wortmannin, demethoxyviridin, perifosine, idelalisib, pictilisib, Palomid 529, ZSTK474, PWT33597, CUDC-907, and AEZS-136, duvelisib, GS-9820, GDC-0032 (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl]oxy}phosphonium)), BYL-719 ((2 S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide), TGX-221 ((±)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-(0-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-149H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methyl sulfonyl)-1-piperazinyl]methyl]-4-(4-morpholinyl)thieno[3,2-d]pyrimidine), GDC-0980 ((S)-1-(4-((2-(2- aminopyrimidin-5-yl)-7-methyl-4-morpholinothieno[3,2-d]pyrimidin-6 yl)methyl)piperazin-1-yl)-2-hydroxypropan-1-one (also known as RG7422)), SF1126 ((8S,14 S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3,5-triazin-2-yl)phenyl]urea), LY3023414, BEZ235 (2-Methyl-2-{4-[3-methyl-2-oxo-8-(quinolin-3-yl)-2,3-dihydro-1H-imidazo[4,5-c]quinolin-1-yl]phenyl}propanenitrile), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis(prop-2-enyl)amino]methylidene]-5-hydroxy-9-(methoxymethyl)-9a,11a-dimethyl-1,4,7-trioxo-2,3,3a,9,10,11-hexahydroindeno[4,5h]isochromen-10-yl] acetate (also known as sonolisib)), and the structure described in WO2014/071109 having the formula:

BTK inhibitors are well known. Examples of BTK inhibitors include ibrutinib (also known as PCI-32765)(Imbruvica™) (1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl)phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g]quinoxalin-6(5H)-one), GDC-0834 ((R)—N-(3-(6-((4-(1,4-dimethyl-3-oxopiperazin-2-yl)phenyl)amino)-4-methyl-5-oxo-4, 5-dihydropyrazin-2-yl)-2-methylphenyl)-4, 5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4, 5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino)pyrimidine-5-carboxamide hydrochloride), QL-47 (1-(1-acryloylindolin-6-yl)-9-(1-methyl-1H-pyrazol-4-yl)benzo[h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference.

Syk inhibitors are well known, and include, for example, Cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a]pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4,5-trimethoxyphenyl)amino)pyrimidin-4-yl)amino)-2,2-dimethyl-3-oxo-2H-pyrido[3,2-b][1,4]oxazin-4 (3H)-yl)methyl phosphate), BAY 61-3606 (2-(7-(3,4-Dimethoxyphenyl)-imidazo[1,2-c]pyrimidin-5-ylamino)-nicotinamide HCl), R09021 (6-[(1R,2S)-2-Aminocyclohexylamino]-4-(5,6-dimethyl-pyridin-2-ylamino)-pyridazine-3-carboxylic acid amide), imatinib (Gleevec; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R,2 S)-2-aminocyclohexyl)amino)-4-(m-tolylamino)pyrimidine-5-carboxamide), PRT-062607 (4-((3-(2H-1,2,3-triazol-2-yl)phenyl)amino)-2-(((1R,2 S)-2-aminocyclohexyl)amino)pyrimidine-5-carboxamide hydrochloride), R112 (3,3'-((5-fluoropyrimidine-2,4-diyl)bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4]oxazin-3(4H)-one), YM193306(see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, J. Med. Chem. 2012, 55, 3614-3643 incorporated in its entirety herein).

The chemotherapeutic agent can also be a B-cell lymphoma 2 (Bcl-2) protein inhibitor. BCL-2 inhibitors are known in the art, and include, for example, ABT-199 (4-[4-[[2-(4-Chlorophenyl)-4,4-dimethylcyclohex-1-en-i-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenyl sulfanylbutan-2-yl]amino]-3- nitrophenyl]sulfonylbenzamide), ABT-263 ((R)-4-(4-((4'-chloro-4,4-dimethyl-3,4,5,6-tetrahydro-[1, 1'-biphenyl]-2-yl)methyl)piperazin-1-yl)-N-((4-((4-morpholino-1-(phenylthio)butan-2-yl)amino)-3 ((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl)phenyl]sulfonyl]phenyl]-2,3,4-trihydroxy-5-[[2-(1-methylethyl)phenyl]methyl]benzamide), Apogossypolone (ApoG2), or G3139 (Oblimersen).

Additional chemotherapeutic agents for use in the methods contemplated herein include, but are not limited to, midazolam, MEK inhibitors, RAS inhibitors, ERK inhibitors, ALK inhibitors, HSP inhibitors (for example, HSP70 and HSP 90 inhibitors, or a combination thereof), RAF inhibitors, apoptotic compounds, topoisomerase inhibitors, AKT inhibitors, including but not limited to, MK-2206, GSK690693, Perifosine, (KRX-0401), GDC-0068, Triciribine, AZD5363, Honokiol, PF-04691502, and Miltefosine, or FLT-3 inhibitors, including but not limited to, P406, Dovitinib, Quizartinib (AC220), Amuvatinib (MP-470), Tandutinib (MLN518), ENMD-2076, and KW-2449, or combinations thereof. Examples of MEK inhibitors include but are not limited to trametinib/GSKl1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinib (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2, 3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2 yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide). Examples of RAS inhibitors include but are not limited to Reolysin and siGl2D LODER. Examples of ALK inhibitors include but are not limited to Crizotinib, AP26113, and LDK378. HSP inhibitors include but are not limited to Geldanamycin or 17-N-Allylamino-17-demethoxygeldanamycin (17AAG), and Radicicol.

Known ERK inhibitors include SCH772984 (Merck/Schering-Plough), VTX-11e (Vertex), DEL-22379, Ulixertinib (BVD-523, VRT752271), GDC-0994, FR 180204, XMD8-92, and ERK5-IN-1.

Raf inhibitors are well known, and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carb oxamide; 4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl]pyridin-4-yl]oxy-N-[4-(trifluoromethyl)phenyl]benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), and Sorafenib N-Oxide (4-[4-[[[[4-Chloro-3 (trifluoroMethyl)phenyl]aMino]carbonyl]aMino]phenoxy]-N-Methyl-2pyridinecarboxaMide 1-Oxide).

Known topoisomerase I inhibitors useful in the present invention include (S)-10-[(dimethylamino)methyl]-4-ethyl-4,9-dihydroxy-1H-pyrano[3',4':6,7]indolizino[1,2-b]quinoline-3,14(4H, 12H)-dione monohydrochloride (topotecan), (S)-4-ethyl-4-hydroxy-1H-pyrano[3',4':6,7]indolizino[1,2-b]quinoline-3,14-(4H,12H)-dione (camptothecin), (1S,9S)-1-Amino-9-ethyl-5-fluoro-1,2,3,9,12,15-hexahydro-9-hydroxy-4-methyl-1 OH, 13H-benzo(de)pyrano(3',4':6,7)indolizino(1,2-b)quinoline-10,13-dione (exatecan), (7-(4-methylpiperazinomethylene)-10,11-ethylenedioxy-20(S)-camptothecin (lurtotecan), or (S)-4,11-diethyl-3,4,12,14-tetrahydro-4-hydroxy-3,14-dioxo 1H-pyrano[3',4':6,7]-indolizino[1,2-b]quinolin-9-yl-[1,4'bipiperidine]-1'-carboxylate (irinotecan), (R)-5-ethyl-9,10-difluoro-5-hydroxy-4,5-dihydrooxepino[3',4':6,7]indolizino[1,2-b]quinoline-3,15(1H, 13H)-dione (diflomotecan), (4S)-11-((E)-((1,1-Dimethylethoxy)imino)methyl)-4-ethyl-4-hydroxy-1,12-dihydro-14H-pyrano(3',4':6,7)indolizino(1,2-b)quinoline-3,14(4H)-dione (gimatecan), (S)-8-ethyl-8-hydroxy-15-((4-methylpiperazin-1-yl)methyl)-11,14-dihydro-2H-[1,4]dioxino[2,3-g]pyrano[3',4':6,7]indolizino[1,2-b]quinoline-9,12(3H,8H)-dione (lurtotecan), (4S)-4-Ethyl-4-hydroxy-11-[2-[(1-methylethyl)amino]ethyl]-1H-pyrano[3?,4?:6,7]indolizino[1,2-b]quinoline-3,14(4H, 12H)-dione (belotecan), 6-((1,3-dihydroxypropan-2-yl)amino)-2,10-dihydroxy-12-((2R,3R,4S,5 S,6R)-3,4,5-trihydroxy-6-(hydroxymethyl)tetrahydro-2H-pyran-2-yl)-12,13-dihydro-5H-indolo[2,3-a]pyrrolo[3,4-c]carbazole-5,7(6H)-dione (edotecarin), 8,9-dimethoxy-5-(2-N,N-dimethylaminoethyl)-2,3-methylenedioxy-5H-dibenzo(c,h)(1,6)naphthyridin-6-one (topovale), benzo[6,7]indolizino[1, 2-b]quinolin-11(13H)-one (rosettacin), (S)-4-ethyl-4-hydroxy-11-(2-(trimethylsilyl)ethyl)-1H-pyrano[3',4':6,7]indolizino[1,2-b]quinoline-3,14(4H, 12H)-dione (cositecan), tetrakis{(4S)-9-[([1,4'-bipiperidinyl]-11'-carbonyl)oxy]-4,11-diethyl-3,14-dioxo-3,4,12,14-tetrahydro-1H-pyrano[3',4':6,7]indolizino[1,2-b]quinolin-4-yl}N,N',N'',N''''-{methanetetrayltetrakis[methylenepoly(oxyethylene)oxy(1-oxoethylene)]}tetraglycinate tetrahydrochloride (etirinotecan pegol), 10-hydroxy-camptothecin (HOCPT), 9-nitrocamptothecin (rubitecan), SN38 (7-ethyl-10-hydroxycamptothecin), and 10-hydroxy-9-nitrocamptothecin (CPT109), (R)-9-chloro-5-ethyl-5-hydroxy-10-methyl-12-((4-methylpiperidin-1-yl)methyl)-4,5-dihydrooxepino[3',4': 6,7]indolizino[1,2-b]quinoline-3,15(1H, 13H)-dione (elmotecan).

In one embodiment, the chemotherapeutic agent is not an aromatase inhibitor. In one embodiment, the chemotherapeutic agent is not an estrogen or androgen receptor agonist or antagonist.

Growth Factors

In one embodiment, the combinations of a CDK4/6 inhibitor, chemotherapeutic agent, and checkpoint inhibitor is further combined with the use of hematopoietic growth factors including, but not limited to, granulocyte colony stimulating factor (G-CSF, for example, sold as Neupogen (filgrastim), Neulasta (peg-filgrastim), or lenograstim), granulocyte-macrophage colony stimulating factor (GM-CSF, for example sold as molgramostim and sargramostim (Leukine)), M-CSF (macrophage colony stimulating factor), Thrombopoietin (megakaryocyte growth development factor (MGDF), for example sold as Romiplostim and Eltrombopag) interleukin (IL)-12, interleukin-3, interleukin-11 (adipogenesis inhibiting factor or oprelvekin), SCF (stem cell factor, steel factor, kit-ligand, or KL) and erythropoietin (EPO), and their derivatives (sold as for example epoetin-α as Darbepoetin, Epocept, Nanokine, Epofit, Epogen, Eprex, and Procrit; epoetin-β sold as for example NeoRecormon, Recormon and Micera), epoetin-delta (sold as for example Dynepo), epoetin-omega (sold as for example Epomax), epoetin zeta (sold as for example Silapo and Retacrit) as well as for example Epocept, Epotrust, Erypro Safe, Repoitin, Vintor, Epofit, Erykine, Wepox, Espogen, Relipoietin, Shanpoietin, Zyrop and EPIAO). In one embodiment, Compound I, Compound II, Compound III, or Compound IV is administered prior to administration of the hematopoietic growth factor. In one embodiment, the hematopoietic growth factor administration is timed so that the CDK4/6 inhibitor's effect on HSPCs has dissipated. In one embodiment, the growth factor is administered at least 20 hours after the administration of the CDK4/6 inhibitor.

Cancer or Tumor Types

As contemplated herein, the specifically-timed use of a CDK4/6 inhibitor in combination with a chemotherapeutic agent and an immune checkpoint inhibitor can be used in the treatment of a subject having a cancer or tumor. In one embodiment, the cancer or tumor is a CDK4/6-replication dependent cancer or tumor. In one embodiment, the cancer or tumor is a CDK4/6-replication independent cancer or tumor. In one embodiment, the cancer is a solid cancer or tumor. In one embodiment, the cancer or tumor is a non-solid cancer or tumor. In one embodiment, the solid tumor expresses PD-L 1. In one embodiment, the cancer is a hematological cancer. In certain aspects, the cancer is a leukemia, lymphoma, or multiple myeloma.

In particular, the methods described herein can be used to treat a subject with a Rb-positive cancer or other Rb-positive abnormal cellular proliferative disorder. In some embodiments, the cancer or cellular proliferation disorder is a CDK4/6-replication dependent cancer or cellular proliferation disorder, which refers to a cancer or cellular proliferation disorder that requires the activity of CDK4/6 for replication or proliferation, or which may be growth inhibited through the activity of a CDK4/6 inhibitor. Cancers and disorders of such type can be characterized by (e.g., that has cells that exhibit) the presence of a functional Retinoblastoma protein. Such cancers and disorders are classified as being Rb-positive. Rb-positive abnormal cellular proliferation disorders, and variations of this term as used herein, refer to disorders or diseases caused by uncontrolled or abnormal cellular division which are characterized by the presence of a functional Retinoblastoma protein, which can include cancers. In one aspect of the present invention, the use of CDK4/6 inhibitors in combination with additional therapeutic agents and methods described herein can be used to treat a non-cancerous Rb-positive abnormal cellular proliferation disorder. Examples of such disorders may include non-malignant lymphoproliferation, non-malignant breast neoplasms, psoriasis, arthritis, dermatitis, pre-cancerous colon lesions or pulps, angiogenesis disorders, immune mediated and non-immune mediated inflammatory diseases, arthritis, age-related macular degeneration, diabetes, and other non-cancerous or benign cellular proliferation disorders.

Targeted cancers suitable for administration of a compound described herein may include Rb-positive: estrogen-receptor positive cancer, HER2-negative advanced breast cancer, late-line metastatic breast cancer, liposarcoma, non-small cell lung cancer, liver cancer, ovarian cancer, glioblastoma, refractory solid tumors, retinoblastoma positive breast cancer as well as retinoblastoma positive endometrial, vaginal and ovarian cancers and lung and bronchial cancers, adenocarcinoma of the colon, adenocarcinoma of the rectum, central nervous system germ cell tumors, teratomas, estrogen receptor-negative breast cancer, estrogen receptor-positive breast cancer, familial testicular germ cell tumors, HER2-negative breast cancer, HER2-positive breast cancer, male breast cancer, ovarian immature teratomas, ovarian mature teratoma, ovarian monodermal and highly specialized teratomas, progesterone receptor-negative breast cancer, progesterone receptor-positive breast cancer, recurrent breast cancer, recurrent colon cancer, recurrent extragonadal germ cell tumors, recurrent extragonadal non-seminomatous germ cell tumor, recurrent extragonadal seminomas, recurrent malignant testicular germ cell tumors, recurrent melanomas, recurrent ovarian germ cell tumors, recurrent rectal cancer, stage III extragonadal non-seminomatous germ cell tumors, stage III extragonadal seminomas, stage III malignant testicular germ cell tumors, stage III ovarian germ cell tumors, stage IV breast cancers, stage IV colon cancers, stage IV extragonadal non-seminomatous germ cell tumors, stage IV extragonadal seminoma, stage IV melanomas, stage IV ovarian germ cell tumors, stage IV rectal cancers, testicular immature teratomas, testicular mature teratomas. In particular embodiments, the targeted cancers included estrogen-receptor positive, HER2-negative advanced breast cancer, late-line metastatic breast cancer, liposarcoma, non-small cell lung cancer, liver cancer, ovarian cancer, glioblastoma, refractory solid tumors, retinoblastoma positive breast cancer as well as retinoblastoma positive endometrial, vaginal and ovarian cancers and lung and bronchial cancers, metastatic colorectal cancer, metastatic melanoma with CDK4 mutation or amplification, or cisplatin-refractory, unresectable germ cell tumors.

In one embodiment, the subject has bladder cancer, gastroesophageal cancer, soft tissue sarcoma, cholangio/gall bladder cancer, ovarian cancer, or cervical cancer.

In one embodiment, the Rb-positive cancer is selected from an Rb-positive carcinoma, sarcoma, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers.

In one embodiment, the Rb-positive cancer is selected from the group consisting of Rb-positive: fibrosarcoma, myxosarcoma, chondrosarcoma, osteosarcoma, chordoma, malignant fibrous histiocytoma, hemangiosarcoma, angiosarcoma, lymphangiosarcoma, Mesothelioma, leiomyosarcoma, rhabdomyosarcoma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, Islet cell carcinoma, malignant carcinoid, malignant paraganglioma, melanoma, Merkel cell neoplasm, cystosarcoma phylloide, salivary cancers, thymic carcinomas, bladder cancer, and Wilms tumor.

In more embodiments, the Rb-positive cancer or disorder includes a blood disorder or a hematologic malignancy, including, but not limited to, myeloid disorder, lymphoid disorder, leukemia, lymphoma, myelodysplastic syndrome (MDS), myeloproliferative disease (MPD), mast cell disorder, and myeloma (e.g., multiple myeloma), among others. Abnormal proliferation of T-cells, B-cells, and/or NK-cells can result in a wide range of diseases such as cancer, proliferative disorders and inflammatory/immune diseases. A host, for example a human, afflicted with any of these disorders can be treated with an effective amount of a combination as described herein to achieve a decrease in symptoms (a palliative agent) or a decrease in the underlying disease (a disease modifying agent).

Examples include T-cell or NK-cell lymphoma, for example, but not limited to: peripheral T-cell lymphoma; anaplastic large cell lymphoma, for example anaplastic lymphoma kinase (ALK) positive, ALK negative anaplastic large cell lymphoma, or primary cutaneous anaplastic large cell lymphoma; angioimmunoblastic lymphoma; cutaneous T-cell lymphoma, for example mycosis fungoides, Sézary syndrome, primary cutaneous anaplastic large cell lymphoma, primary cutaneous CD30+ T-cell lymphoproliferative disorder; primary cutaneous aggressive epidermotropic CD8+ cytotoxic T-cell lymphoma; primary cutaneous gamma-delta T-cell lymphoma; primary cutaneous small/medium CD4+ T-cell lymphoma, and lymphomatoid papulosis; Adult T-cell Leukemia/Lymphoma (ATLL); Blastic NK-cell Lymphoma; Enteropathy-type T-cell lymphoma; Hematosplenic gamma-delta T-cell Lymphoma; Lymphoblastic Lymphoma; Nasal NK/T-cell Lymphomas; Treatment-related T-cell lymphomas; for example lymphomas that appear after solid organ or bone marrow transplantation; T-cell prolymphocytic leukemia; T-cell large granular lymphocytic leukemia; Chronic lymphoproliferative disorder of NK-cells; Aggressive NK cell leukemia; Systemic EBV+ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like T-cell lymphoma.

In one embodiment, the methods described herein can be used to treat a host, for example a human, with a lymphoma or lymphocytic or myelocytic proliferation disorder or abnormality. For example, the methods as described herein can be administered to a host with a Hodgkin Lymphoma or a Non-Hodgkin Lymphoma. For example, the host can have a Non-Hodgkin Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; or Waldenstrom's Macroglobulinemia.

Alternatively, the methods described herein can be used to treat a subject, for example a human, with a Hodgkin Lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin Lymphoma; or Nodular Lymphocyte Predominant HL.

Alternatively, the methods described herein, can be used to treat a specific B-cell lymphoma or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; Mediastinal large B cell lymphoma; Nodal marginal zone B cell lymphoma (NMZL); Splenic marginal zone lymphoma (SMZL); Intravascular large B-cell lymphoma; Primary effusion lymphoma; or Lymphomatoid granulomatosis; B-cell prolymphocytic leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; T cell/histiocyte rich large B-cell lymphoma; DLBCL associated with chronic inflammation; Epstein-Barr virus (EBV)+ DLBCL of the elderly; Primary mediastinal (thymic) large B-cell lymphoma; Primary cutaneous DLBCL, leg type; ALK+ large B-cell lymphoma; Plasmablastic lymphoma; Large B-cell lymphoma arising in HHV8-associated multicentric; Castleman disease; B-cell lymphoma, unclassifiable, with features intermediate between diffuse large B-cell lymphoma; or B-cell lymphoma, unclassifiable, with features intermediate between diffuse large B-cell lymphoma and classical Hodgkin lymphoma.

In one embodiment, the methods described herein can be used to treat a leukemia. For example, the subject may be suffering from an acute or chronic leukemia of a lymphocytic or myelogenous origin, such as, but not limited to: Acute lymphoblastic leukemia (ALL); Acute myelogenous leukemia (AML); Chronic lymphocytic leukemia (CLL); Chronic myelogenous leukemia (CIVIL); juvenile myelomonocytic leukemia (JMML); hairy cell leukemia (HCL); acute promyelocytic leukemia (a subtype of AML); large granular lymphocytic leukemia; or Adult T-cell chronic leukemia. In one embodiment, the patient has an acute myelogenous leukemia, for example an undifferentiated AML (M0); myeloblastic leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7).

In some embodiments, the cancer to be treated is selected from estrogen-receptor positive, HER2-negative advanced breast cancer, late-line metastatic breast cancer, liposarcoma, non-small cell lung cancer, liver cancer, ovarian cancer, glioblastoma, refractory solid tumors, retinoblastoma positive breast cancer as well as retinoblastoma positive endometrial, vaginal and ovarian cancers and lung and bronchial cancers.

CDK 4/6-replication independent cellular proliferation disorders, for example as seen in certain types of cancer, can be characterized by one or a combination of increased activity of cyclin-dependent kinase 1 (CDK1), increased activity of cyclin-dependent kinase 2 (CDK2), loss, deficiency, or absence of retinoblastoma tumor suppressor protein (Rb)(Rb-null), high levels of MYC expression, increased cyclin E1, E2, and increased cyclin A. The cancer may be characterized by reduced expression of the retinoblastoma tumor suppressor protein or a retinoblastoma family member protein or proteins (such as, but not limited to p107 and p130). In one embodiment, the subject has an Rb-null or Rb-deficient cancer, including but not limited to small cell lung cancer, triple-negative breast cancer, HPV-positive head and neck cancer, retinoblastoma, Rb-negative bladder cancer, Rb negative prostate cancer, osteosarcoma, or cervical cancer.

CDK4/6-replication dependent cancers can be deduced based on tumor type and molecular genetics using standard techniques, and can be characterized by one or more of the group including, but not limited to, increased activity of CDK1 or CDK2, loss, deficiency, or absence of retinoblastoma tumor suppressor protein (Rb), high levels of MYC expression, increased cyclin E (e.g., E1 or E2) and increased cyclin A, or expression of a Rb-inactivating protein (such as HPV-encoded E7). Such cancers can include, but are not limited to, small cell lung cancer, retinoblastoma, HPV positive malignancies like cervical cancer and certain head and neck cancers, MYC amplified tumors such as Burkitts' Lymphoma, and triple negative breast cancer; certain classes of sarcoma, certain classes of non-small cell lung carcinoma, certain classes of melanoma, certain classes of pancreatic cancer, certain classes of leukemia, certain classes of lymphoma, certain classes of brain cancer, certain classes of colon cancer, certain classes of prostate cancer, certain classes of ovarian cancer, certain classes of uterine cancer, certain classes of thyroid and other endocrine tissue cancers, certain classes of salivary cancers, certain classes of thymic carcinomas, certain classes of kidney cancers, certain classes of bladder cancers, and certain classes of testicular cancers.

In some embodiments, the cancer is selected from a small cell lung cancer, retinoblastoma, and triple negative (ER/PR/Her2 negative) or "basal-like" breast cancer, which almost always have inactivated retinoblastoma tumor suppressor proteins (Rb), and therefore do not require CDK4/6 activity to proliferate. Triple negative (basal-like) breast cancer is also almost always genetically or functionally Rb-null. Also, certain virally induced cancers (e.g. cervical cancer and subsets of Head and Neck cancer) express a viral protein (E7) which inactivates Rb making these tumors functionally Rb-null. Some lung cancers are also believed to be caused by HPV. In one particular embodiment, the cancer is small cell lung cancer, and the patient is treated with a DNA-damaging agent selected from the group consisting of etoposide, carboplatin, and cisplatin, or a combination thereof.

The presence or absence of the retinoblastoma (Rb) tumor suppressor protein (Rb-positive) can be determined through any of the standard assays known to one of ordinary skill in the art, including but not limited to Western Blot, ELISA (enzyme linked immunoadsorbent assay), IHC (immunohistochemistry), and FACS (fluorescent activated cell sorting). The selection of the assay will depend upon the tissue, cell line or surrogate tissue sample that is utilized e.g., for example Western Blot and ELISA may be used with any or all types of tissues, cell lines or surrogate tissues, whereas the IHC method would be more appropriate wherein the tissue utilized in the methods of the present invention was a tumor biopsy. FACs analysis would be most applicable to samples that were single cell suspensions such as cell lines and isolated peripheral blood mononuclear cells. See for example, US 20070212736 "Functional Immunohistochemical Cell Cycle Analysis as a Prognostic Indicator for Cancer". Alternatively, molecular genetic testing may be used for determination of retinoblastoma gene status. Molecular genetic testing for retinoblastoma includes the following as described in Lohmann and Gallie "Retinoblastoma. Gene Reviews" (2010): "A comprehensive, sensitive and economical approach for the detection of mutations in the RB1 gene in retinoblastoma" Journal of Genetics, 88(4), 517-527 (2009).

In one embodiment, the subject has a cancer that expresses PD-L1. PD-L1 expression can be determined by methods known in the art. For example, PD-L1 expression can be detected using PD-L1 IHC 22C3 pharmDx, the FDA-approved in vitro diagnostic immunohistochemistry (IHC) test developed by Dako and Bristol-Meyers Squibb as a companion test for treatment with pembrolizumab. This is qualitative assay using Monoclonal Mouse Anti-PD-L1, Clone 22C3 PD-L1 and EnVision FLEX visualization system on Autostainer Lin 48 to detect PD-L1 in formalin-fixed, paraffin-embedded (FFPE) human non-small cell lung cancer tissue. Expression levels can be measured using the tumor proportion score (TPS), which measures the percentage of viable tumor cells showing partial or complete membrane staining. Staining can show PD-L1 expression from 1% to 100%.

PD-L1 expression can also be detected using PD-L1 IHC 28-8 pharmDx, the FDA-approved in vitro diagnostic immunohistochemistry (IHC) test developed by Dako and Merck as a companion test for treatment with nivolumab. This qualitative assay uses the Monoclonal rabbit anti-PD-L1, Clone 28-8 and EnVision FLEX visualization system on Autostainer Lin 48 to detect PD-L1 in formalin-fixed, paraffin-embedded (FFPE) human non-small cell lung cancer tissue.

Other commercially available tests for PD-L1 detection include the Ventana SP263 assay (developed by Ventana in collaboration with AstraZeneca) that utilizes monoclonal rabbit anti-PD-L1, Clone SP263 and the Ventana SP142 Assay (developed by Ventana in collaboration with Genentech/Roche) that uses rabbit monoclonal anti-PD-L1 clone SP142.

In one embodiment, the PD-L1 expressing cancer is selected from small cell lung carcinoma, non-small cell lung carcinoma, bladder cancer, renal cell carcinoma, gastric cancer, head and neck cancer, mesothelioma, Merkel-cell carcinoma, ovarian, melanoma, pancreatic cancer, or other solid tumors.

Treatment Regimens

As contemplated herein, the administration of the CDK4/6 inhibitor, in combination with a chemotherapeutic agent, for example a DNA-damaging chemotherapeutic agent, and immune checkpoint inhibitor, is timed specifically at a dose described herein so that the G0/G1 arrest induced by the CDK4/6 inhibitor is short term and transient in nature. Cells that are quiescent within the G1 phase of the cell cycle are more resistant to the damaging effect of chemotherapeutic agents than proliferating cells.

As described herein, the CDK4/6 inhibitor can be administered to the subject prior to treatment with a chemotherapeutic agent, during treatment with a chemotherapeutic agent, after exposure to a chemotherapeutic agent, or a combination thereof. As contemplated herein, the CDK4/6 inhibitor is typically administered in a manner that allows the drug facile access to the blood stream, for example via intravenous (IV) injection. In one embodiment, the CDK4/6 inhibitor is administered to the subject less than about 24 hours, 20 hours, 16 hours, 12 hours, 8 hours, or 4 hours, 2.5 hours, 2 hours, 1 hour, ½ hour or less prior to treatment with the chemotherapeutic agent. In an alternative embodiment, the compound is administered to the subject less than about 48 hours, 40 hours, 36 hours, or 32 hours or less prior to treatment with the chemotherapeutic agent. In one embodiment, the selective CDK4/6 inhibitor is a fast-acting, short half-life CDK4/6 inhibitor. In one embodiment, the CDK4/6 inhibitor is Compound I.

Typically, the CDK4/6 inhibitor is administered to the subject prior to treatment with the chemotherapeutic agent such that the compound reaches peak serum levels before or during treatment with the chemotherapeutic agent. In one embodiment, the CDK4/6 inhibitor is administered to the subject about 30 minutes prior to administration of the chemotherapeutic agent. In one embodiment, the CDK4/6 inhibitor is administered to the subject over about a 30-minute period and then the subject is administered a chemotherapeutic agent. In one embodiment, the CDK4/6 inhibitor is administered concomitantly, or closely thereto, with the chemotherapeutic agent exposure. If desired, the compound can be administered multiple times during the chemotherapeutic agent treatment to maximize inhibition, especially when the chemotherapeutic drug is administered over a long period or has a long half-life. In an alternative embodiment, the CDK4/6 inhibitor can be administered following exposure to the chemotherapeutic agent if desired to mitigate healthy cell damage associated with chemotherapeutic agent exposure. In certain embodiments, the CDK4/6 inhibitor is administered up to about ½ hour, up to about 1 hour, up to about 2 hours, up to about 4 hours, up to about 8 hours, up to about 10 hours, up to about 12 hours, up to about 14 hours, up to about 16 hours, or up to about 20 hours or greater following the chemotherapeutic agent exposure. In a particular embodiment, the CDK4/6 inhibitor is administered up to between about 12 hours and 20 hours following exposure to the chemotherapeutic agent. In one embodiment, the selective CDK4/6 inhibitor is a fast-acting, short half-life CDK4/6 inhibitor. In one embodiment, the CDK4/6 inhibitor is Compound I.

In one aspect, the use of a CDK4/6 inhibitor can be administered in an induction dosing schedule with a standard chemotherapeutic dosage schedule or regimen, in combination with an immune checkpoint inhibitor for a multi-day cycle. In one embodiment, the multi-day cycle is 21 days. In a further embodiment, the 21-day cycle is repeated 1, 2, 3, 4, or 5 times or more. For example, the CDK4/6 inhibitor can be administered so that CDK4/6-replication dependent HSPCs and immune effector cells are arrested at the G1 phase during chemotherapeutic agent exposure wherein, due to the rapid dissipation of the G1-arresting effect of the compounds, a significant number of healthy cells reenter the cell-cycle and are capable of becoming activated and/or replicating shortly after chemotherapeutic agent exposure, for example, within less than about 24, 30, 40, or about 48 hours. In one embodiment, a CDK4/6 inhibitor is administered in combination with a chemotherapeutic agent and an immune checkpoint inhibitor including but not limited to a treatment regimen wherein the chemotherapeutic agent is administered: on day 1-3 every 21 days; on days 1-3 every 28 days; on day 1 every 3 weeks; on day 1, day 8, and day 15 every 28 days, on day 1 and day 8 every 28 days; on days 1 and 8 every 21 days; on days 1-5 every 21 days; 1 day a week for 6-8 weeks; on days 1, 22, and 43; days 1 and 2 weekly; days 1-4 and 22-25; days 1-4, 22-25, and 43-46; and similar type-regimens, wherein the CDK4/6-replication dependent cells are arrested at the G1 phase during chemotherapeutic agent exposure. In a further embodiment, the immune checkpoint inhibitor is administered every day, every other day, every three days, once a week, or twice a week. In one embodiment, the CDK4/6 inhibitor is Compound I, the immune checkpoint inhibitor is a PD-1, PD-L1, or CTLA-4 inhibitor. In one embodiment, the immune checkpoint inhibitor is a PD-L1 inhibitor. In one embodiment, the PD-L1 inhibitor is atezolizumab. In one embodiment, the chemotherapy agents are carboplatin and etoposide. In one embodiment, the chemotherapy agent is topotecan.

In one aspect, the use of the CDK4/6 inhibitor can be administered in a maintenance dosing schedule with a standard chemotherapeutic dosage schedule or regimen and immune checkpoint inhibitor, wherein the CDK4/6 inhibitor and the chemotherapy agent are administered alone for a multi-day cycle and once the multi-day cycle is complete, the immune checkpoint inhibitor is administered. In one embodiment, the CDK4/6 inhibitor and the chemotherapy agent are administered for a 21-day cycle and beginning on day 22, the immune checkpoint inhibitor is administered for at least 21 days, at least 42 days, at least 63 days, at last 84 days, or at least 105 days. In one embodiment, the 21-day cycle of CDK4/6 inhibitor and chemotherapy administration is repeated 1, 2, 3, 4, or 5 times before the immune checkpoint inhibitor is administered. In one embodiment, the immune checkpoint inhibitor is administered once daily. In one embodiment, the immune checkpoint inhibitor is administered every other day. In one embodiment, the immune checkpoint inhibitor is administered every three days. In one embodiment, the immune checkpoint inhibitor is administered once a week. In one embodiment, the CDK4/6 inhibitor is Compound I, the immune checkpoint inhibitor is a PD-1 inhibitor, PD-L1 inhibitor, or CTLA-4 inhibitor. In one embodiment, the checkpoint inhibitor is a PD-L1 inhibitor. In one embodiment, the PD-L1 inhibitor is atezolizumab, and the chemotherapy agents are carboplatin and etoposide. In one embodiment, the CDK4/6 inhibitor is Compound I, the immune checkpoint inhibitor is atezolizumab, and the chemotherapy agent is topotecan.

In one aspect, the use of a CDK4/6 inhibitor can be administered in an induction and maintenance dosing schedule with a standard chemotherapeutic dosage schedule or regimen and immune checkpoint inhibitor, wherein the CDK4/6 inhibitor, the chemotherapy agent, and the immune checkpoint inhibitor are administered for a multi-day cycle in the induction phase and once the multi-day cycle is complete, the immune checkpoint inhibitor is further administered in the maintenance phase. In one embodiment, the induction phase is a 21-day cycle. In a further embodiment, the 21-day induction phase is repeated up to 1, 2, 3, 4, or 5 times. In one embodiment, the maintenance phase is at least 21 days, at least 42 days, at least 63 days, at last 84 days, or at least 105 days. In one embodiment, the immune checkpoint inhibitor is administered once daily. In one embodiment, the immune checkpoint inhibitor is administered every other day. In one embodiment, the immune checkpoint inhibitor is administered every three days. In one embodiment, the immune checkpoint inhibitor is administered once a week. In one embodiment, the CDK4/6 inhibitor is Compound I, the immune checkpoint inhibitor is selected from a PD-1 inhibitor, a PD-L1 inhibitor, or a CTLA-4 inhibitor. In one embodiment, the immune checkpoint inhibitor is a PD-L1 inhibitor. In one embodiment, the PD-L1 inhibitor is atezolizumab, and the chemotherapy agents are carboplatin and etoposide. In one embodiment, the CDK4/6 inhibitor is Compound I, the immune checkpoint inhibitor is atezolizumab, and the chemotherapy agent is topotecan.

In one embodiment, a CDK4/6 inhibitor, in combination with an immune checkpoint inhibitor and a chemotherapeutic agent, can be used to increase a pro-inflammatory immune effector cell population in an intra-tumoral immune infiltrate population in a subject with cancer or a tumor. In one embodiment, the pro-inflammatory immune effector cell population is increased by up to 10%, 20%, 30%, 40%, 50% or more compared to the pro-inflammatory immune effector cell population in an intra-tumoral immune cell infiltrate population without the specifically-timed administration of a CDK4/6 inhibitor. In on embodiment, the pro-inflammatory immune effector cell population in an intra-tumoral immune cell infiltrate population is increased by about 10% compared to the pro-inflammatory immune effector cell population in an intra-tumoral immune cell infiltrate population without the specifically-time administration of a CDK4/6 inhibitor. In on embodiment, the pro-inflammatory immune effector cell population in an intra-tumoral immune cell infiltrate population is increased by about 20% compared to the pro-inflammatory immune effector cell population in an intra-tumoral immune cell infiltrate population without the specifically-time administration of a CDK4/6 inhibitor. In on embodiment, the pro-inflammatory immune effector cell population in an intra-tumoral immune cell infiltrate population is increased by about 30% compared to the pro-inflammatory immune effector cell population in an intra-tumoral immune cell infiltrate population without the specifically-time administration of a CDK4/6 inhibitor. In on embodiment, the pro-inflammatory immune effector cell population in an intra-tumoral immune cell infiltrate population is increased by about 40% compared to the pro-inflammatory immune effector cell population in an intra-tumoral immune cell infiltrate population without the specifically-time administration of a CDK4/6 inhibitor. In on embodiment, the pro-inflammatory immune effector cell population in an intra-tumoral immune cell infiltrate population is increased by about 50% compared to the pro-inflammatory immune effector cell population in an intra-tumoral immune cell infiltrate population without the specifically-time administration of a CDK4/6 inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor and a chemotherapeutic agent, can be used to increase T-cell activation in an intra-tumoral immune cell infiltrate population in a subject with cancer or a tumor. In one embodiment, the activated T-cell is a CD4+ T-cell. In one embodiment, the activated T-cell is a CD8+ T-cell. In one embodiment, the activated T-cells produce interferon γ. In one embodiment, the percent of activated T-cells in an intra-tumoral immune cell infiltrate population is about 5%, 10%, 15%, 20%, or more. In one embodiment, the percent of activated T-cells in an intra-tumoral immune cell infiltrate population is about 5%. In one embodiment, the percent of activated T-cells in an intra-tumoral immune cell infiltrate population is about 10%. In one embodiment, the percent of activated T-cells in an intra-tumoral immune cell infiltrate population is about 15%. In one embodiment, the percent of activated T-cells in an intra-tumoral immune cell infiltrate population is about 20%. In one embodiment, the production of interferon γ is increased due to upregulation of the IL2 gene, the IL18 gene, or the LTA gene. In one embodiment, the production of interferon γ is increased due to upregulation of the IL2 gene. In one embodiment, the production of interferon γ is increased due to upregulation of the IL18 gene. In one embodiment, the production of interferon γ is increased due to upregulation of the LTA gene. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab. In one embodiment, a CDK4/6 inhibitor, in combination with an immune checkpoint inhibitor and a chemotherapeutic agent, can be used to reduce the population of regulatory T-cells (Tregs) in an intra-tumoral immune cell infiltrate population in a subject suffering from cancer or a tumor. In one embodiment, the Treg is a CD4+CD25+ Treg. In one embodiment, the population of regulatory T-cells in an intra-tumoral cell infiltrate population is decreased by about 10%, 20%, 30%, 40% or more compared to an intra-tumoral cell infiltrate population from a subject not receiving a CDK4/6 inhibitor. In one embodiment, the population of regulatory T-cells in an intra-tumoral cell infiltrate population is decreased by about 10% compared to an intra-tumoral cell infiltrate population from a subject not receiving a CDK4/6 inhibitor. In one embodiment, the population of regulatory T-cells in an intra-tumoral cell infiltrate population is decreased by about 20% compared to an intra-tumoral cell infiltrate population from a subject not receiving a CDK4/6 inhibitor. In one embodiment, the population of regulatory T-cells in an intra-tumoral cell infiltrate population is decreased by about 30% compared to an intra-tumoral cell infiltrate population from a subject not receiving a CDK4/6 inhibitor. In one embodiment, the population of regulatory T-cells in an intra-tumoral cell infiltrate population is decreased by about 40% compared to an intra-tumoral cell infiltrate population from a subject not receiving a CDK4/6 inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab. In one embodiment, the selective CDK4/6 inhibitor is a fast-acting, short half-life CDK4/6 inhibitor. In one embodiment, the CDK4/6 inhibitor is Compound I.

In one embodiment, a CDK4/6 inhibitor, in combination with an immune checkpoint inhibitor and a chemotherapeutic agent, can be used to inhibit the immune-suppressive function of regulatory T-cells in an intra-tumoral cell infiltrate population in a subject with cancer or a tumor. In one embodiment, the Treg is a CD4+CD25+ Treg. In one embodiment, the proportion of intra-tumor Tregs in the CD4+ T cell population is up to 10, 20, 25, 30, 35, 40 or 50% lower, compared to chemotherapy agent/checkpoint inhibitor alone, after at least 7, 8, 9, 10, or 15 days or more after treatment. In one embodiment, the immune-suppressive function of regulatory T cells is measured by a decrease in Phospho-Rb. In one embodiment, the levels of Phospho-Rb in a regulatory T-cell are decreased by at least 10%, 20%, 30%, 40%, 50% or more compared to an intra-tumoral immune cell infiltrate population from a subject not receiving a CDK4/6 inhibitor. In one embodiment, the levels of Phospho-Rb in a regulatory T-cell are decreased by about 10% compared to an intra-tumoral immune cell infiltrate population from a subject not receiving a CDK4/6 inhibitor. In one embodiment, the levels of Phospho-Rb in a regulatory T-cell are decreased by about 20% compared to an intra-tumoral immune cell infiltrate population from a subject not receiving a CDK4/6 inhibitor. In one embodiment, the levels of Phospho-Rb in a regulatory T-cell are decreased by about 30% compared to an intra-tumoral immune cell infiltrate population from a subject not receiving a CDK4/6 inhibitor. In one embodiment, the levels of Phospho-Rb in a regulatory T-cell are decreased by about 40% compared to an intra-tumoral immune cell infiltrate population from a subject not receiving a CDK4/6 inhibitor. In one embodiment, the levels of Phospho-Rb in a regulatory T-cell are decreased by about 50% compared to an intra-tumoral immune cell infiltrate population from a subject not receiving a CDK4/6 inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab. In one embodiment, the selective CDK4/6 inhibitor is a fast-acting, short half-life CDK4/6 inhibitor. In one embodiment, the CDK4/6 inhibitor is Compound I.

In one embodiment, a CDK4/6 inhibitor, in combination with an immune checkpoint inhibitor and a chemotherapeutic agent, can be used to enhance the generation of tumor-specific memory T-cells in a subject with cancer or a tumor. In one embodiment, the percentage of tumor-specific memory T cells found in the spleen of the subject is increased by at least approximately 0.25%, 0.5%, 0.75%, 1% or more out of total T cell population. In one embodiment, the percentage of tumor-specific memory T cells found in the spleen of the subject is increased by about 0.25% out of total T cell population. In one embodiment, the percentage of tumor-specific memory T cells found in the spleen of the subject is increased by about 0.5% out of total T cell population. In one embodiment, the percentage of tumor-specific memory T cells found in the spleen of the subject is increased by about 0.75% out of total T cell population. In one embodiment, the percentage of tumor-specific memory T cells found in the spleen of the subject is increased by about 1% out of total T cell population. In one embodiment, the percentage of tumor-specific memory T cells found in the blood of the subject is increased by at least approximately 0.5%, 1%, 1.5%, or more out of total T cell population. In one embodiment, the percentage of tumor-specific memory T cells found in the blood of the subject is increased by about 0.5% out of total T cell population. In one embodiment, the percentage of tumor-specific memory T cells found in the blood of the subject is increased by about 1% out of total T cell population. In one embodiment, the percentage of tumor-specific memory T cells found in the blood of the subject is increased by about 1.5% out of total T cell population. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab. In one embodiment, the selective CDK4/6 inhibitor is a fast-acting, short half-life CDK4/6 inhibitor. In one embodiment, the CDK4/6 inhibitor is Compound I.

In one embodiment, a CDK4/6 inhibitor, in combination with an immune checkpoint inhibitor and a chemotherapeutic agent, can be used to protect intra-tumor immune cells from chemotherapy in a subject with cancer or a tumor. In one embodiment, the protection of intra-tumor immune cells from the toxicity of chemotherapy leads to an enhanced anti-tumor immune response. In one embodiment, the protected intra-tumor immune cells are selected from CD8+ T cells, CD4+ T cells, natural killer cells, monocytic myeloid derived suppressor cells (mMDSCs), and granulocytic myeloid derived suppressors cells (gMDSCs). In one embodiment, the protected intra-tumor immune cells are CD8+ T cells. In one embodiment, the protected intra-tumor immune cells are CD4+ T cells. In one embodiment, the protected intra-tumor immune cells are natural killer cells. In one embodiment, the protected intra-tumor immune cells are mMDSCs. In one embodiment, the protected intra-tumor immune cells are gMDSCs. In one embodiment, the percent proliferation of the intra-tumor immune cells is at least approximately 5%, 10%, 15% 20%, 25%, or 30% higher than the proliferation of immune cells found in the spleen. In one embodiment, the percent proliferation of the intra-tumor immune cells is about 5% higher than the proliferation of immune cells found in the spleen. In one embodiment, the percent proliferation of the intra-tumor immune cells is about 10% higher than the proliferation of immune cells found in the spleen. In one embodiment, the percent proliferation of the intra-tumor immune cells is about 15% higher than the proliferation of immune cells found in the spleen. In one embodiment, the percent proliferation of the intra-tumor immune cells is about 20% higher than the proliferation of immune cells found in the spleen. In one embodiment, the percent proliferation of the intra-tumor immune cells is about 25% higher than the proliferation of immune cells found in the spleen. In one embodiment, the percent proliferation of the intra-tumor immune cells is about 30% higher than the proliferation of immune cells found in the spleen. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab. In one embodiment, the proliferation of the intra-tumor immune cells can be inhibited by up to approximately 50%, 60%, 70%, 75%, 80% or more in approximately 6 to 24 hours. In one embodiment, the proliferation of the intra-tumor immune cells can be inhibited by about 50% in approximately 6 to 24 hours. In one embodiment, the proliferation of the intra-tumor immune cells can be inhibited by about 60% in approximately 6 to 24 hours. In one embodiment, the proliferation of the intra-tumor immune cells can be inhibited by about 70% in approximately 6 to 24 hours. In one embodiment, the proliferation of the intra-tumor immune cells can be inhibited by about 75% in approximately 6 to 24 hours. In one embodiment, the proliferation of the intra-tumor immune cells can be inhibited by about 80% in approximately 6 to 24 hours. In one embodiment, the intra-tumor immune cells can recover in approximately equal to or less than 30, 40, 45, 48, 50, or 60 hours. In one embodiment, the intra-tumor immune cells recover in about 30 hours. In one embodiment, the intra-tumor immune cells recover in about 40 hours. In one embodiment, the intra-tumor immune cells recover in about 45 hours. In one embodiment, the intra-tumor immune cells recover in about 48 hours. In one embodiment, the intra-tumor immune cells recover in about 50 hours. In one embodiment, the intra-tumor immune cells recover in about 60 hours. In one embodiment, the selective CDK4/6 inhibitor is a fast-acting, short half-life CDK4/6 inhibitor. In one embodiment, the CDK4/6 inhibitor is Compound I.

In one embodiment, a CDK4/6 inhibitor, in combination with an immune checkpoint inhibitor and a chemotherapeutic agent, can be used to increase a pro-inflammatory immune effector cell population in an intra-tumoral immune infiltrate population in a subject with cancer or a tumor. In one embodiment, the pro-inflammatory immune effector cell population is increased by up to 10%, 20%, 30%, 40%, 50% or more compared to the pro-inflammatory immune effector cell population in an intra-tumoral immune cell infiltrate population without the specifically-timed administration of a selective, fast-acting, short half-life CDK4/6 inhibitor. In on embodiment, the pro-inflammatory immune effector cell population in an intra-tumoral immune cell infiltrate population is increased by about 10% compared to the pro-inflammatory immune effector cell population in an intra-tumoral immune cell infiltrate population without the specifically-time administration of a CDK4/6 inhibitor. In one embodiment, the pro-inflammatory immune effector cell population in an intra-tumoral immune cell infiltrate population is increased by about 20% compared to the pro-inflammatory immune effector cell population in an intra-tumoral immune cell infiltrate population without the specifically-time administration of a CDK4/6 inhibitor. In on embodiment, the pro-inflammatory immune effector cell population in an intra-tumoral immune cell infiltrate population is increased by about 30% compared to the pro-inflammatory immune effector cell population in an intra-tumoral immune cell infiltrate population without the specifically-time administration of a CDK4/6 inhibitor. In on embodiment, the pro-inflammatory immune effector cell population in an intra-tumoral immune cell infiltrate population is increased by about 40% compared to the pro-inflammatory immune effector cell population in an intra-tumoral immune cell infiltrate population without the specifically-time administration of a CDK4/6 inhibitor. In on embodiment, the pro-inflammatory immune effector cell population in an intra-tumoral immune cell infiltrate population is increased by about 50% compared to the pro-inflammatory immune effector cell population in an intra-tumoral immune cell infiltrate population without the specifically-time administration of a CDK4/6 inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab. In one embodiment, the selective CDK4/6 inhibitor is a fast-acting, short half-life CDK4/6 inhibitor. In one embodiment, the CDK4/6 inhibitor is Compound I.

In one embodiment, a CDK4/6 inhibitor, in combination with an immune checkpoint inhibitor and a chemotherapeutic agent, can be used to increase T-cell activation in an intra-tumoral immune cell infiltrate population in a subject with cancer or a tumor. In one embodiment, the activated T-cell is a CD4+ T-cell. In one embodiment, the activated T-cell is a CD8+ T-cell. In one embodiment, the activated T-cells produce interferon γ. In one embodiment, the percent of activated T-cells in an intra-tumoral immune cell infiltrate population is about 5%, 10%, 15%, 20%, or more. In one embodiment, the percent of activated T-cells in an intra-tumoral immune cell infiltrate population is about 5%. In one embodiment, the percent of activated T-cells in an intra-tumoral immune cell infiltrate population is about 10%. In one embodiment, the percent of activated T-cells in an intra-tumoral immune cell infiltrate population is about 15%. In one embodiment, the percent of activated T-cells in an intra-tumoral immune cell infiltrate population is about 20%. In one embodiment, the production of interferon γ is increased due to upregulation of the IL2 gene, the IL18 gene, or the LTA gene. In one embodiment, the production of interferon γ is increased due to upregulation of the IL2 gene. In one embodiment, the production of interferon γ is increased due to upregulation of the IL18 gene. In one embodiment, the production of interferon γ is increased due to upregulation of the LTA gene. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor and a chemotherapeutic agent, can be used to reduce the population of regulatory T-cells (Tregs) in an intra-tumoral immune cell infiltrate population in a subject suffering from cancer or a tumor. In one embodiment, the Treg is a CD4+CD25+ Treg. In one embodiment, the population of regulatory T-cells in an intra-tumoral cell infiltrate population is decreased by about 10%, 20%, 30%, 40% or more compared to an intra-tumoral cell infiltrate population from a subject not receiving a selective, fast-acting, short half-life CDK4/6 inhibitor. In one embodiment, the population of regulatory T-cells in an intra-tumoral cell infiltrate population is decreased by about 10% compared to an intra-tumoral cell infiltrate population from a subject not receiving a selective, fast-acting, short half-life CDK4/6 inhibitor. In one embodiment, the population of regulatory T-cells in an intra-tumoral cell infiltrate population is decreased by about 20% compared to an intra-tumoral cell infiltrate population from a subject not receiving a selective, fast-acting, short half-life CDK4/6 inhibitor. In one embodiment, the population of regulatory T-cells in an intra-tumoral cell infiltrate population is decreased by about 30% compared to an intra-tumoral cell infiltrate population from a subject not receiving a selective, fast-acting, short half-life CDK4/6 inhibitor. In one embodiment, the population of regulatory T-cells in an intra-tumoral cell infiltrate population is decreased by about 40% compared to an intra-tumoral cell infiltrate population from a subject not receiving a CDK4/6 inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor and a chemotherapeutic agent, can be used to inhibit the immune-suppressive function of regulatory T-cells in an intra-tumoral cell infiltrate population in a subject with cancer or a tumor. In one embodiment, the Treg is a CD4+CD25+ Treg. In one embodiment, the proportion of intra-tumor Tregs in the CD4+ T cell population is up to 10, 20, 25, 30, 35, 40 or 50% lower, compared to chemotherapy agent/checkpoint inhibitor alone, after at least 7, 8, 9, 10, or 15 days or more after treatment. In one embodiment, the immune-suppressive function of regulatory T cells is measured by a decrease in Phospho-Rb. In one embodiment, the levels of Phospho-Rb in a regulatory T-cell are decreased by at least 10%, 20%, 30%, 40%, 50% or more compared to an intra-tumoral immune cell infiltrate population from a subject not receiving a CDK4/6 inhibitor. In one embodiment, the levels of Phospho-Rb in a regulatory T-cell are decreased by about 10% compared to an intra-tumoral immune cell infiltrate population from a subject not receiving a CDK4/6 inhibitor. In one embodiment, the levels of Phospho-Rb in a regulatory T-cell are decreased by about 20% compared to an intra-tumoral immune cell infiltrate population from a subject not receiving a CDK4/6 inhibitor. In one embodiment, the levels of Phospho-Rb in a regulatory T-cell are decreased by about 30% compared to an intra-tumoral immune cell infiltrate population from a subject not receiving a CDK4/6 inhibitor. In one embodiment, the levels of Phospho-Rb in a regulatory T-cell are decreased by about 40% compared to an intra-tumoral immune cell infiltrate population from a subject not receiving a CDK4/6 inhibitor. In one embodiment, the levels of Phospho-Rb in a regulatory T-cell are decreased by about 50% compared to an intra-tumoral immune cell infiltrate population from a subject not receiving a CDK4/6 inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor and a chemotherapeutic agent, can be used to enhance the generation of tumor-specific memory T-cells in a subject with cancer or a tumor. In one embodiment, the percentage of tumor-specific memory T cells found in the spleen of the subject is increased by at least approximately 0.25%, 0.5%, 0.75%, 1% or more out of total T cell population. In one embodiment, the percentage of tumor-specific memory T cells found in the spleen of the subject is increased by about 0.25% out of total T cell population. In one embodiment, the percentage of tumor-specific memory T cells found in the spleen of the subject is increased by about 0.5% out of total T cell population. In one embodiment, the percentage of tumor-specific memory T cells found in the spleen of the subject is increased by about 0.75% out of total T cell population. In one embodiment, the percentage of tumor-specific memory T cells found in the spleen of the subject is increased by about 1% out of total T cell population. In one embodiment, the percentage of tumor-specific memory T cells found in the blood of the subject is increased by at least approximately 0.5%, 1%, 1.5%, or more out of total T cell population. In one embodiment, the percentage of tumor-specific memory T cells found in the blood of the subject is increased by about 0.5% out of total T cell population. In one embodiment, the percentage of tumor-specific memory T cells found in the blood of the subject is increased by about 1% out of total T cell population. In one embodiment, the percentage of tumor-specific memory T cells found in the blood of the subject is increased by about 1.5% out of total T cell population. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor and a chemotherapeutic agent, can be used to protect intra-tumor immune cells from chemotherapy in a subject with cancer or a tumor. In one embodiment, the protection of intra-tumor immune cells from the toxicity of chemotherapy leads to an enhanced anti-tumor immune response. In one embodiment, the protected intra-tumor immune cells are selected from CD8+ T cells, CD4+ T cells, natural killer cells, monocytic myeloid derived suppressor cells (mMDSCs), and granulocytic myeloid derived suppressors cells (gMDSCs). In one embodiment, the protected intra-tumor immune cells are CD8+ T cells. In one embodiment, the protected intra-tumor immune cells are CD4+ T cells. In one embodiment, the protected intra-tumor immune cells are natural killer cells. In one embodiment, the protected intra-tumor immune cells are mMDSCs. In one embodiment, the protected intra-tumor immune cells are gMDSCs. In one embodiment, the percent proliferation of the intra-tumor immune cells is at least approximately 5%, 10%, 15% 20%, 25%, or 30% higher than the proliferation of immune cells found in the spleen. In one embodiment, the percent proliferation of the intra-tumor immune cells is about 5% higher than the proliferation of immune cells found in the spleen. In one embodiment, the percent proliferation of the intra-tumor immune cells is about 10% higher than the proliferation of immune cells found in the spleen. In one embodiment, the percent proliferation of the intra-tumor immune cells is about 15% higher than the proliferation of immune cells found in the spleen. In one embodiment, the percent proliferation of the intra-tumor immune cells is about 20% higher than the proliferation of immune cells found in the spleen. In one embodiment, the percent proliferation of the intra-tumor immune cells is about 25% higher than the proliferation of immune cells found in the spleen. In one embodiment, the percent proliferation of the intra-tumor immune cells is about 30% higher than the proliferation of immune cells found in the spleen. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab. In one embodiment, the proliferation of the intra-tumor immune cells can be inhibited by up to approximately 50%, 60%, 70%, 75%, 80% or more in approximately 6 to 24 hours. In one embodiment, the proliferation of the intra-tumor immune cells can be inhibited by about 50% in approximately 6 to 24 hours. In one embodiment, the proliferation of the intra-tumor immune cells can be inhibited by about 60% in approximately 6 to 24 hours. In one embodiment, the proliferation of the intra-tumor immune cells can be inhibited by about 70% in approximately 6 to 24 hours. In one embodiment, the proliferation of the intra-tumor immune cells can be inhibited by about 75% in approximately 6 to 24 hours. In one embodiment, the proliferation of the intra-tumor immune cells can be inhibited by about 80% in approximately 6 to 24 hours. In one embodiment, the intra-tumor immune cells can recover in approximately equal to or less than 30, 40, 45, 48, 50, or 60 hours. In one embodiment, the intra-tumor immune cells recover in about 30 hours. In one embodiment, the intra-tumor immune cells recover in about 40 hours. In one embodiment, the intra-tumor immune cells recover in about 45 hours. In one embodiment, the intra-tumor immune cells recover in about 48 hours. In one embodiment, the intra-tumor immune cells recover in about 50 hours. In one embodiment, the intra-tumor immune cells recover in about 60 hours.

In one embodiment, the subject has small cell lung cancer and the CDK4/6 inhibitor Compound I is administered intravenously over about a 30 minute period about 30 minutes prior to administration of either etoposide or carboplatin on day 1, and etoposide on days 2 and 3 during a 21-day treatment cycle, wherein the subject is administered both etoposide and carboplatin on day 1 and etoposide on day 2 and 3 during a 21-day cycle first line treatment protocol, wherein the subject is further administered an immune checkpoint inhibitor. In one embodiment, the immune checkpoint inhibitor is a PD-1, CTLA-4 inhibitor, or PD-L1 inhibitor. In one embodiment, the immune checkpoint inhibitor is a PD-L1 inhibitor such as atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, the subject has small cell lung cancer and the CDK4/6 inhibitor Compound I is administered intravenously over about a 30-minute period about 30 minutes prior to administration of topotecan during a 21-day treatment cycle, wherein the subject is administered topotecan on days 1, 2, 3, 4, and 5 during a 21-day cycle second or third line treatment protocol, wherein the subject is further administered an immune checkpoint inhibitor. In one embodiment, the immune checkpoint inhibitor is a CTLA-4 inhibitor, PD-1 inhibitor, or PD-L1 inhibitor. In one embodiment, the immune checkpoint inhibitor is a PD-L1 inhibitor such as atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, the subject has small cell lung cancer and the CDK4/6 inhibitor Compound I is administered intravenously over about a 30-minute period about 30 minutes prior to administration of topotecan during a 21-day treatment cycle, wherein the subject is administered topotecan on days 1, 2, and 3 during a 21-day cycle second or third line treatment protocol, wherein the subject is further administered an immune checkpoint inhibitor. In one embodiment, the immune checkpoint inhibitor is a CTLA-4 inhibitor, PD-1 inhibitor, or PD-L1 inhibitor. In one embodiment, the immune checkpoint inhibitor is a PD-L1 inhibitor such as atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, the subject has small cell lung cancer and the CDK4/6 inhibitor Compound I is administered in an induction and maintenance dosing schedule, wherein Compound I is administered intravenously over about a 30-minute period about 30 minutes prior to administration of carboplatin, etoposide, and the immune checkpoint inhibitor, wherein the carboplatin is administered on day 1 and the etoposide is administered on day 1, day 2 and day 3 of a 21-day induction phase chemotherapeutic cycle and the 21-day cycle is repeated 1, 2, 3, 4, or 5 times, wherein the subject is further administered only the immune checkpoint inhibitor in a maintenance phase that begins when the induction phase is complete. In one embodiment, the immune checkpoint inhibitor is further administered in the maintenance phase for at least 21 days, at least 42 days, at least 63 days, at least 84 days, or at least 105 days. In one embodiment, the immune checkpoint inhibitor is administered once daily. In one embodiment, the immune checkpoint inhibitor is administered every other day. In one embodiment, the immune checkpoint inhibitor is administered every three days. In one embodiment, the immune checkpoint inhibitor is administered once a week. In one embodiment, the immune checkpoint inhibitor is atezolizumab.

In one embodiment, the subject has small cell lung cancer and the CDK4/6 inhibitor Compound I is administered in an induction and maintenance dosing schedule, wherein Compound I is administered intravenously over about a 30 minute period about 30 minutes prior to administration of topotecan and the immune checkpoint inhibitor on each of day 1, day 2, day 3, day 4, and day 5 of a 21-day induction phase chemotherapeutic cycle and the 21-day cycle is repeated four times, wherein the subject is further administered only the immune checkpoint inhibitor in a maintenance phase that begins when the induction phase is complete. In one embodiment, the immune checkpoint inhibitor is further administered in the maintenance phase for at least 21 days, at least 42 days, at least 63 days, at least 84 days, or at least 105 days. In one embodiment, the immune checkpoint inhibitor is administered once daily. In one embodiment, the immune checkpoint inhibitor is administered every other day. In one embodiment, the immune checkpoint inhibitor is administered every three days. In one embodiment, the immune checkpoint inhibitor is administered once a week. In one embodiment, the immune checkpoint inhibitor is atezolizumab.

As contemplated herein, a CDK4/6 inhibitor, in combination with an immune checkpoint inhibitor, can be used in conjunction with a number of standard of care chemotherapeutic treatment regimens for example, but not limited to, a small cell lung cancer therapy protocol such as, but not limited to: cisplatin 60 mg/m$^2$ IV on day 1 plus etoposide 120 mg/m$^2$ IV on days 1-3 every 21d for 4 cycles; cisplatin 80 mg/m$^2$ IV on day 1 plus etoposide 100 mg/m$^2$ IV on days 1-3 every 28d for 4 cycles; cisplatin 60-80 mg/m$^2$ IV on day 1 plus etoposide 80-120 mg/m$^2$ IV on days 1-3 every 21-28d (maximum of 4 cycles); carboplatin AUC 5-6 min*mg/mL IV on day 1 plus etoposide 80-100 mg/m$^2$ IV on days 1-3 every 28d (maximum of 4 cycles); cisplatin 60-80 mg/m$^2$ IV on day 1 plus etoposide 80-120 mg/m$^2$ IV on days 1-3 every 21-28d; carboplatin AUC 5-6 min*mg/mL IV on day 1 plus etoposide 80-100 mg/m$^2$ IV on days 1-3 every 28d (maximum 6 cycles); cisplatin 60 mg/m$^2$ IV on day 1 plus irinotecan 60 mg/m$^2$ IV on days 1, 8, and 15 every 28d (maximum 6 cycles); cisplatin 30 mg/m$^2$ IV on days 1 and 8 or 80 mg/m$^2$IV on day 1 plus irinotecan 65 mg/m$^2$ IV on days 1 and 8 every 21d (maximum 6 cycles); carboplatin AUC 5 min*mg/mL IV on day 1 plus irinotecan 50 mg/m$^2$ IV on days 1, 8, and 15 every 28d (maximum 6 cycles); carboplatin AUC 4-5 IV on day 1 plus irinotecan 150-200 mg/m$^2$ IV on day 1 every 21d (maximum 6 cycles); cyclophosphamide 800-1000 mg/m$^2$ IV on day 1 plus doxorubicin 40-50 mg/m$^2$ IV on day 1 plus vincristine 1-1.4 mg/m$^2$ IV on day 1 every 21-28d (maximum 6 cycles); Etoposide 50 mg/m$^2$ PO daily for 3 wk every 4 wk; topotecan 2.3 mg/m$^2$ PO on days 1-5 every 21d; topotecan 1.5 mg/m$^2$ IV on days 1-5 every 21d; carboplatin AUC 5 min*mg/mL IV on day 1 plus irinotecan 50 mg/m$^2$ IV on days 1, 8, and 15 every 28d; carboplatin AUC 4-5 IV on day 1 plus irinotecan 150-200 mg/m$^2$ IV on day 1 every 21d; cisplatin 30 mg/m$^2$ IV on days 1, 8, and 15 plus irinotecan 60 mg/m$^2$ IV on days 1, 8, and 15 every 28d; cisplatin 60 mg/m$^2$ IV on day 1 plus irinotecan 60 mg/m$^2$ IV on days 1, 8, and 15 every 28d; cisplatin 30 mg/m$^2$ IV on days 1 and 8 or 80 mg/m$^2$ IV on day 1 plus irinotecan 65 mg/m$^2$ IV on days 1 and 8 every 21d; paclitaxel 80 mg/m$^2$ IV weekly for 6 wk every 8 wk; paclitaxel 175 mg/m$^2$ IV on day 1 every 3 wk; etoposide 50 mg/m$^2$ PO daily for 3 wk every 4 wk; topotecan 2.3 mg/m$^2$ PO on days 1-5 every 21d; topotecan 1.5 mg/m$^2$ IV on days 1-5 every 21d; carboplatin AUC 5 min*mg/mL IV on day 1 plus irinotecan 50 mg/m$^2$ IV on days 1, 8, and 15 every 28d; carboplatin AUC 4-5 IV on day 1 plus irinotecan 150-200 mg/m$^2$ IV on day 1 every 21d; cisplatin 30 mg/m$^2$ IV on days 1, 8, and 15 plus irinotecan 60 mg/m$^2$ IV on days 1, 8, and 15 every 28d; cisplatin 60 mg/m$^2$ IV on day 1 plus irinotecan 60 mg/m$^2$ IV on days 1, 8, and 15 every 28d; cisplatin 30 mg/m$^2$ IV on days 1 and 8 or 80 mg/m$^2$ IV on day 1 plus irinotecan 65 mg/m$^2$ IV on days 1 and 8 every 21d; paclitaxel 80 mg/m$^2$ IV weekly for 6 wk every 8 wk; and paclitaxel 175 mg/m$^2$ IV on day 1 every 3 wk. In alternative embodiments, Compound I is administered to provide chemoprotection in a small cell lung cancer therapy protocol such as, but not limited to: topotecan 2.0 mg/m$^2$ PO on days 1-5 every 21d; topotecan 1.5-2.3 mg/m$^2$ PO on days 1-5 every 21d; etoposide 100 mg/m$^2$ intravenously (IV) on days 1 through 3 plus cisplatin 50 mg/m$^2$ IV on days 1 and 2 (treatment cycles administered every 3 weeks to a maximum of six cycles); etoposide 100 mg/m$^2$ intravenously (IV) on days 1 through 3 plus carboplatin 300 mg/m$^2$ IV on day 1 (treatment cycles administered every 3 weeks to a maximum of six cycles); carboplatin (300 mg/m$^2$ IV on day 1) and escalating doses of etoposide starting with 80 mg/m$^2$ IV on days 1-3; carboplatin 125 mg/m$^2$/day combined with etoposide 200 mg/m$^2$/day administered for 3 days; etoposide 80-200 mg/m$^2$ intravenously (IV) on days 1 through 3 plus carboplatin 125-450 mg/m$^2$ IV on day 1 (treatment cycles administered every 21-28 days); carboplatin AUC 5-6 min*mg/mL IV on day 1 plus etoposide 80-200 mg/m$^2$ IV on days 1-3 every 28d (maximum of 4 cycles). In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for example, but not limited to, a CDK4/6-replication independent head and neck cancer treatment protocol, such as, but not limited to: cisplatin 100 mg/m$^2$ IV on days 1, 22, and 43 or 40-50 mg/m$^2$ IV weekly for 6-7 wk; cetuximab 400 mg/m$^2$ IV loading dose 1 wk before the start of radiation therapy, then 250 mg/m$^2$ weekly (pre-medicate with dexamethasone, diphenhydramine, and ranitidine); cisplatin 20 mg/m$^2$ IV on day 2 weekly for up to 7 wk plus paclitaxel 30 mg/m$^2$ IV on day 1 weekly for up to 7 wk; cisplatin 20 mg/m$^2$/day IV on days 1-4 and 22-25 plus 5-FU 1000 mg/m$^2$/day by continuous IV infusion on days 1-4 and 22-25; 5-FU 800 mg/m$^2$ by continuous IV infusion on days 1-5 given on the days of radiation plus hydroxyurea 1 g PO q12h (11 doses per cycle); chemotherapy and radiation given every other week for a total of 13 wk; carboplatin 70 mg/m²/day IV on days 1-4, 22-25, and 43-46 plus 5-FU 600 mg/m²/day by continuous IV infusion on days 1-4, 22-25, and 43-46; carboplatin AUC 1.5 IV on day 1 weekly plus paclitaxel 45 mg/m² IV on day 1 weekly; cisplatin 100 mg/m² IV on days 1, 22, and 43 or 40-50 mg/m² IV weekly for 6-7 wk; docetaxel 75 mg/m² IV on day 1 plus cisplatin 100 mg/m² IV on day 1 plus 5-FU 100 mg/m²/day by continuous IV infusion on days 1-4 every 3 wk for 3 cycles, then 3-8 wk later, carboplatin AUC 1.5 IV weekly for up to 7 wk during radiation therapy; docetaxel 75 mg/m² IV on day 1 plus cisplatin 75 mg/m² IV on day 1 plus 5-FU 750 mg/m²/day by continuous IV infusion on days 1-4 every 3 wk for 4 cycles; cisplatin 100 mg/m² IV on day 1 every 3 wk for 6 cycles plus 5-FU 1000 mg/m²/day by continuous IV infusion on days 1-4 every 3 wk for 6 cycles plus cetuximab 400 mg/m² IV loading dose on day 1, then 250 mg/m² IV weekly until disease progression (pre-medicate with dexamethasone, diphenhydramine, and ranitidine); carboplatin AUC 5 min*mg/mL IV on day 1 every 3 wk for 6 cycles plus 5-FU 1000 mg/m²/day by continuous IV infusion on days 1-4 every 3 wk for 6 cycles plus cetuximab 400 mg/m² IV loading dose on day 1, then 250 mg/m² IV weekly until disease progression (pre-medicate with dexamethasone, diphenhydramine, and ranitidine); cisplatin 75 mg/m² IV on day 1 plus docetaxel 75 mg/m² IV on day 1 every 3 wk; cisplatin 75 mg/m² IV on day 1 plus paclitaxel 175 mg/m² IV on day 1 every 3 wk; carboplatin AUC 6 IV on day 1 plus docetaxel 65 mg/m² IV on day 1 every 3 wk; carboplatin AUC 6 IV on day 1 plus paclitaxel 200 mg/m² IV on day 1 every 3 wk; cisplatin 75-100 mg/m² IV on day 1 every 3-4 wk plus cetuximab 400 mg/m² IV loading dose on day 1, then 250 mg/m² IV weekly (pre-medicate with dexamethasone, diphenhydramine, and ranitidine); cisplatin 100 mg/m² IV on day 1 plus 5-FU 1000 mg/m²/day by continuous IV infusion on days 1-4 every 3 wk; methotrexate 40 mg/m² IV weekly (3 wk equals 1 cycle); paclitaxel 200 mg/m² IV every 3 wk; docetaxel 75 mg/m² IV every 3 wk; cetuximab 400 mg/m² IV loading dose on day 1, then 250 mg/m² IV weekly until disease progression (pre-medicate with dexamethasone, diphenhydramine, and ranitidine); cisplatin 100 mg/m² IV on day 1 every 3 wk for 6 cycles plus 5-FU 1000 mg/m²/day by continuous IV infusion on days 1-4 every 3 wk for 6 cycles plus cetuximab 400 mg/m² IV loading dose on day 1, then 250 mg/m² IV weekly (pre-medicate with dexamethasone, diphenhydramine, and ranitidine); carboplatin AUC 5 min*mg/mL IV on day 1 every 3 wk for 6 cycles plus 5-FU 1000 mg/m²/day by continuous IV infusion on days 1-4 every 3 wk for 6 cycles plus cetuximab 400 mg/m² IV loading dose on day 1, then 250 mg/m² IV weekly (pre-medicate with dexamethasone, diphenhydramine, and ranitidine); cisplatin 75 mg/m² IV on day 1 plus docetaxel 75 mg/m² IV on day 1 every 3 wk; cisplatin 75 mg/m² IV on day 1 plus paclitaxel 175 mg/m² IV on day 1 every 3 wk; carboplatin AUC 6 IV on day 1 plus docetaxel 65 mg/m² IV on day 1 every 3 wk; carboplatin AUC 6 IV on day 1 plus paclitaxel 200 mg/m² IV on day 1 every 3 wk; cisplatin 75-100 mg/m² IV on day 1 every 3-4 wk plus cetuximab 400 mg/m² IV loading dose on day 1, then 250 mg/m² IV weekly (pre-medicate with dexamethasone, diphenhydramine, and ranitidine); cisplatin 100 mg/m² IV on day 1 plus 5-FU 1000 mg/m²/day by continuous IV infusion on days 1-4 every 3 wk; methotrexate 40 mg/m² IV weekly (3 wk equals 1 cycle); paclitaxel 200 mg/m² IV every 3 wk; docetaxel 75 mg/m² IV every 3 wk; cetuximab 400 mg/m² IV loading dose on day 1, then 250 mg/m² IV weekly until disease progression (pre-medicate with dexamethasone, diphenhydramine, and ranitidine); cisplatin 100 mg/m² IV on days 1, 22, and 43 with radiation, then cisplatin 80 mg/m² IV on day 1 plus 5-FU 1000 mg/m²/day by continuous IV infusion on days 1-4 every 4 wk for 3 cycles; cisplatin 75 mg/m² IV on day 1 plus docetaxel 75 mg/m² IV on day 1 every 3 wk; cisplatin 75 mg/m² IV on day 1 plus paclitaxel 175 mg/m² IV on day 1 every 3 wk; carboplatin AUC 6 IV on day 1 plus docetaxel 65 mg/m² IV on day 1 every 3 wk; carboplatin AUC 6 IV on day 1 plus paclitaxel 200 mg/m² IV on day 1 every 3 wk; cisplatin 100 mg/m² IV on day 1 plus 5-FU 1000 mg/m²/day by continuous IV infusion on days 1-4 every 3 wk; cisplatin 50-70 mg/m² IV on day 1 plus gemcitabine 1000 mg/m² IV on days 1, 8, and 15 every 4 wk; gemcitabine 1000 mg/m² IV on days 1, 8, and 15 every 4 wk or gemcitabine 1250 mg/m² IV on days 1 and 8 every 3 wk; methotrexate 40 mg/m² IV weekly (3 wk equals 1 cycle); paclitaxel 200 mg/m² IV every 3 wk; docetaxel 75 mg/m² IV every 3 wk; cisplatin 75 mg/m² IV on day 1 plus docetaxel 75 mg/m² IV on day 1 every 3 wk; cisplatin 75 mg/m² IV on day 1 plus paclitaxel 175 mg/m² IV on day 1 every 3 wk; carboplatin AUC 6 IV on day 1 plus docetaxel 65 mg/m² IV on day 1 every 3 wk; carboplatin AUC 6 IV on day 1 plus paclitaxel 200 mg/m² IV on day 1 every 3 wk; cisplatin 100 mg/m² IV on day 1 plus 5-FU 1000 mg/m²/day by continuous IV infusion on days 1-4 every 3 wk; cisplatin 50-70 mg/m² IV on day 1 plus gemcitabine 1000 mg/m² IV on days 1, 8, and 15 every 4 wk; gemcitabine 1000 mg/m² IV on days 1, 8, and 15 every 4 wk or gemcitabine 1250 mg/m² IV on days 1 and 8 every 3 wk; methotrexate 40 mg/m² IV weekly (3 wk equals 1 cycle); paclitaxel 200 mg/m² IV every 3 wk; and docetaxel 75 mg/m² IV every 3 wk. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for example, but not limited to, a CDK4/6-replication independent triple negative breast cancer treatment protocol such as, but not limited to: dose-dense doxorubicin (Adriamycin) and cyclophosphamide (Cytoxan) every two weeks for four cycles followed by dose-dense paclitaxel (Taxol®) every two weeks for four cycles; Adriamycin/paclitaxel/cyclophosphamide every three weeks for a total of four cycles; Adriamycin/paclitaxel/cyclophosphamide every two weeks for a total of four cycles; Adriamycin/cyclophosphamide followed by paclitaxel (Taxol®) every three weeks for four cycles each; and Adriamycin/cyclophosphamide followed by paclitaxel (Taxol®) every two weeks for four cycles each. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for example, but not limited to, a CDK4/6-replication independent bladder cancer treatment protocol such as, but not limited to: postoperative adjuvant intravesical chemotherapy for non-muscle invasive bladder cancer, first-line chemotherapy for muscle-invasive bladder cancer, and second-line chemotherapy for muscle invasive bladder cancer. Non-limiting examples of postoperative chemotherapy for bladder cancer include one dose or mitomycin (40 mg), epirubicin (80 mg), thiotepa (30 mg), or doxorubicin (50 mg). Non-limiting examples of first-line chemotherapy for bladder cancer include: gemcitabine 1000 mg/m2 on days 1, 8, and 15 plus cisplatin 70 mg/m$^2$ on day 1 or 2 repeating cycle every 28 days for a total of four cycles; dosing methotrexate 30 mg/m$^2$ IV on days 1, 15, and 22 plus vinblastine 3 mg/m$^2$ IV on days 2, 15, and 22 plus doxorubicin 30 mg/m$^2$ IV on day 2 plus cisplatin 70 mg/m$^2$ IV on day 2, repeat cycle every 28d for a total of 3 cycles; and dose-dense regimens of the above administered along with doses of growth factor stimulants. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for example, but not limited to, a CDK4/6-replication independent retinoblastoma treatment protocol such as, but not limited to the administration of carboplatin, vincristine, or etoposide in conjunction with surgery, radiotherapy, cryotherapy, thermotherapy, or other local therapy techniques. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for example, but not limited to a CDK4/6-replication independent cervical cancer treatment protocol such as, but not limited to the administration of cisplatin 40 mg/m$^2$ IV once weekly, cisplatin 50-75 mg/m$^2$ IV on day 1 plus 5-fluorouracil (5-FU) 1000 mg/m$^2$ continuous IV infusion on days 2-5 and days 30-33, cisplatin 50-75 mg/m$^2$ IV on day 1 plus 5-FU 1000 mg/m$^2$ IV infusion over 24 hour on days 1-4 every 3 weeks for 3-4 cycles, bevacizumab 15 mg/kg IV over 30-90 minutes plus cisplatin on day 1 or 2 plus paclitaxel on day 1 every 3 weeks, bevacizumab plus paclitaxel on day 1 plus topotecan on days 1-3 every 3 weeks, paclitaxel followed by cisplatin on day 1 every 3 weeks, topotecan on days 1-3 followed by cisplatin on day 1 every 3 weeks, and paclitaxel on day 1 every 3 weeks. In another embodiment the cervical cancer therapy protocol is as above in addition to radiation, surgery, or another procedure. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for Triple-negative breast cancer (TNBC). TNBC is defined as the absence of staining for estrogen receptor, progesterone receptor, and HER2/neu. TNBC is insensitive to some of the most effective therapies available for breast cancer treatment including HER2-directed therapy such as trastuzumab and endocrine therapies such as tamoxifen or the aromatase inhibitors. Combination cytotoxic chemotherapy administered in a dose-dense or metronomic schedule remains the standard therapy for early-stage TNBC. Platinum agents have recently emerged as drugs of interest for the treatment of TNBC with carboplatin added to paclitaxel and Adriamycin plus cyclophosphamide chemotherapy in the neoadjuvant setting. The poly (ADP-ribose) polymerase (PARP) inhibitors, including niraparib (Tesaro), are emerging as promising therapeutics for the treatment of TNBC. PARPs are a family of enzymes involved in multiple cellular processes, including DNA repair. In one embodiment, the TNBC therapy is combined with a CDK4/6 inhibitor and an immune checkpoint inhibitor. In one embodiment, the TNBC therapy is the PARP inhibitor niraparib. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for AML. AML, treatments include cytarabine (cytosine arabinoside or ara-C) and the anthracycline drugs (such as daunorubicin/daunomycin, idarubicin, and mitoxantrone). Other chemo drugs that may be used to treat AML include: Cladribine (Leustatin®, 2-CdA), Fludarabine (Fludara®), Topotecan, Etoposide (VP-16), 6-thioguanine (6-TG), Hydroxyurea (Hydrea®), Corticosteroid drugs, such as prednisone or dexamethasone (Decadron®), Methotrexate (MTX), 6-mercaptopurine (6-MP), Azacitidine (Vidaza®), Decitabine (Dacogen®). In one embodiment, the AML therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for CLL and other lymphomas. CLL treatments include: purine analogs such as fludarabine (Fludara®), pentostatin (Nipent®), and cladribine (2-CdA, Leustatin®), and alkylating agents, which include chlorambucil (Leukeran®) and cyclophosphamide (Cytoxan®) and bendamustine (Treanda®). Other drugs sometimes used for CLL include doxorubicin (Adriamycin®), methotrexate, oxaliplatin, vincristine (Oncovin®), etoposide (VP-16), and cytarabine (ara-C). Other drugs include Rituximab (Rituxan®), Obinutuzumab (Gazyva™) Ofatumumab (Arzerra®), Alemtuzumab (Campath®) and Ibrutinib (Imbruvica™). In one embodiment, the CLL therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for CIVIL. CML treatments include: Interferon, imatinib (Gleevec®), the chemo drug hydroxyurea (Hydrea®), cytarabine (Ara-C), busulfan, cyclophosphamide (Cytoxan®), and vincristine (Oncovin®). Omacetaxine (Synribo®) is a chemo drug that was approved to treat CIVIL that is resistant to some of the TKIs now in use. In one embodiment, the CIVIL therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for CMML. CMML treatments include Deferasirox (Exjade®), cytarabine with idarubicin, cytarabine with topotecan, and cytarabine with fludarabine, Hydroxyurea (hydroxycarbamate, Hydrea®), azacytidine (Vidaza®) and decitabine (Dacogen®). In one embodiment, the CMML therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for multiple myeloma. Multiple myeloma treatments include Pomalidomide (Pomalyst®), Carfilzomib (Kyprolis™), Everolimus (Afinitor®), dexamethasone (Decadron®), prednisone and methylprednisolone (Solu-medrol®) and hydrocortisone. In one embodiment, the multiple myeloma therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for Hodgkin's disease. Hodgkin's disease treatments include Brentuximab vedotin (Adcetris™): anti-CD-30, Rituximab, Adriamycin® (doxorubicin), Bleomycin, Vinblastine, Dacarbazine (DTIC). In one embodiment, the Hodgkin's disease therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for non-Hodgkin's disease. Non-Hodgkin's disease treatments include Rituximab (Rituxan®), Ibritumomab (Zevalin®), tositumomab (Bexxar®), Alemtuzumab (Campath®) (CD52 antigen), Ofatumumab (Arzerra®), Brentuximab vedotin (Adcetris®) and Lenalidomide (Revlimid®). In one embodiment, the non-Hodgkin's disease therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for Diffuse Large B-cell lymphoma (DLBCL). DLBCL treatments include CHOP (cyclophosphamide, doxorubicin, vincristine, and prednisone), plus the monoclonal antibody rituximab (Rituxan®). This regimen, known as R-CHOP, is usually given for about 6 months. In one embodiment, the DLBCL therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for Primary mediastinal B-cell lymphoma. Primary mediastinal B-cell lymphoma treatments include R-CHOP. In one embodiment, the Primary mediastinal B-cell lymphoma therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for Follicular lymphoma. Follicular lymphoma treatments include rituximab (Rituxan®) combined with chemo, using either a single chemo drug (such as bendamustine or fludarabine) or a combination of drugs, such as the CHOP or CVP (cyclophosphamide, vincristine, prednisone regimens. The radioactive monoclonal antibodies, ibritumomab (Zevalin®) and tositumomab (Bexxar®) are also possible treatment options. For patients who may not be able to tolerate more intensive chemo regimens, rituximab alone, milder chemo drugs (such as chlorambucil or cyclophosphamide). In one embodiment, the Follicular lymphoma therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for Chronic lymphocytic leukemia/small lymphocytic lymphoma. Chronic lymphocytic leukemia/small lymphocytic lymphoma treatments include R-CHOP. In one embodiment, the Chronic lymphocytic leukemia/small lymphocytic lymphoma therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for Mantle cell lymphoma. Mantle cell lymphoma treatments include: fludarabine, cladribine, or pentostatin; bortezomib (Velcade®) and lenalidomide (Revlimid®) and ibrutinib (Imbruvica®). In one embodiment, the Mantle cell lymphoma therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for Extranodal marginal zone B-cell lymphomamucosa-associated lymphoid tissue (MALT) lymphoma. Extranodal marginal zone B-cell lymphoma-mucosa-associated lymphoid tissue (MALT) lymphoma treatments include rituximab; chlorambucil or fludarabine or combinations such as CVP, often along with rituximab. In one embodiment, the Extranodal marginal zone B-cell lymphoma-mucosa-associated lymphoid tissue (MALT) lymphoma therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for Nodal marginal zone B-cell lymphoma. Nodal marginal zone B-cell lymphoma treatments include rituximab (Rituxan®) combined with chemo, using either a single chemo drug (such as bendamustine or fludarabine) or a combination of drugs, such as the CHOP or CVP (cyclophosphamide, vincristine, prednisone regimens.

The radioactive monoclonal antibodies, ibritumomab (Zevalin®) and tositumomab (Bexxar®) are also possible treatment options. For patients who may not be able to tolerate more intensive chemo regimens, rituximab alone, milder chemo drugs (such as chlorambucil or cyclophosphamide). In one embodiment, the Nodal marginal zone B-cell lymphoma therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for Splenic marginal zone B-cell lymphoma. Splenic marginal zone B-cell lymphoma treatments include rituximab. In one embodiment, the Splenic marginal zone B-cell lymphoma therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for Burkitt lymphoma. Burkitt lymphoma treatments include methotrexate; hyper-CVAD-cyclophosphamide, vincristine, doxorubicin (also known as Adriamycin®), and dexamethasone. Course B consists of methotrexate and cytarabine; CODOX-M-cyclophosphamide, doxorubicin, high-dose methotrexate/ifosfamide, etoposide, and high-dose cytarabine; etoposide, vincristine, doxorubicin, cyclophosphamide, and prednisone (EPOCH). In one embodiment, the Burkitt lymphoma therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for Lymphoplasmacytic lymphoma. Lymphoplasmacytic lymphoma treatments include rituximab. In one embodiment, the Lymphoplasmacytic lymphoma therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for Hairy cell leukemia. Hairy cell leukemia treatments include cladribine (2-CdA) or pentostatin; rituximab; interferon-alfa. In one embodiment, the Hairy cell leukemia therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for Precursor T-lymphoblastic lymphoma/leukemia. Precursor T-lymphoblastic lymphoma/leukemia treatments include cyclophosphamide, doxorubicin (Adriamycin®), vincristine, L-asparaginase, methotrexate, prednisone, and, sometimes, cytarabine (ara-C). Because of the risk of spread to the brain and spinal cord, a chemo drug such as methotrexate is also given into the spinal fluid. In one embodiment, the Precursor T-lymphoblastic lymphoma/leukemia therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for Skin lymphomas. Skin lymphomas treatments include Gemcitabine Liposomal doxorubicin (Doxil®); Methotrexate; Chlorambucil; Cyclophosphamide; Pentostatin; Etoposide; Temozolomide; Pralatrexate; R-CHOP. In one embodiment, the Skin lymphomas therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for Angioimmunoblastic T-cell lymphoma. Angioimmunoblastic T-cell lymphoma treatments include prednisone or dexamethasone. In one embodiment, the Angioimmunoblastic T-cell lymphoma therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for Extranodal natural killer/T-cell lymphoma, nasal type. Extranodal natural killer/T-cell lymphoma, nasal type treatments include CHOP. In one embodiment, the Extranodal natural killer/T-cell lymphoma, nasal type therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for Anaplastic large cell lymphoma. Anaplastic large cell lymphoma treatments include CHOP; pralatrexate (Folotyn®), targeted drugs such as bortezomib (Velcade®) or romidepsin (Istodax), or immunotherapy drugs such as alemtuzumab (Campath®) and denileukin diftitox (Ontak®). In one embodiment, Anaplastic large cell lymphoma therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, a CDK4/6 inhibitor, in combination with an immune checkpoint inhibitor, can be used in conjunction with a number of standard of care chemotherapeutic treatment regimens for Primary central nervous system (CNS) lymphoma. Primary central nervous system (CNS) lymphoma treatments include methotrexate; rituximab. In one embodiment, Primary central nervous system (CNS) lymphoma therapy is combined with a CDK4/6 inhibitor and an immune checkpoint inhibitor. In one embodiment, the CDK4/6 inhibitor is Compound I. In one embodiment, the immune checkpoint inhibitor is a CTLA-4 inhibitor, PD-1 inhibitor, or PD-L1 inhibitor. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, the subject has small cell lung cancer and is administered a chemotherapeutic agent selected from the group consisting of carboplatin, cisplatin, oxaliplatin, etoposide, and topotecan, or a combination thereof in combination with a CDK4/6 inhibitor and an immune checkpoint inhibitor. In one embodiment, the CDK4/6 inhibitor is Compound I or Compound II. In one embodiment, the immune checkpoint inhibitor is a CTLA-4 inhibitor, PD-1 inhibitor, or PD-L1 inhibitor. In one embodiment, the immune checkpoint inhibitor is a PD-L1 inhibitor selected from durvalumab, avelumab, and atezolizumab. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab.

In one embodiment, the chemotherapeutic agent is etoposide, the CDK4/6 inhibitor is Compound I, and the PD-L1 inhibitor is atezolizumab. In one embodiment, the chemotherapeutic agent is carboplatin, the CDK4/6 inhibitor is Compound I, and the PD-L1 inhibitor is atezolizumab. In one embodiment, the chemotherapeutic agent is a combination therapeutic regime comprising carboplatin and etoposide, the CDK4/6 inhibitor is Compound I, and the PD-L1 inhibitor is atezolizumab. In one embodiment, the chemotherapeutic agent is cisplatin, the CDK4/6 inhibitor is Compound I, and the PD-L1 inhibitor is atezolizumab. In one embodiment, the chemotherapeutic agent is topotecan, the CDK4/6 inhibitor is Compound I, and the PD-L1 inhibitor is atezolizumab. In one embodiment, the chemotherapeutic agent is oxaliplatin, the CDK4/6 inhibitor is Compound I, and the PD-L1 inhibitor is atezolizumab.

In one embodiment, the subject has melanoma and is administered a chemotherapeutic agent selected from the group consisting of dacarbazine, temozolomide, nab-paclitaxel, paclitaxel, cisplatin, oxaliplatin, carboplatin, vinblastine, or a combination thereof, in combination with a CDK4/6 inhibitor and an immune checkpoint inhibitor. In one embodiment, the CDK4/6 inhibitor is Compound I or Compound II. In one embodiment, the immune checkpoint inhibitor is a CTLA-4 inhibitor. PD-1 inhibitor, or PD-L1 inhibitor. In one embodiment, the immune checkpoint inhibitor is a PD-L1 inhibitor selected from durvalumab, avelumab, and atezolizumab. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab. In one embodiment, the chemotherapeutic agent is dacarbazine, the CDK4/6 inhibitor is Compound I, and the PD-L1 inhibitor is atezolizumab. In one embodiment, the chemotherapeutic agent is temozolomide, the CDK4/6 inhibitor is Compound I, and the PD-L1 inhibitor is atezolizumab. In one embodiment, the chemotherapeutic agent is nab-paclitaxel, the CDK4/6 inhibitor is Compound I, and the PD-L1 inhibitor is atezolizumab. In one embodiment, the chemotherapeutic agent is paclitaxel, the CDK4/6 inhibitor is Compound I, and the PD-L1 inhibitor is atezolizumab. In one embodiment, the chemotherapeutic agent is cisplatin, the CDK4/6 inhibitor is Compound I, and the PD-L1 inhibitor is atezolizumab. In one embodiment, the chemotherapeutic agent is carboplatin, the CDK4/6 inhibitor is Compound I, and the PD-L1 inhibitor is atezolizumab. In one embodiment, the chemotherapeutic agent is vinblastine, the CDK4/6 inhibitor is Compound I, and the PD-L1 inhibitor is atezolizumab. In one embodiment, the chemotherapeutic agent is oxaliplatin, the CDK4/6 inhibitor is Compound I, and the PD-L1 inhibitor is atezolizumab.

In one embodiment, the subject has renal cell carcinoma and is being administered a chemotherapeutic agent selected from the group consisting of vinblastine, floxuridine, 5-fluorouracil, capecitabine, and gemcitabine, or a combination thereof, in combination with a CDK4/6 inhibitor and an immune checkpoint inhibitor. In one embodiment, the CDK4/6 inhibitor is Compound I or Compound II. In one embodiment, the immune checkpoint inhibitor is a CTLA-4 inhibitor, PD-1 inhibitor, or PD-L1 inhibitor. In one embodiment, the immune checkpoint inhibitor is a PD-L1 inhibitor selected from durvalumab, avelumab, and atezolizumab. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab. In one embodiment, the chemotherapeutic agent is vinblastine, the CDK4/6 inhibitor is Compound I, and the PD-L1 inhibitor is atezolizumab. In one embodiment, the chemotherapeutic agent is floxuridine, the CDK4/6 inhibitor is Compound I, and the PD-L1 inhibitor is atezolizumab. In one embodiment, the chemotherapeutic agent is 5-fluorouracil, the CDK4/6 inhibitor is Compound I, and the PD-L1 inhibitor is atezolizumab. In one embodiment, the chemotherapeutic agent is capecitabine, the CDK4/6 inhibitor is Compound I, and the PD-L1 inhibitor is atezolizumab. In one embodiment, the chemotherapeutic agent is gemcitabine, the CDK4/6 inhibitor is Compound I, and the PD-L1 inhibitor is atezolizumab.

In one embodiment, the subject has bladder cancer and is being administered a chemotherapeutic agent selected from the group consisting of carboplatin, oxaliplatin, cisplatin, fluorouracil, mitomycin, methotrexate, vinblastine, doxorubicin, gemcitabine, paclitaxel, or a combination thereof, in combination with a CDK4/6 inhibitor and an immune checkpoint inhibitor. In one embodiment, the CDK4/6 inhibitor is Compound I or Compound II. In one embodiment, the immune checkpoint inhibitor is a CTLA-4 inhibitor, PD-1 inhibitor, or PD-L1 inhibitor. In one embodiment, the immune checkpoint inhibitor is a PD-L1 inhibitor selected from durvalumab, avelumab, and atezolizumab. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab. In one embodiment, the chemotherapeutic agent is cisplatin, the CDK4/6 inhibitor is Compound I, and the PD-L1 inhibitor is atezolizumab. In one embodiment, the chemotherapeutic agent is a combination therapeutic regime comprising cisplatin and 5-fluorouracil, the CDK4/6 inhibitor is Compound I, and the PD-L1 inhibitor is atezolizumab. In one embodiment, the chemotherapeutic agent is a combination therapeutic regime comprising mitomycin and 5-fluorouracil, the CDK4/6 inhibitor is Compound I, and the PD-L1 inhibitor is atezolizumab. In one embodiment, the chemotherapeutic agent is a combination therapeutic regime comprising cisplatin and gemcitabine, the CDK4/6 inhibitor is Compound I, and the PD-L1 inhibitor is atezolizumab. In one embodiment, the chemotherapeutic agent is a combination therapeutic regime comprising cisplatin, methotrexate, vinblastine and doxorubicin, the CDK4/6 inhibitor is Compound I, and the PD-L1 inhibitor is atezolizumab. In one embodiment, the chemotherapeutic agent is a combination therapeutic regime comprising cisplatin, methotrexate, and vinblastine, the CDK4/6 inhibitor is Compound I, and the PD-L1 inhibitor is atezolizumab. In one embodiment, the chemotherapeutic agent is a combination therapeutic regime comprising carboplatin and paclitaxel, the CDK4/6 inhibitor is Compound I, and the PD-L1 inhibitor is atezolizumab. In one embodiment, the chemotherapeutic agent is oxaliplatin, the CDK4/6 inhibitor is Compound I, and the PD-L1 inhibitor is atezolizumab.

In one embodiment, the subject has urothelial carcinoma and is being administered a chemotherapeutic agent selected from the group consisting of carboplatin, cisplatin, oxaliplatin, fluorouracil, mitomycin, methotrexate, vinblastine, doxorubicin, gemcitabine, paclitaxel, or a combination thereof, in combination with a CDK4/6 inhibitor and an immune checkpoint inhibitor. In one embodiment, the CDK4/6 inhibitor is Compound I or Compound II. In one embodiment, the immune checkpoint inhibitor is a CTLA-4 inhibitor, PD-1 inhibitor, or PD-L1 inhibitor. In one embodiment, the immune checkpoint inhibitor is a PD-L1 inhibitor selected from durvalumab, avelumab, and atezolizumab. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab. In one embodiment, the chemotherapeutic agent is cisplatin, the CDK4/6 inhibitor is Compound I, and the PD-L1 inhibitor is atezolizumab. In one embodiment, the chemotherapeutic agent is a combination therapeutic regime comprising cisplatin and 5-fluorouracil, the CDK4/6 inhibitor is Compound I, and the PD-L1 inhibitor is atezolizumab. In one embodiment, the chemotherapeutic agent is a combination therapeutic regime comprising mitomycin and 5-fluorouracil, the CDK4/6 inhibitor is Compound I, and the PD-L1 inhibitor is atezolizumab. In one embodiment, the chemotherapeutic agent is a combination therapeutic regime comprising cisplatin and gemcitabine, the CDK4/6 inhibitor is Compound I, and the PD-L1 inhibitor is atezolizumab. In one embodiment, the chemotherapeutic agent is a combination therapeutic regime comprising cisplatin, methotrexate, vinblastine and doxorubicin, the CDK4/6 inhibitor is Compound I, and the PD-L1 inhibitor is atezolizumab. In one embodiment, the chemotherapeutic agent is a combination therapeutic regime comprising cisplatin, methotrexate, and vinblastine, the CDK4/6 inhibitor is Compound I, and the PD-L1 inhibitor is atezolizumab. In one embodiment, the chemotherapeutic agent is a combination therapeutic regime comprising carboplatin and paclitaxel, the CDK4/6 inhibitor is Compound I, and the PD-L1 inhibitor is atezolizumab. In one embodiment, the chemotherapeutic agent is oxaliplatin, the CDK4/6 inhibitor is Compound I, and the PD-L1 inhibitor is atezolizumab.

In one embodiment, the subject has breast cancer and is being administered a chemotherapeutic agent selected from the group consisting of carboplatin, oxaliplatin, cisplatin, doxorubicin, 5-fluorouracil, paclitaxel, cyclophosphamide, gemcitabine, or a combination thereof, in combination with a CDK4/6 inhibitor and an immune checkpoint inhibitor. In one embodiment, the CDK4/6 inhibitor is Compound I or Compound II. In one embodiment, the immune checkpoint inhibitor is a CTLA-4 inhibitor, PD-1 inhibitor, or PD-L1 inhibitor. In one embodiment, the immune checkpoint inhibitor is a PD-L1 inhibitor selected from durvalumab, avelumab, and atezolizumab. In one embodiment, the PD-L1 inhibitor is atezolizumab. In one embodiment, the chemotherapeutic agent is carboplatin, the CDK4/6 inhibitor is Compound I, and the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab. In one embodiment, the chemotherapeutic agent is cisplatin, the CDK4/6 inhibitor is Compound I, and the PD-L1 inhibitor is atezolizumab. In one embodiment, the chemotherapeutic agent is a combination therapeutic regime comprising cisplatin and 5-fluorouracil, the CDK4/6 inhibitor is Compound I, and the PD-L1 inhibitor is atezolizumab. In one embodiment, the chemotherapeutic agent is a combination therapeutic regime comprising cisplatin and gemcitabine, the CDK4/6 inhibitor is Compound I, and the PD-L1 inhibitor is atezolizumab. In one embodiment, the chemotherapeutic agent is doxorubicin, the CDK4/6 inhibitor is Compound I, and the PD-L1 inhibitor is atezolizumab. In one embodiment, the chemotherapeutic agent is cyclophosphamide, the CDK4/6 inhibitor is Compound I, and the PD-L1 inhibitor is atezolizumab. In one embodiment, the chemotherapeutic agent is paclitaxel, the CDK4/6 inhibitor is Compound I, and the PD-L1 inhibitor is atezolizumab. In one embodiment, the chemotherapeutic agent is oxaliplatin, the CDK4/6 inhibitor is Compound I, and the PD-L1 inhibitor is atezolizumab.

In one embodiment, the subject has colorectal cancer and is being administered a chemotherapeutic agent selected from the group consisting of 5-fluorouracil, capecitabine, irinotecan, oxaliplatin, trifluridinen, oxaliplatin, and tipiracil, or a combination thereof, in combination with a CDK4/6 inhibitor and an immune checkpoint inhibitor. In one embodiment, the CDK4/6 inhibitor is Compound I or Compound II. In one embodiment, the immune checkpoint inhibitor is a CTLA-4 inhibitor, PD-1 inhibitor, or PD-L1 inhibitor. In one embodiment, the immune checkpoint inhibitor is a PD-L1 inhibitor selected from durvalumab, avelumab, and atezolizumab. In one embodiment, the PD-L1 inhibitor is atezolizumab. In one embodiment, the chemotherapeutic agent is 5-fluorouracil, the CDK4/6 inhibitor is Compound I, and the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab. In one embodiment, the chemotherapeutic agent is capecitabine, the CDK4/6 inhibitor is Compound I, and the PD-L1 inhibitor is atezolizumab. In one embodiment, the chemotherapeutic agent is a combination therapeutic regime comprising trifluridinen and tipiracil, the CDK4/6 inhibitor is Compound I, and the PD-L1 inhibitor is atezolizumab. In one embodiment, the chemotherapeutic agent is irinotecan, the CDK4/6 inhibitor is Compound I, and the PD-L1 inhibitor is atezolizumab. In one embodiment, the chemotherapeutic agent is oxaliplatin, the CDK4/6 inhibitor is Compound I, and the PD-L1 inhibitor is atezolizumab.

In one embodiment, the subject has castration-resistant prostate cancer and is administered a chemotherapeutic agent selected from the group consisting of docetaxel, cabazitaxel, mitoxantrone, and estramustine, or a combination thereof in combination with Compound I and atezolizumab. In one embodiment, the chemotherapeutic agent is docetaxel. In one embodiment, the chemotherapeutic agent is cabazitaxel. In one embodiment, the chemotherapeutic agent is mitoxantrone. In one embodiment, the chemotherapeutic agent is estramustine. In one embodiment, the CDK4/6 inhibitor is Compound I or Compound II. In one embodiment, the immune checkpoint inhibitor is a CTLA-4 inhibitor, PD-1 inhibitor, or PD-L1 inhibitor. In one embodiment, the immune checkpoint inhibitor is a PD-L1 inhibitor selected from durvalumab, avelumab, and atezolizumab. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab. In one embodiment, the chemotherapeutic agent is docetaxel, the CDK4/6 inhibitor is Compound I, and the PD-L1 inhibitor is atezolizumab. In one embodiment, the chemotherapeutic agent is cabazitaxel, the CDK4/6 inhibitor is Compound I, and the PD-L1 inhibitor is atezolizumab. In one embodiment, the chemotherapeutic agent is mitoxantrone, the CDK4/6 inhibitor is Compound I, and the PD-L1 inhibitor is atezolizumab. In one embodiment, the chemotherapeutic agent is estramustine, the CDK4/6 inhibitor is Compound I, and the PD-L1 inhibitor is atezolizumab.

In one embodiment, the subject has PD-L1-expressing tumors and is being administered a chemotherapeutic agent selected from the group consisting of carboplatin, cisplatin, gemcitabine, etoposide, 5-fluorouracil, paclitaxel, oxaliplatin, and topotecan, or a combination thereof, in combination with a CDK4/6 inhibitor and an immune checkpoint inhibitor. In one embodiment, the CDK4/6 inhibitor is Compound I or Compound II. In one embodiment, the immune checkpoint inhibitor is a CTLA-4 inhibitor, PD-1 inhibitor, or PD-L1 inhibitor. In one embodiment, the immune checkpoint inhibitor is a PD-L1 inhibitor selected from durvalumab, avelumab, and atezolizumab. In one embodiment, the PD-L1 inhibitor is atezolizumab. In one embodiment, the chemotherapeutic agent is etoposide, the CDK4/6 inhibitor is Compound I, and the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab. In one embodiment, the chemotherapeutic agent is carboplatin, the CDK4/6 inhibitor is Compound I, and the PD-L1 inhibitor is atezolizumab. In one embodiment, the chemotherapeutic agent is a combination therapeutic regime comprising carboplatin and etoposide, the CDK4/6 inhibitor is Compound I, and the PD-L1 inhibitor is atezolizumab. In one embodiment, the chemotherapeutic agent is cisplatin, the CDK4/6 inhibitor is Compound I, and the PD-L1 inhibitor is atezolizumab. In one embodiment, the chemotherapeutic agent is topotecan, the CDK4/6 inhibitor is Compound I, and the PD-L1 inhibitor is atezolizumab. In one embodiment, the chemotherapeutic agent is oxaliplatin, the CDK4/6 inhibitor is Compound I, and the PD-L1 inhibitor is atezolizumab. In one embodiment, the chemotherapeutic agent is a combination therapeutic regime comprising cisplatin and 5-fluorouracil, the CDK4/6 inhibitor is Compound I, and the PD-L1 inhibitor is atezolizumab. In one embodiment, the chemotherapeutic agent is doxorubicin, the CDK4/6 inhibitor is Compound I, and the PD-L1 inhibitor is atezolizumab.

In one embodiment, the subject has gastric cancer and is being administered a chemotherapeutic agent selected from the group consisting of 5-fluorouracil, capecitabine, carboplatin, cisplatin, docetaxel, epirubicin, irinotecan, oxaliplatin, paclitaxel, or a combination thereof, in combination with a CDK4/6 inhibitor and an immune checkpoint inhibitor. In one embodiment, the CDK4/6 inhibitor is Compound I or Compound II. In one embodiment, the immune checkpoint inhibitor is a CTLA-4 inhibitor, PD-1 inhibitor, or PD-L1 inhibitor. In one embodiment, the immune checkpoint inhibitor is a PD-L1 inhibitor selected from durvalumab, avelumab, and atezolizumab. In one embodiment, the PD-L1 inhibitor is atezolizumab. In one embodiment, the chemotherapeutic agent is 5-fluorouracil, the CDK4/6 inhibitor is Compound I, and the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab. In one embodiment, the chemotherapeutic agent is capecitabine, the CDK4/6 inhibitor is Compound I, and the PD-L1 inhibitor is atezolizumab. In one embodiment, the chemotherapeutic agent is a combination therapeutic regime comprising epirubicin, cisplatin and 5-fluorouracil, the CDK4/6 inhibitor is Compound I, and the PD-L1 inhibitor is atezolizumab. In one embodiment, the chemotherapeutic agent is carboplatin, the CDK4/6 inhibitor is Compound I, and the PD-L1 inhibitor is atezolizumab. In one embodiment, the chemotherapeutic agent is cisplatin, the CDK4/6 inhibitor is Compound I, and the PD-L1 inhibitor is atezolizumab. In one embodiment, the chemotherapeutic agent is docetaxel, the CDK4/6 inhibitor is Compound I, and the PD-L1 inhibitor is atezolizumab. In one embodiment, the chemotherapeutic agent is epirubicin, the CDK4/6 inhibitor is Compound I, and the PD-L1 inhibitor is atezolizumab. In one embodiment, the chemotherapeutic agent is a combination therapeutic regime comprising carboplatin and paclitaxel, the CDK4/6 inhibitor is Compound I, and the PD-L1 inhibitor is atezolizumab. In one embodiment, the chemotherapeutic agent is irinotecan, the CDK4/6 inhibitor is Compound I, and the PD-L1 inhibitor is atezolizumab. In one embodiment, the chemotherapeutic agent is oxaliplatin, the CDK4/6 inhibitor is Compound I, and the PD-L1 inhibitor is atezolizumab. In one embodiment, the chemotherapeutic agent is paclitaxel, the CDK4/6 inhibitor is Compound I, and the PD-L1 inhibitor is atezolizumab.

In one embodiment, the subject has mesothelioma and is being administered a chemotherapeutic agent selected from the group consisting of carboplatin, cisplatin, oxaliplatin, gemcitabine, alimta, onconase and navelbine, or a combination thereof, in combination with a CDK4/6 inhibitor and an immune checkpoint inhibitor. In one embodiment, the CDK4/6 inhibitor is Compound I or Compound II. In one embodiment, the immune checkpoint inhibitor is a CTLA-4 inhibitor, PD-1 inhibitor, or PD-L1 inhibitor. In one embodiment, the immune checkpoint inhibitor is a PD-L1 inhibitor selected from durvalumab, avelumab, and atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab. In one embodiment, the PD-L1 inhibitor is atezolizumab. In one embodiment, the chemotherapeutic agent is carboplatin, the CDK4/6 inhibitor is Compound I, and the PD-L1 inhibitor is atezolizumab. In one embodiment, the chemotherapeutic agent is cisplatin, the CDK4/6 inhibitor is Compound I, and the PD-L1 inhibitor is atezolizumab. In one embodiment, the chemotherapeutic agent is gemcitabine, the CDK4/6 inhibitor is Compound I, and the PD-L1 inhibitor is atezolizumab. In one embodiment, the chemotherapeutic agent is alimta, the CDK4/6 inhibitor is Compound I, and the PD-L1 inhibitor is atezolizumab. In one embodiment, the chemotherapeutic agent is a combination therapeutic regime comprising cisplatin and alimta, the CDK4/6 inhibitor is Compound I, and the PD-L1 inhibitor is atezolizumab. In one embodiment, the chemotherapeutic agent is onconase, the CDK4/6 inhibitor is Compound I, and the PD-L1 inhibitor is atezolizumab. In one embodiment, the chemotherapeutic agent is navelbine, the CDK4/6 inhibitor is Compound I, and the PD-L1 inhibitor is atezolizumab. In one embodiment, the chemotherapeutic agent is oxaliplatin, the CDK4/6 inhibitor is Compound I, and the PD-L1 inhibitor is atezolizumab.

In one embodiment, the subject has ovarian cancer and is being administered a chemotherapeutic agent selected from the group consisting of carboplatin, oxaliplatin, cisplatin, doxorubicin, 5-fluorouracil, paclitaxel, cyclophosphamide, gemcitabine or a combination thereof, in combination with a CDK4/6 inhibitor and an immune checkpoint inhibitor. In one embodiment, the CDK4/6 inhibitor is Compound I or Compound II. In one embodiment, the immune checkpoint inhibitor is a CTLA-4 inhibitor, PD-1 inhibitor, or PD-L1 inhibitor. In one embodiment, the immune checkpoint inhibitor is a PD-L1 inhibitor selected from durvalumab, avelumab, and atezolizumab. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab. In one embodiment, the chemotherapeutic agent is carboplatin, the CDK4/6 inhibitor is Compound I, and the PD-L1 inhibitor is atezolizumab. In one embodiment, the chemotherapeutic agent is cisplatin, the CDK4/6 inhibitor is Compound I, and the PD-L1 inhibitor is atezolizumab. In one embodiment, the chemotherapeutic agent is a combination therapeutic regime comprising cisplatin and 5-fluorouracil, the CDK4/6 inhibitor is Compound I, and the PD-L1 inhibitor is atezolizumab. In one embodiment, the chemotherapeutic agent is a combination therapeutic regime comprising cisplatin and gemcitabine, the CDK4/6 inhibitor is Compound I, and the PD-L1 inhibitor is atezolizumab. In one embodiment, the chemotherapeutic agent is doxorubicin, the CDK4/6 inhibitor is Compound I, and the PD-L1 inhibitor is atezolizumab. In one embodiment, the chemotherapeutic agent is cyclophosphamide, the CDK4/6 inhibitor is Compound I, and the PD-L1 inhibitor is atezolizumab. In one embodiment, the chemotherapeutic agent is paclitaxel, the CDK4/6 inhibitor is Compound I, and the PD-L1 inhibitor is atezolizumab. In one embodiment, the chemotherapeutic agent is oxaliplatin, the CDK4/6 inhibitor is Compound I, and the PD-L1 inhibitor is atezolizumab.

In one embodiment, the subject has head and neck cancer and is being administered a chemotherapeutic agent selected from the group consisting of carboplatin, oxaliplatin, cisplatin, 5-fluoruracil, gemcitabine, and docetaxel, or a combination thereof, in combination with a CDK4/6 inhibitor and an immune checkpoint inhibitor. In one embodiment, the CDK4/6 inhibitor is Compound I or Compound II. In one embodiment, the immune checkpoint inhibitor is a CTLA-4 inhibitor, PD-1 inhibitor, or PD-L1 inhibitor. In one embodiment, the immune checkpoint inhibitor is a PD-L1 inhibitor selected from durvalumab, avelumab, and atezolizumab. In one embodiment, the PD-L1 inhibitor is atezolizumab. In one embodiment, the immune checkpoint inhibitor is a CTLA-4 inhibitor selected from a group consisting of ipilimumab (Yervoy®), tremelimumab, AGEN1884, and AGEN2041. In one embodiment, the immune checkpoint inhibitor is a PD-1 inhibitor selected from a group consisting of nivolumab (Opdivo®), pembrolizumab (Keytruda®), and pidilizumab. In one embodiment, the chemotherapeutic agent is carboplatin, the CDK4/6 inhibitor is Compound I, and the PD-L1 inhibitor is atezolizumab. In one embodiment, the chemotherapeutic agent is cisplatin, the CDK4/6 inhibitor is Compound I, and the PD-L1 inhibitor is atezolizumab. In one embodiment, the chemotherapeutic agent is 5-fluorouracil, the CDK4/6 inhibitor is Compound I, and the PD-L1 inhibitor is atezolizumab. In one embodiment, the chemotherapeutic agent is gemcitabine, the CDK4/6 inhibitor is Compound I, and the PD-L1 inhibitor is atezolizumab. In one embodiment, the chemotherapeutic agent is oxaliplatin, the CDK4/6 inhibitor is Compound I, and the PD-L1 inhibitor is atezolizumab. In one embodiment, the chemotherapeutic agent is docetaxel, the CDK4/6 inhibitor is Compound I, and the PD-L1 inhibitor is atezolizumab.

Also contemplated herein is the administration of a CDK4/6 inhibitor in combination with an immune checkpoint inhibitor, for example a CTLA-4 inhibitor, PD-1 inhibitor, or PD-L1 inhibitor, wherein the CDK4/6 inhibitor/ checkpoint inhibitor combination is administered to maintain immune effector cell response following the end of a CDK4/6 inhibitor/chemotherapeutic agent/immune checkpoint treatment regimen. For example, following the completion of a CDK4/6 inhibitor/chemotherapeutic agent/immune checkpoint inhibitor treatment regimen, CDK4/6 inhibitor in combination with the immune checkpoint inhibitor can be administered to the subject at periodic intervals for the maintenance of the immune effector cell response. In one embodiment, the maintenance regimen of CDK4/6 inhibitor/immune checkpoint inhibitor is administered at least one or more times following cessation of the original therapeutic regimen. In one embodiment, the maintenance regimen is administered once a week, twice a month, once a month, once every six weeks, or from time to time as necessary. In one embodiment, the CDK4/6 inhibitor is Compound I and the immune checkpoint inhibitor is a PD-L1 inhibitor selected from durvalumab, avelumab, and atezolizumab. In one embodiment, the CDK4/6 inhibitor is Compound I and the PD-L1 inhibitor is atezolizumab. In one embodiment, the CDK4/6 inhibitor is Compound I and the immune checkpoint inhibitor is a CTLA-4 inhibitor. In one embodiment, the CDK4/6 inhibitor is Compound I and the immune checkpoint inhibitor is a PD-1 inhibitor.

Further contemplated herein is the administration of an immune checkpoint inhibitor, for example a PD-L1 inhibitor, wherein the immune checkpoint inhibitor is administered to maintain immune effector cell response following the end of a CDK4/6 inhibitor/chemotherapeutic agent/ immune checkpoint inhibitor treatment regimen. For example, following the completion of a CDK4/6 inhibitor/ chemotherapeutic agent/immune checkpoint inhibitor treatment regimen, the immune checkpoint inhibitor can be administered to the subject at periodic intervals for the maintenance of the immune effector cell response. In one embodiment, the maintenance regimen of the immune checkpoint inhibitor is administered at least one or more times following cessation of the original therapeutic regimen. In one embodiment, the maintenance regimen is administered once a week, twice a month, once a month, once every six weeks, or from time to time. In one embodiment, the immune checkpoint inhibitor is a PD-L1 inhibitor selected from durvalumab, avelumab, and atezolizumab. In one embodiment, the PD-L1 inhibitor is atezolizumab. In one embodiment, the CDK4/6 inhibitor is Compound I and the immune checkpoint inhibitor is a CTLA-4 inhibitor. In one embodiment, the CDK4/6 inhibitor is Compound I and the immune checkpoint inhibitor is a PD-1 inhibitor.

Pharmaceutical Compositions and Dosage Forms

The active compounds described herein for use in the methods described herein, or its salt, isotopic analog, or prodrug can be administered in an effective amount to a subject using any suitable approach which achieves the desired therapeutic result. The amount and timing of the active compounds administered will, of course, be dependent on the subject being treated, the instructions of the supervising medical specialist, on the time course of the exposure, on the manner of administration, on the pharmacokinetic properties of the particular active compound, and on the judgment of the prescribing physician. Thus, because of host to host variability, the dosages given below are a guideline and the physician can titrate doses of the active compounds to achieve the treatment that the physician considers appropriate for the host. In considering the degree of treatment desired, the physician can balance a variety of factors such as age and weight of the host, presence of preexisting disease, as well as presence of other diseases. General administration dosages for CDK4/6 inhibitors such as Compound I have been previously described in WO 2016/126889, incorporated herein by its entirety.

The pharmaceutical composition may be formulated as any pharmaceutically useful form, e.g., as an aerosol, a cream, a gel, a pill, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution. Some dosage forms, such as tablets and capsules, are subdivided into suitably sized unit doses containing appropriate quantities of the active components, e.g., an effective amount to achieve the desired purpose.

The therapeutically effective dosage of any active compound described herein will be determined by the health care practitioner depending on the condition, size and age of the patient as well as the route of delivery. In one non-limited embodiment, a dosage from about 0.1 to about 200 mg/kg has therapeutic efficacy, with all weights being calculated based upon the weight of the active compound, including the cases where a salt is employed. In some embodiments, the dosage may be the amount of compound needed to provide a serum concentration of the active compound of up to about 10 nM, 50 nM, 100 nM, 200 nM, 300 nM, 400 nM, 500 nM, 600 nM, 700 nM, 800 nM, 900 nM, 1 µM, 5 µM, 10 µM, 20 µM, 30 µM, or 40 µM.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples of dosage forms with at least 5, 10, 15, 20, 25, 50, 100, 200, 250, 300, 400, 500, 600, 700, or 750 mg of active compound, or its salt. The pharmaceutical composition may also include a molar ratio of the active compound and an additional active agent, in a ratio that achieves the desired results.

In one embodiment, the CDK4/6 inhibitor administered is Compound I, which is administered at a dosage of about 180 mg/m$^2$ to about 280 mg/m$^2$. In one embodiment, Compound I is administered at about 180, 185, 190, 195, 200, 205, 210, 215, 220, 225, 230, 235, 240, 245, 250, 255, 260, 265, 270, 275, or about 280 mg/m$^2$. In one embodiment, Compound I is administered at a dose of about 200 mg/m$^2$. In one embodiment, Compound I is administered at a dose of about 240 mg/m$^2$.

In one embodiment, the CDK4/6 inhibitor administered is Compound II, which is administered at a dosage of about 180 mg/m$^2$ to about 280 mg/m$^2$. In one embodiment, Compound II is administered at about 180, 185, 190, 195, 200, 205, 210, 215, 220, 225, 230, 235, 240, 245, 250, 255, 260, 265, 270, 275, or about 280 mg/m$^2$. In one embodiment, Compound II is administered at a dose of about 200 mg/m$^2$. In one embodiment, Compound II is administered at a dose of about 240 mg/m$^2$.

In one embodiment, the CDK4/6 inhibitor administered is Compound III, which is administered at a dosage of about 180 mg/m$^2$ to about 280 mg/m$^2$. In one embodiment, Compound III is administered at about 180, 185, 190, 195, 200, 205, 210, 215, 220, 225, 230, 235, 240, 245, 250, 255, 260, 265, 270, 275, or about 280 mg/m$^2$. In one embodiment, Compound III is administered at a dose of about 200 mg/m$^2$. In one embodiment, Compound III is administered at a dose of about 240 mg/m$^2$.

In one embodiment, the CDK4/6 inhibitor administered is Compound IV, which is administered at a dosage of about 180 mg/m$^2$ to about 280 mg/m$^2$. In one embodiment, Compound IV is administered at about 180, 185, 190, 195, 200, 205, 210, 215, 220, 225, 230, 235, 240, 245, 250, 255, 260, 265, 270, 275, or about 280 mg/m$^2$. In one embodiment, Compound IV is administered at a dose of about 200 mg/m$^2$. In one embodiment, Compound IV is administered at a dose of about 240 mg/m$^2$.

Compounds disclosed herein or used as described herein may be administered orally, topically, parenterally, by inhalation or spray, sublingually, via implant, including ocular implant, transdermally, via buccal administration, rectally, as an ophthalmic solution, injection, including ocular injection, intravenous, intramuscular, inhalation, intra-aortal, intracranial, subdermal, intraperitoneal, subcutaneous, transnasal, sublingual, or rectal or by other means, in dosage unit formulations containing conventional pharmaceutically acceptable carriers. For ocular delivery, the compound can be administered, as desired, for example, via intravitreal, intrastromal, intracameral, sub-tenon, sub-retinal, retro-bulbar, peribulbar, suprachorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device.

In accordance with the presently disclosed methods, an oral administration can be in any desired form such as a solid, gel or liquid, including a solution, suspension, or emulsion. In some embodiments, the compounds or salts are administered by inhalation, intravenously, or intramuscularly as a liposomal suspension. When administered through inhalation the active compound or salt may be in the form of a plurality of solid particles or droplets having any desired particle size, and for example, from about 0.01, 0.1 or 0.5 to about 5, 10, 20 or more microns, and optionally from about 1 to about 2 microns. Compounds as disclosed in the present invention have demonstrated good pharmacokinetic and pharmacodynamics properties, for instance when administered by the oral or intravenous routes.

The pharmaceutical formulations can comprise an active compound described herein or a pharmaceutically acceptable salt thereof, in any pharmaceutically acceptable carrier. If a solution is desired, water may sometimes be the carrier of choice for water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and for illustration by filtration through a 0.22-micron filter. Subsequent to sterilization, the solution can be dispensed into appropriate receptacles, such as depyrogenated glass vials. The dispensing is optionally done by an aseptic method. Sterilized closures can then be placed on the vials and, if desired, the vial contents can be lyophilized.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

In addition to the active compounds or their salts, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. An antimicrobial preservative is typically employed when the formulations is placed in a vial designed for multi-dose use. The pharmaceutical formulations described herein can be lyophilized using techniques well known in the art.

For oral administration, a pharmaceutical composition can take the form of a solution suspension, tablet, pill, capsule, powder, and the like. Tablets containing various excipients such as sodium citrate, calcium carbonate and calcium phosphate may be employed along with various disintegrants such as starch (e.g., potato or tapioca starch) and certain complex silicates, together with binding agents such as polyvinylpyrrolidone, sucrose, gelatin and acacia. Additionally, lubricating agents such as magnesium stearate, sodium lauryl sulfate, and talc are often very useful for tableting purposes. Solid compositions of a similar type may be employed as fillers in soft and hard-filled gelatin capsules. Materials in this connection also include lactose or milk sugar as well as high molecular weight polyethylene glycols. When aqueous suspensions and/or elixirs are desired for oral administration, the compounds of the presently disclosed host matter can be combined with various sweetening agents, flavoring agents, coloring agents, emulsifying agents and/or suspending agents, as well as such diluents as water, ethanol, propylene glycol, glycerin and various like combinations thereof.

In yet another embodiment of the host matter described herein, there are provided injectable, stable, sterile formulations comprising an active compound as described herein, or a salt thereof, in a unit dosage form in a sealed container. The compound or salt is provided in the form of a lyophilizate, which is capable of being reconstituted with a suitable pharmaceutically acceptable carrier to form liquid formulation suitable for injection thereof into a host. When the compound or salt is substantially water-insoluble, a sufficient amount of emulsifying agent, which is physiologically acceptable, can be employed in sufficient quantity to emulsify the compound or salt in an aqueous carrier. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound can be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques. The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol by inhalation. These formulations comprise a solution or suspension of a desired compound described herein or a salt thereof, or a plurality of solid particles of the compound or salt. The desired formulations can be placed in a small chamber and nebulized. Nebulization can be accomplished by compressed air or by ultrasonic energy to form a plurality of liquid droplets or solid particles comprising the compounds or salts. The liquid droplets or solid particles may for example have a particle size in the range of about 0.5 to about 10 microns, and optionally from about 0.5 to about 5 microns. In one embodiment, the solid particles provide for controlled release through the use of a degradable polymer. The solid particles can be obtained by processing the solid compound or a salt thereof, in any appropriate manner known in the art, such as by micronization. Optionally, the size of the solid particles or droplets can be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

Pharmaceutical formulations also are provided which provide a controlled release of a compound described herein, including through the use of a degradable polymer, as known in the art.

When the pharmaceutical formulations suitable for administration as an aerosol is in the form of a liquid, the formulations can comprise a water-soluble active compound in a carrier that comprises water. A surfactant can be present, which lowers the surface tension of the formulations sufficiently to result in the formation of droplets within the desired size range when hosted to nebulization.

The term "pharmaceutically acceptable salts" as used herein refers to those salts which are, within the scope of sound medical judgment, suitable for use in contact with hosts (e.g., human hosts) without undue toxicity, irritation, allergic response, and the like, commensurate with a reasonable benefit/risk ratio, and effective for their intended use, as well as the zwitterionic forms, where possible, of the compounds of the presently disclosed host matter.

Thus, the term "salts" refers to the relatively non-toxic, inorganic and organic acid addition salts of the presently disclosed compounds. These salts can be prepared during the final isolation and purification of the compounds or by separately reacting the purified compound in its free base form with a suitable organic or inorganic acid and isolating the salt thus formed. Basic compounds are capable of forming a wide variety of different salts with various inorganic and organic acids. Acid addition salts of the basic compounds are prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms in certain physical properties such as solubility in polar solvents. Pharmaceutically acceptable base addition salts may be formed with metals or amines, such as alkali and alkaline earth metal hydroxides, or of organic amines. Examples of metals used as cations, include, but are not limited to, sodium, potassium, magnesium, calcium, and the like. Examples of suitable amines include, but are not limited to, N,N'-dibenzylethylenediamine, chloroprocaine, choline, diethanolamine, ethylenediamine, N-methylglucamine, and procaine. The base addition salts of acidic compounds are prepared by contacting the free acid form with a sufficient amount of the desired base to produce the salt in the conventional manner. The free acid form can be regenerated by contacting the salt form with an acid and isolating the free acid in a conventional manner. The free acid forms may differ from their respective salt forms somewhat in certain physical properties such as solubility in polar solvents.

Salts can be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts can also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts can include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See, for example, Berge et al., J. Pharm. Sci., 1977, 66, 1-19, which is incorporated herein by reference.

EXAMPLES

Figure 2:
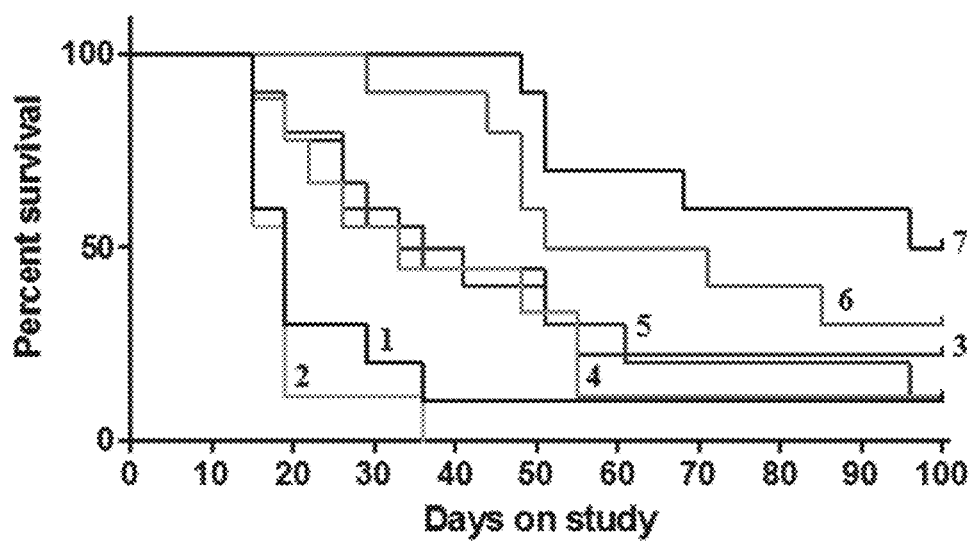
FIG. 2 depicts overall survival over 100 days in a syngeneic MC38 mouse tumor model following treatment with (1) vehicle, (2) Compound I (100 mg/kg), (3) oxaliplatin, (4) anti-mouse PD-L1, (5) Compound I+oxaliplatin, (6) oxaliplatin (administered on days 1, 8, and 15) and anti-mouse PD-L1 (administered on days 1, 4, 8, and 11), and (7) Compound I+oxaliplatin (administered on days 1, 8, 15)+anti-mouse PD-L1 (administered on days 1, 4, 8, and 11). The x-axis represents study length measured in days and the y-axis represents percent survival.

Example 1. Use of a CDK4/6 Inhibitor Increases Efficacy of Anti-Tumor Response in Combination with Oxaliplatin and an Anti-PD-L1 Compound The Effect of Using a CDK4/6 inhibitor (Compound I) in combination with the chemotherapeutic agent oxaliplatin and the anti-mouse PD-L1 clone 10F.9G2 (BioXcell Cat # BE0101) in a syngeneic MC38 mouse tumor model was studied. The study, conducted over the course of 100 days, measured tumor growth and overall survival of the mice. Tumor growth is depicted in FIG. 1 and overall survival is depicted in FIG. 2. The arms of the study included the following:

1) vehicle
2) Compound I (100 mg/kg)
3) oxaliplatin
4) anti-mouse PD-L 1 (clone 10F.9G2)
5) Compound I+oxaliplatin
6) oxaliplatin (administered on days 1, 8, and 15) and anti-mouse PD-L1 (clone 10F.9G2) (administered on days 1, 4, 8, and 11)
7) Compound I+oxaliplatin (administered on days 1, 8, 15)+anti-mouse PD-L1 (administered on days 1, 4, 8, and) where Compound I is administered 30 minutes prior to Oxaliplatin In mice treated with oxaliplatin and anti-mouse PD-L1 (Arm 6), a 30% complete response rate was reported and in mice treated with Compound I, oxaliplatin and anti-mouse PD-L1 (Arm 7), a 60% complete response rate was reported.

The median overall survival for mice treated with Compound I, oxaliplatin, and anti-mouse PD-L1 (Arm 7) was 98 days and the median overall survival for mice treated with oxaliplatin and anti-mouse PD-L1 (Arm 6) was 61 days.

These results demonstrate that the addition of a CDK4/6 inhibitor, in this case Compound I, to a chemotherapeutic/PD-L1 inhibitor combination treatment significantly improves anti-tumor activity. Specifically, twice as many mice treated with the CDK4/6 inhibitor/chemotherapeutic agent/PD-L1 inhibitor treatment regimen had a complete response (CRs) when compared to chemotherapeutic agent/PD-L1 treatment; 6/10 CRs vs 3/10 CRs, respectively. In addition, the CRs were durable and without any evidence of recurrence at 100 days. Furthermore, CDK4/6 inhibitor/chemotherapeutic agent/PD-L1 inhibitor treatment regimen caused a 60% increase in overall survival (OS) compared to mice treated with chemotherapeutic agent/PD-L1 inhibitor; median OS for CDK4/6 inhibitor/chemotherapeutic agent/PD-L1 inhibitor treatment group was 98 days compared to 61 days (HR, 0.53) for the chemotherapeutic agent/PD-L1 inhibitor treatment group.

Taken together, this demonstrates that the use of a short-acting CDK4/6 inhibitor preserves immune function during chemotherapy and enhances the anti-tumor activity of chemotherapy/checkpoint inhibitor combination therapy.

Example 2. Compound I Increases Efficacy of Anti-Tumor Response in Combination with Oxaliplatin and PD-L1

Figure 3:
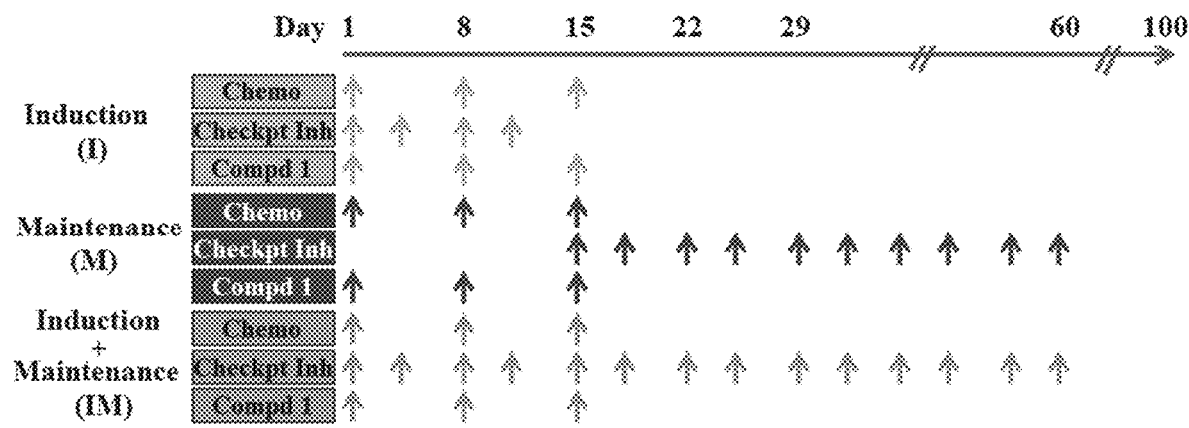
FIG. 3 depicts the dosing schedule for xenograft studies as described in Example 2 and Example 3. Mice were given one of the dosing schedules of chemotherapy/checkpoint inhibitor with or without Compound I. Specifically, the checkpoint inhibitor was either given only during chemotherapy treatment (I), only after chemotherapy treatment (M) or during and after chemotherapy treatment (IM) until complete response or animal termination. In experimental cohorts, Compound I was given 30 minutes prior to chemotherapy treatment.

Anti-tumor activity of Compound I in combination with PD-L1 (clone 10F.9G2) and oxaliplatin was evaluated in the MC38 syngeneic murine colon carcinoma model. For all xenograft studies, nine-week old female C57BL/6 mice (C57BL/6NCrl) were implanted with MC38 tumor cells and treatment was initiated when mean tumor volume was approximately 100 mm$^3$. A summary of treatment combinations and schedules is shown in FIG. 3.

Briefly, Compound I (100 mg/kg) and oxaliplatin (10 mg/kg) were administered intraperitoneally (IP) once weekly for three doses and the checkpoint inhibitor administration was varied as depending on the dosing schedule. In the Induction (I) dosing schedule, mouse anti-PD-L1 (100 µg/animal, IP) was given twice weekly for two weeks starting on Day 1 and ending on Day 15. In the Maintenance (M) dosing schedule, mouse anti-PD-L1 (100 µg/animal, IP) was given twice weekly starting on Day 15 and continuing through the end of study. In the Induction+Maintenance (IM) dosing schedule, mouse anti-PD-L1 (100 µg/animal, IP) was given twice weekly starting on Day 1 and continuing through the end of study.

Figure 4:
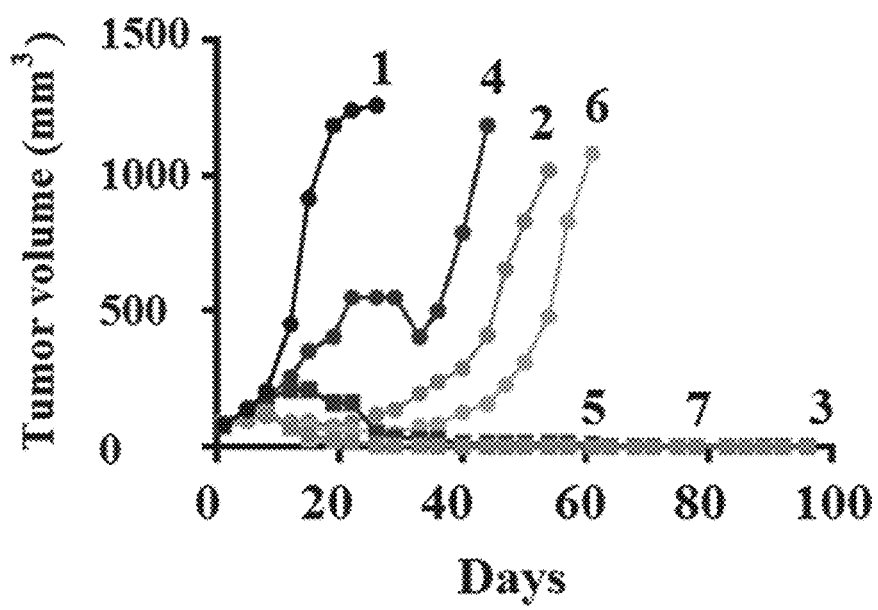
FIG. 4 depicts tumor growth rate over 100 days in a syngeneic MC38 mouse tumor model following treatment with (1) vehicle, (2) oxaliplatin+mouse anti-PD-LI during the (IM) dosing schedule, (3) Compound I+oxaliplatin+mouse anti-PD-LI during the (IM) dosing schedule, (4) oxaliplatin+mouse anti-PD-LI during the (M) dosing schedule, (5) Compound I+oxaliplatin+mouse anti-PD-LI during the (M) dosing schedule, (6) oxaliplatin+mouse anti-PD-LI during the (I) dosing schedule, and (7) Compound I+oxaliplatin+mouse anti-PD-LI during the (I) dosing schedule as described in Example 2. The x-axis represents study length measured in days and the y-axis represents tumor volume measured in $mm^3$.
Figure 5:
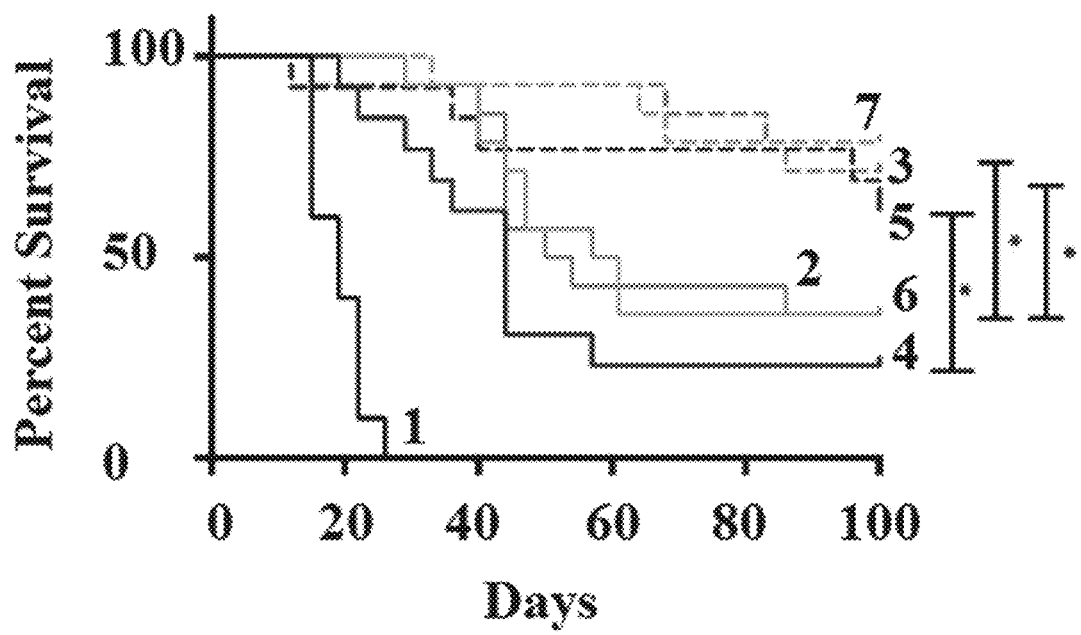
FIG. 5 depicts overall survival 100 days in a syngeneic MC38 mouse tumor model following treatment with (1) vehicle, (2) oxaliplatin+mouse anti-PD-LI during the (IM) dosing schedule, (3) Compound I+oxaliplatin+mouse anti-PD-LI during the (IM) dosing schedule, (4) oxaliplatin+mouse anti-PD-LI during the (M) dosing schedule, (5) Compound I+oxaliplatin+mouse anti-PD-LI during the (M) dosing schedule, (6) oxaliplatin+mouse anti-PD-LI during the (I) dosing schedule, and (7) Compound I+oxaliplatin+mouse anti-PD-LI during the (I) dosing schedule as described in Example 2. The x-axis represents study length measured in days and the y-axis represents percent survival. * equals p≤0.05.

Single, two, and three drug combinations were tested and Compound I was administered 30 minutes prior to chemotherapy treatment. Complete response (CR) and partial response (PR) were calculated using standard Charles River Laboratories (CRL; RTP, NC) criteria. Body weight (BW) and health were monitored, and tumor volume was measured twice weekly. The individual tumor volume endpoint was 1000 mm³ or Day 100, whichever came first. The arms of the study included the following:

1) vehicle
2) Compound I+anti-PD-L1 (clone 10F.9G2), IM dosing schedule
3) Compound I+Oxaliplatin+anti-PD-L1 (clone 10F.9G2), IM dosing schedule
4) Oxaliplatin+anti-mouse PD-L1 (clone 10F.9G2), M dosing schedule
5) Compound I+oxaliplatin+anti-mouse PD-L1 (clone 10F.9G2), M dosing schedule
6) oxaliplatin+anti-mouse PD-L1 (clone 10F.9G2), I dosing schedule
7) Compound I+oxaliplatin+anti-mouse PD-L1 (clone 10F.9G2), I dosing schedule Tumor growth of mice treated with Compound I in combination with oxaliplatin and mouse anti-PD-L1 is depicted in FIG. 4. The combination of Compound I, oxaliplatin, and mouse anti-PD-L1 was more efficacious in treating tumor growth than when only oxaliplatin and mouse anti-PD-L1 were administered for all dosing schedules of the study. As shown in FIG. 5, overall survival of mice treated with Compound I in combination with oxaliplatin and mouse anti-PD-L1 resulted in improved survival. The percent survival of mice treated with Compound I, oxaliplatin, and mouse anti-PD-L 1 was significantly higher than the corresponding percent survival of mice treated with only oxaliplatin and mouse anti-PD-L1 for all three dosing schedules. Additionally, combination therapy was well tolerated and did not cause significant weight loss during and after treatment.

Table 1 summarizes the effect of Compound I in combination with oxaliplatin and mouse anti-PD-L 1 during the study of tumor growth in mice. The combination of Compound I with oxaliplatin and mouse anti-PD-L1 are shown for all dosing schedules of the study.

TABLE 1

Compound I enhances Complete Response (CR) and Overall Survival (OS) when added to Oxaliplatin and Anti-PD-L1 Combination Therapy.

| Treatment | Partial Response % | Complete Response % | Objective Response Rate % | Overall Survival (OS) |
|---|---|---|---|---|
| Vehicle (n = 20) | 0 | 5 | 5 | 19 |
| Compound I (n = 9) | 0 | 0 | 0 | 19 |
| Mouse anti-PD-L1 (n = 9) | 0 | 11 | 11 | 33 |
| Oxaliplatin (n = 9) | 0 | 22 | 22 | 36 |
| Compound I + Oxaliplatin (n = 10) | 10 | 10 | 20 | 37 |
| Oxaliplatin + Mouse anti-PD-L1 (IM) (n = 14) | 7 | 36 | 43 | 52 |
| Compound I + Oxaliplatin + Mouse anti-PD-L1 (IM) (n = 14)* | 7 | 79 | 86 | Not reached |
| Oxaliplatin + Mouse anti-PD-L1 (I) (n = 24) | 13 | 33 | 46 | 59 |
| Compound I + Oxaliplatin + Mouse anti-PD-L1 (I) (n = 24)* | 8 | 67 | 75 | Not reached |
| Oxaliplatin + Mouse anti-PD-L1 (M) (n = 13) | 0 | 15 | 15 | 44 |
| Compound I + Oxaliplatin + Mouse anti-PD-L1 (M) (n = 13)* | 8 | 62 | 70 | Not reached |

Abbreviations:
I = Induction dosing schedule;
M = Maintenance dosing schedule;
IM = Induction + Maintenance dosing schedule
*p ≤ 0.05 as measured using Fisher's exact test.

Example 3. Compound I Increases Efficacy of Anti-Tumor Response in Combination with Oxaliplatin and PD-1

Anti-tumor activity of Compound I in combination with PD-1 (clone RMP1-14 (rat IgG), BioXcell cat # BE0146) and oxaliplatin was evaluated in the MC38 syngeneic murine colon carcinoma model. For all xenograft studies, nine-week old female C57BL/6 mice (C57BL/6NCrl) were implanted with MC38 tumor cells and treatment was initiated when mean tumor volume was approximately 100 mm³. Compound I was administered in combination with oxaliplatin and anti-PD-1 according to the Induction and Maintenance (IM) dosing schedule, which is shown in FIG. 3.

Briefly, Compound I (100 mg/kg) and oxaliplatin (10 mg/kg) were administered intraperitoneally (IP) once weekly for three doses and mouse anti-PD-1 (5 mg/kg, IP) was given twice weekly starting on Day 1 and continuing through the end of study.

Figure 6:
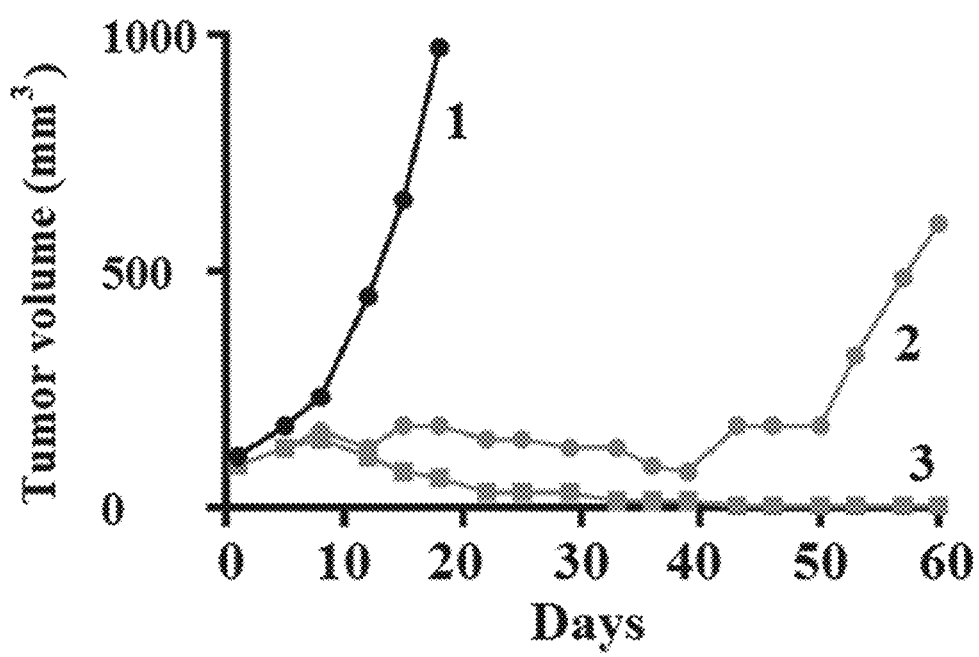
FIG. 6 depicts tumor growth rate over 60 days in a syngeneic MC38 mouse tumor model following treatment with (1) vehicle, (2) oxaliplatin+mouse anti-PD-I during the (IM) dosing schedule, and (3) Compound I+oxaliplatin+mouse anti-PD-I during the (IM) dosing schedule as described in Example 3. The x-axis represents study length measured in days and the y-axis represents tumor volume measured in $mm^3$.
Figure 7:
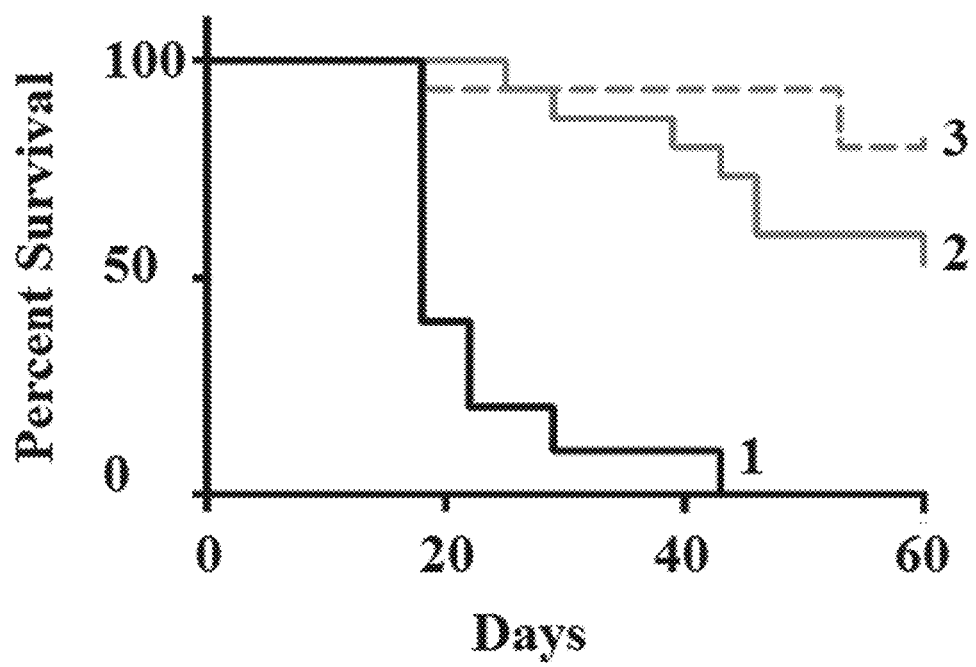
FIG. 7 depicts overall survival 60 days in a syngeneic MC38 mouse tumor model following treatment with (1) vehicle, (2) oxaliplatin+mouse anti-PD-I during the (IM) dosing schedule, and (3) Compound I+oxaliplatin+mouse anti-PD-I during the (IM) dosing schedule as described in Example 3. The x-axis represents study length measured in days and the y-axis represents percent survival.

Single, two, and three drug combinations were tested and Compound I was administered 30 minutes prior to chemotherapy treatment. Complete response (CR) and partial response (PR) were calculated using standard Charles River Laboratories (CRL; RTP, NC) criteria. Body weight (BW) and health were monitored, and tumor volume was measured twice weekly. The individual tumor volume endpoint was 1000 mm³ or Day 100, whichever came first. The arms of the study included the following:

1) vehicle
2) Oxaliplatin+anti-mouse PD-1 (clone RMP1-14 (rat IgG), BioXcell cat # BE0146), IM dosing schedule
3) Compound I+oxaliplatin+anti-mouse PD-1 (clone RMP1-14 (rat IgG), BioXcell cat # BE0146), IM dosing schedule Tumor growth of mice treated with Compound I in combination with oxaliplatin and mouse anti-PD-1 is depicted in FIG. 6. The combination of Compound I, oxaliplatin, and mouse anti-PD-1 was more efficacious in treating tumor growth than when only oxaliplatin and mouse anti-PD-1 were administered for the IM dosing schedule of the study. As shown in FIG. 7, overall survival of mice treated with Compound I in combination with oxaliplatin and mouse anti-PD-1 resulted in improved survival compared to mice treated with oxaliplatin and mouse anti-PD-1. Additionally, combination therapy was well tolerated and did not cause significant weight loss during and after treatment.

Table 2 summarizes the effect of Compound I in combination with oxaliplatin and anti-PD-1 during the study of tumor growth in mice.

TABLE 2

Compound I enhances Complete Response (CR) and Overall Survival (OS) when added to Oxaliplatin and Anti-PD-1 Combination Therapy.

| Treatment | Partial Response % | Complete Response % | Objective Response Rate % | Overall Survival (OS) |
|---|---|---|---|---|
| Vehicle (n = 10) | 0 | 0 | 0 | 18 |
| Compound I (n = 10) | 10 | 10 | 20 | 22 |
| Mouse anti-PD-1 (n = 10) | 0 | 0 | 0 | 22 |
| Oxaliplatin (n = 10) | 0 | 10 | 10 | 31 |
| Compound I + Oxaliplatin (n = 10) | 0 | 20 | 20 | 44.5 |
| Compound I + Mouse anti-PD-1 (n = 10) | 10 | 0 | 10 | 31 |
| Oxaliplatin + Mouse anti-PD-1 (IM) (n = 15) | 7 | 33 | 40 | Not reached |
| Compound I + Oxaliplatin + Mouse anti-PD-1 (IM) (n = 15) | 7 | 53 | 60 | Not reached |

Abbreviations:
I = Induction dosing schedule;
M = Maintenance dosing schedule;
IM = Induction + Maintenance dosing schedule

Example 4. Compound I Increases Efficacy of Anti-Tumor Response in Combination with 5-Fluorouracil (5-FU) and Mouse Anti-PD-L1

Anti-tumor activity of Compound I in combination with mouse anti-PD-L1 (clone 10F.9G2), and 5-flurouracil (5-FU) was evaluated in the MC38 syngeneic murine colon carcinoma model. For all xenograft studies, nine-week old female C57BL/6 mice (C57BL/6NCrl) were implanted with MC38 tumor cells and treatment was initiated when mean tumor volume was approximately 100 mm$^3$. A summary of treatment combinations and schedules is shown in FIG. 3.

Briefly, Compound I (100 mg/kg) and 5-FU (75 mg/kg) were administered intraperitoneally (IP) once weekly for three doses. As shown in FIG. 3, the dosing schedule for checkpoint inhibitor administration was varied. In the Induction (I) dosing schedule, mouse anti-PD-L1 (100 μg/animal, IP) was given twice weekly for two weeks starting on Day 1 and ending on Day 15. In the Maintenance (M) dosing schedule, mouse anti-PD-L1 (100 μg/animal, IP) was given twice weekly starting on Day 15 and continuing through the end of study. In the Induction+Maintenance (IM) dosing schedule, mouse anti-PD-L1 (100 μg/animal, IP) was given twice weekly starting on Day 1 and continuing through the end of study.

Figure 8:
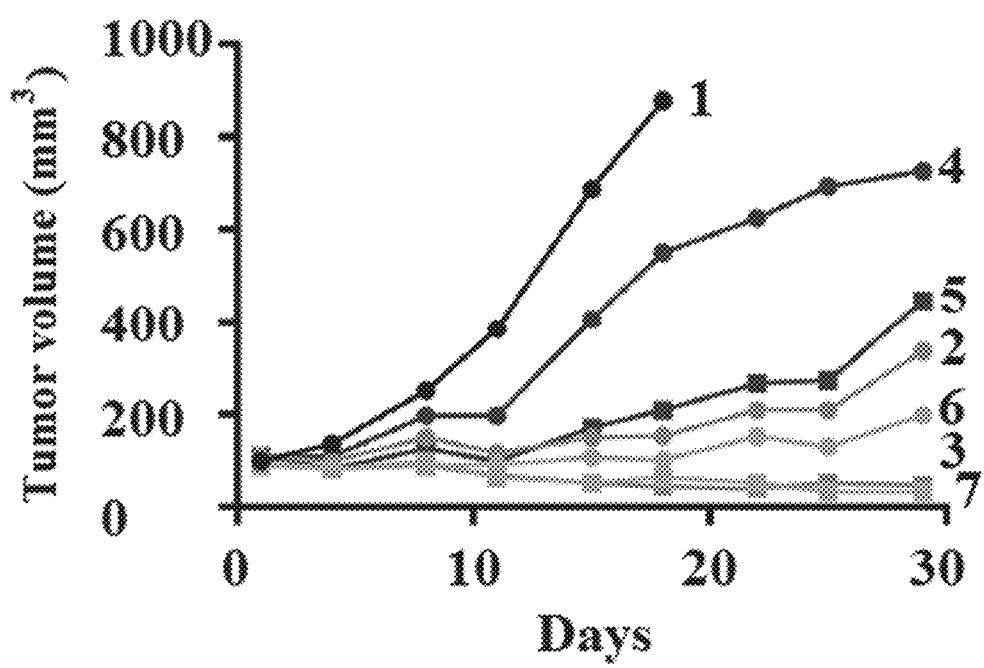
FIG. 8 depicts tumor growth rate over 30 days in a syngeneic MC38 mouse tumor model following treatment with (1) vehicle, (2) 5-FU+mouse anti-PD-LI during the (IM) dosing schedule, (3) Compound I+5-FU+mouse anti-PD-LI during the (IM) dosing schedule, (4) 5-FU+mouse anti-PD-LI during the (M) dosing schedule, (5) Compound I+5-FU+mouse anti-PD-LI during the (M) dosing schedule, (6) 5-FU+mouse anti-PD-LI during the (I) dosing schedule, and (7) Compound I+5-FU+mouse anti-PD-LI during the (I) dosing schedule as described in Example 4. The x-axis represents study length measured in days and the y-axis represents tumor volume measured in $mm^3$.
Figure 9:
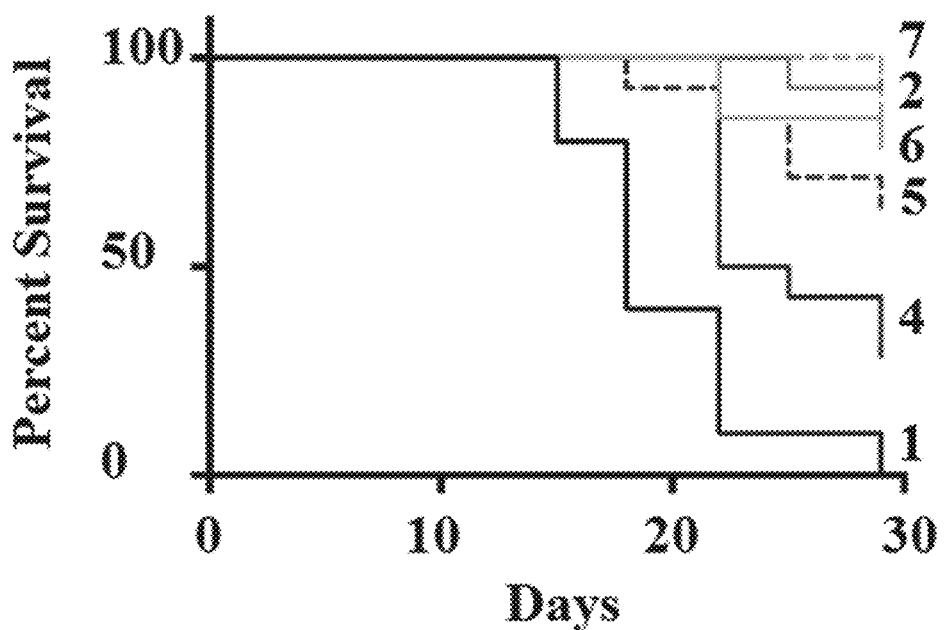
FIG. 9 depicts overall survival 30 days in a syngeneic MC38 mouse tumor model following treatment with (1) vehicle, (2) 5-FU+mouse anti-PD-LI during the (IM) dosing schedule, (3) Compound I+5-FU+mouse anti-PD-LI during the (IM) dosing schedule, (4) 5-FU+mouse anti-PD-LI during the (M) dosing schedule, (5) Compound I+5-FU+mouse anti-PD-LI during the (M) dosing schedule, (6) 5-FU+mouse anti-PD-LI during the (I) dosing schedule, and (7) Compound I+5-FU+mouse anti-PD-LI during the (I) dosing schedule as described in Example 4. The x-axis represents study length measured in days and the y-axis represents percent survival.

Single, two, and three drug combinations were tested and Compound I was administered 30 minutes prior to chemotherapy treatment. Complete response (CR) and partial response (PR) were calculated using standard Charles River Laboratories (CRL; RTP, NC) criteria. Body weight (BW) and health were monitored, and tumor volume was measured twice weekly. The individual tumor volume endpoint was 1000 mm$^3$ or Day 100, whichever came first. The arms of the study included the following:

1) vehicle
2) 5-FU+anti-PD-L1 (clone 10F.9G2), IM dosing schedule
3) Compound I+5-FU+anti-PD-L1 (clone 10F.9G2), IM dosing schedule
4) 5-FU+anti-mouse PD-L1 (clone 10F.9G2), M dosing schedule
5) Compound I+5-FU+anti-mouse PD-L1 (clone 10F.9G2), M dosing schedule
6) 5-FU+anti-mouse PD-L1 (clone 10F.9G2), I dosing schedule
7) Compound I+5-FU+anti-mouse PD-L1 (clone 10F.9G2), I dosing schedule Tumor growth of mice treated with Compound I in combination with 5-FU and mouse anti-PD-L1 is depicted in FIG. 8. The combination of Compound I, oxaliplatin, and mouse anti-PD-L1 was more efficacious in treating tumor growth than when only 5-FU and mouse anti-PD-L1 were administered for all dosing schedules of the study. As shown in FIG. 9, overall survival of mice treated with Compound I in combination with 5-FU and mouse anti-PD-L1 resulted in improved survival compared to mice treated with only 5-FU and anti-PD-L1. Additionally, combination therapy was well tolerated and did not cause significant weight loss during and after treatment.

Table 3 summarizes the effect of Compound I in combination with 5-FU and mouse anti-PD-L1 during the study of tumor growth in mice. The combination of Compound I with 5-FU and anti-PD-L1 are shown for all dosing schedules of the study.

TABLE 3

Interim Data describing the effects of Compound I when added to 5-FU and anti-PD-L1 combination therapy.

| Treatment | Partial Response % | Complete Response % | Objective Response Rate % | Progressive Disease % | Overall Survival @ D29% |
|---|---|---|---|---|---|
| Vehicle (n = 10) | 0 | 0 | 0 | 100 | 0 |
| Mouse anti-PD-L1 (n = 10) | 0 | 0 | 0 | 90 | 40 |
| 5-FU (n = 10) | 0 | 0 | 0 | 100 | 30 |
| Compound I + 5-FU (n = 10) | 0 | 0 | 0 | 90 | 50 |
| Compound I + Mouse anti-PD-L1 (IM) (n = 14) | 0 | 0 | 0 | 93 | 43 |
| 5-FU + Mouse anti-PD-L1 (IM) (n = 14) | 14 | 14 | 28 | 71 | 93 |
| Compound I + 5-FU + Mouse anti-PD-L1 (IM) (n = 14) | 29 | 14 | 43 | 36 | 93 |
| 5-FU + Mouse anti-PD-L1 (I) (n = 14) | 36 | 0 | 36 | 50 | 79 |
| Compound I + 5-FU + Mouse anti-PD-L1 (I) (n = 14) | 36 | 7 | 43 | 21 | 86 |
| 5-FU + Mouse anti-PD-L1 (M) (n = 14) | 0 | 0 | 0 | 93 | 29 |
| Compound I + 5-FU + Mouse anti-PD-L1 (M) (n = 14) | 0 | 0 | 0 | 71 | 64 |

Abbreviations:
I = Induction dosing schedule;
M = Maintenance dosing schedule;
IM = Induction + Maintenance dosing schedule
Progressive disease is defined as the percent of tumors that have doubled in size by Day 29.

Figure 10:
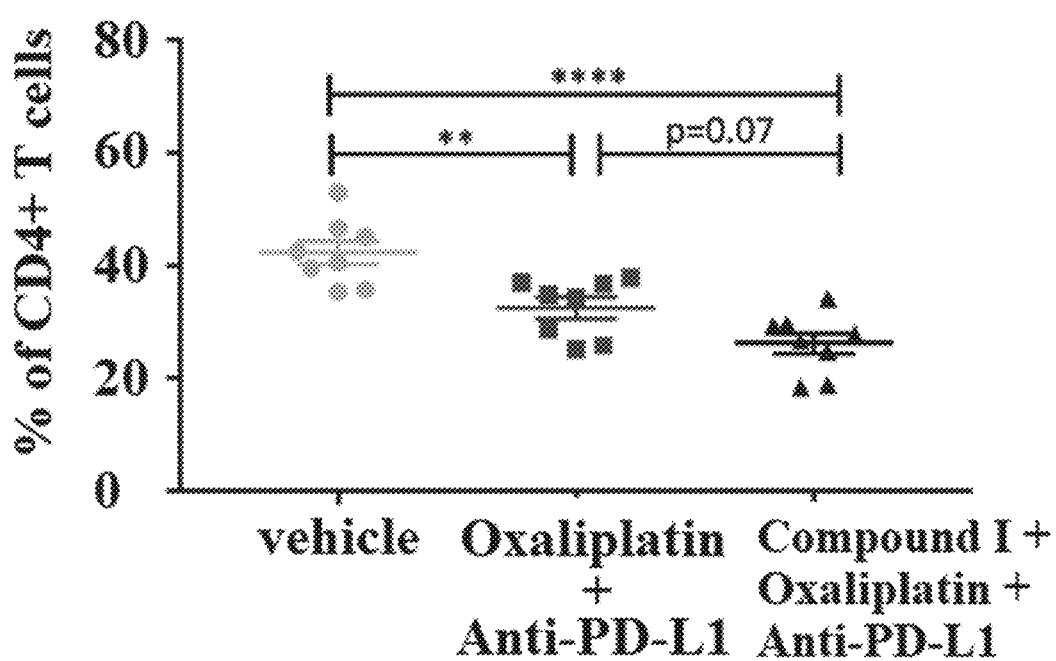
FIG. 10 depicts the percent of CD4+ T cells when MC38 tumor-bearing mice were treated with vehicle, oxaliplatin+anti-PPD-L1, or oxaliplatin+mouse anti-PD-L1+Compound I as analyzed by flow cytometric analysis. Tumors were harvested in immune cell infiltrates 5 days after final treatment for analysis as described in Example 5. Error bars represent SEM (standard error of the mean) and statistics were evaluated using one-way ANOVA (p<0.01 and **p<0.0001). The x-axis represents treatment conditions and the y-axis represents CD4+ T cells measured as a percentage.
Figure 11:
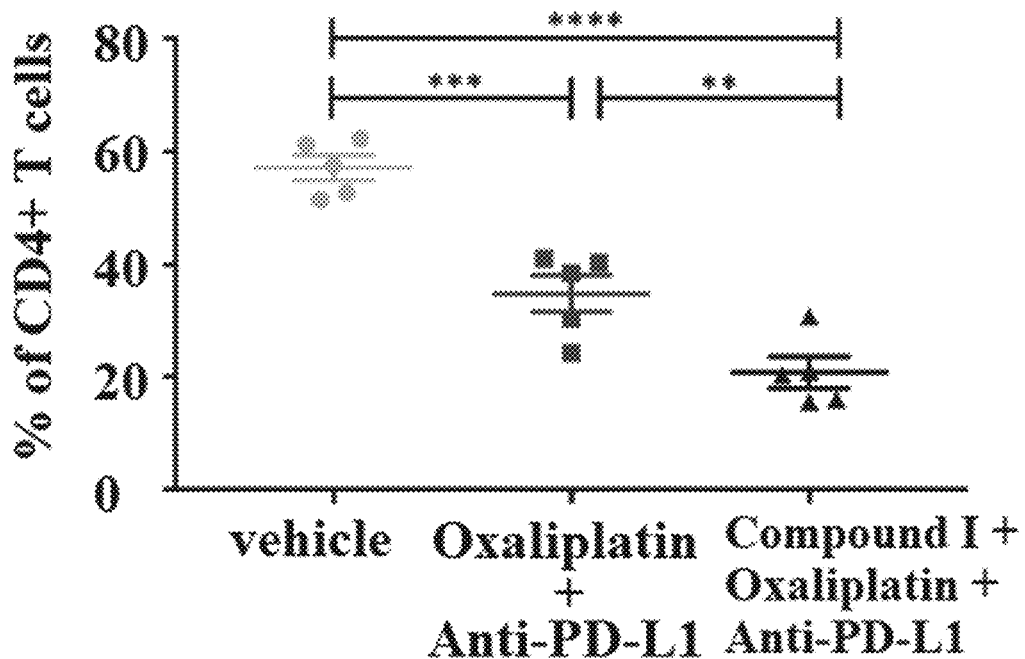
FIG. 11 depicts the percent of CD4+ T cells when MC38 tumor-bearing mice were treated with vehicle, oxaliplatin+mouse anti-PPD-L1, or oxaliplatin+mouse anti-PD-L1+Compound I as analyzed by flow cytometric analysis. Tumors were harvested in immune cell infiltrates 9 days after final treatment for analysis as described in Example 5. Error bars represent SEM (standard error of the mean) and statistics were evaluated using one-way ANOVA (p<0.01, *p<0.001, ****p<0.0001). The x-axis represents treatment conditions and the y-axis represents CD4+ T cells measured as a percentage.

Example 5. Adding Compound I to Oxaliplatin and Mouse Anti-PD-L1 Combination Therapy Further Decreases Intra-Tumor TREG Populations MC38 tumor-bearing C57BL/6 mice were treated with oxaliplatin (10 mg/kg, IP) and mouse anti-PD-L1 (clone 10F.9G2, 100 µg/mouse, IP)±Compound I (100 mg/kg, IP) for either four or eight days. Twenty-four hours post final dose, mice were euthanized and tumors were harvested in immune cell infiltrates after five days and nine days. Tumors were then processed and stained for CD45, CD3, CD4, CD25, and FOXP3. The CD25+FOXP3+ population was measured within the CD45+CD3+CD4+ population through flow cytometric analysis. The population of CD4+ cells harvested 5 day and 9 days after the final treatment are shown in FIG. 10 and FIG. 11, respectively. The population of intra-tumor $T_{reg}$ cells within the CD4+ T cell fraction was significantly decreased in mice treated with Compound I in combination with oxaliplatin and mouse anti-PD-L1 compared to vehicle and mice treated with oxaliplatin and mouse anti-PD-L1.

Figure 12:
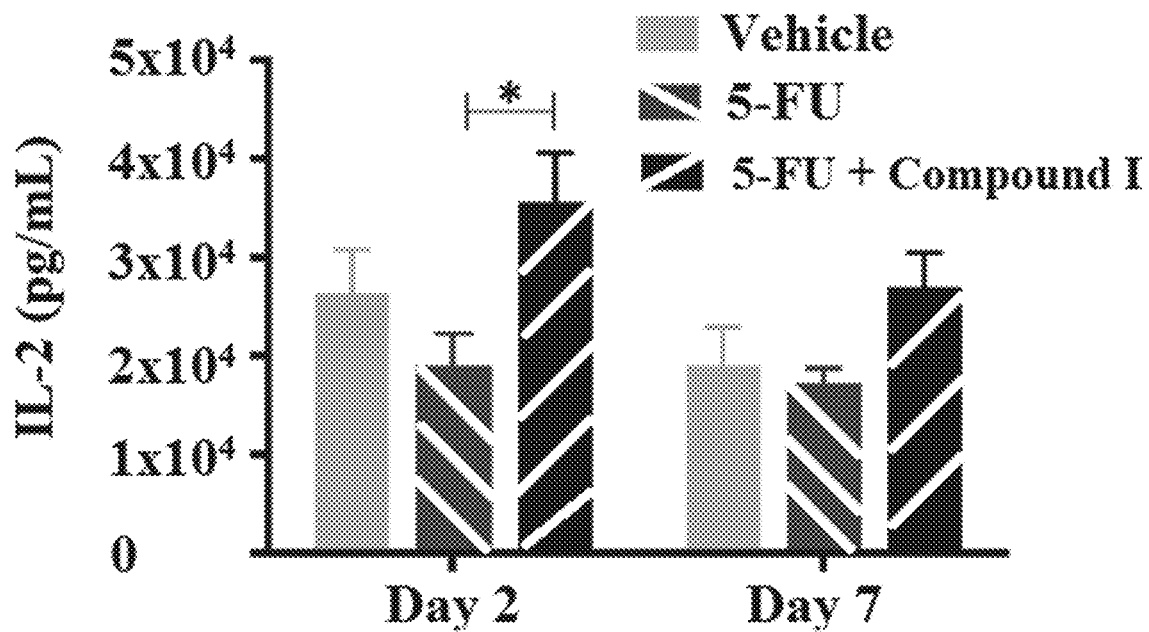
FIG. 12 depicts the concentration of IL-2 following ex-vivo splenocyte stimulation in C57BL/6 mice as described in Example 6. Mice were administered 3 daily IP doses of vehicle, 5-FU, or 5-FU+Compound I, and two and seven days after the final treatment, mice were euthanized and spleens were harvested. Error bars represent SEM (standard error of the mean) and statistics were evaluated using two-way ANOVA (*p<0.05). The x-axis represents treatment conditions and the y-axis represents IL-2 concentration measured in pg/mL.
Figure 13:
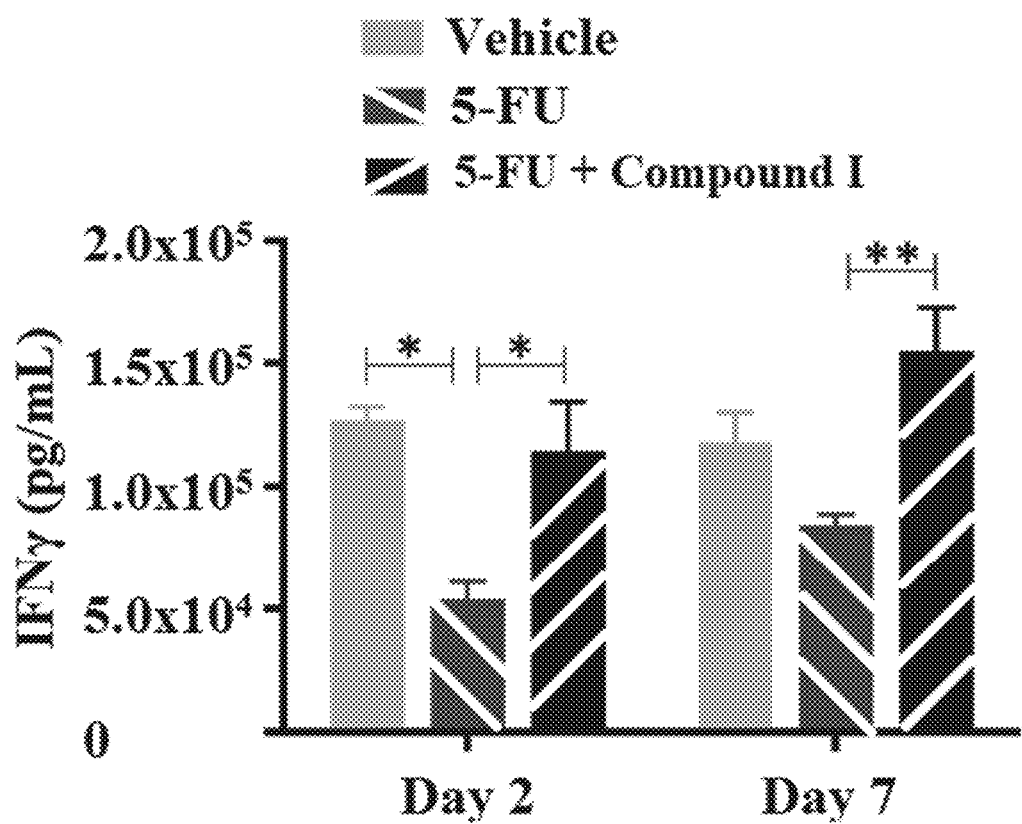
FIG. 13 depicts the concentration of IFNγ following ex-vivo splenocyte stimulation in C57BL/6 mice as described in Example 6. Mice were administered 3 daily IP doses of vehicle, 5-FU, or 5-FU+Compound I, and two and seven days after the final treatment, mice were euthanized and spleens were harvested. Error bars represent SEM (standard error of the mean) and statistics were evaluated using two-way ANOVA (*p<0.05 and **p<0.01). The x-axis represents treatment conditions and the y-axis represents IFNγ concentration measured in pg/mL.

Example 6. Compound I Preserves Lymphocyte Function when Added to 5-FU Treatment C57BL/6 mice were treated with 3 daily IP doses of 50 mg/kg 5-FU±100 mg/kg Compound I. Two and seven days after the final treatment, mice were euthanized and spleens were harvested. Splenocytes were stimulated ex vivo with anti-CD3/CD28 antibodies for 72 hours and interferon gamma (IFNγ) or interleukin-2 (IL-2) levels were measured via ELISA (R&D systems). After the ex-vivo splenocyte stimulation in C57BL/6 mice, Compound I enhanced IL-2 production (FIG. 12) and preserved IFNγ production (FIG. 13) after 5-FU treatment. A potential mechanism by which Compound I enhances anti-tumor activity includes the preservation of T lymphocyte function from chemotherapy.

Example 7. Compound I Enhances Anti-Tumor Efficacy when Added to a Combination Anti-PD-L1/Oxaliplatin Treatment CT26 bearing mice are treated with Compound I (IP, 100 mg/kg, weekly×3), anti-PD-L1 (IP, 5 mg/animal, biweekly to end), and/or oxaliplatin (IP, 10 mg/kg, weekly×3) and tumors were evaluated. The addition of Compound I to an anti-PD-L1/oxaliplatin regimen consistently enhanced anti-tumor efficacy in the CT26 model.

Figure 14:
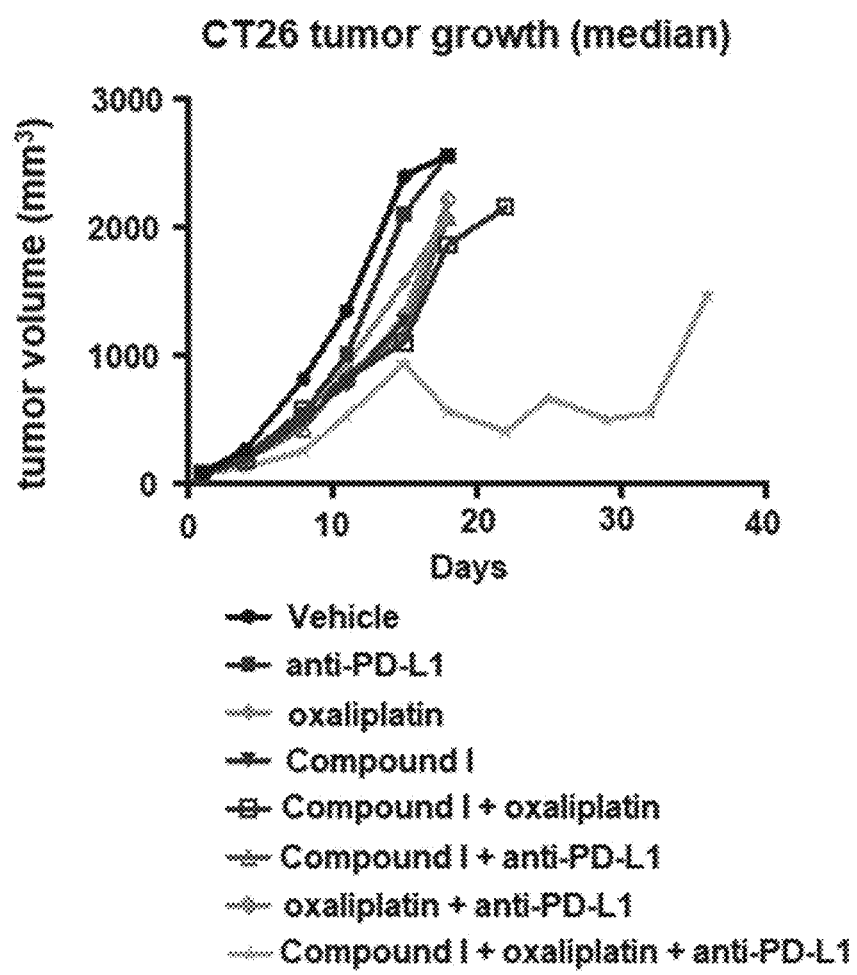
FIG. 14 and FIG. 15 depict the growth of a CT26 tumor in mice as described in Example 7. Mice were treated with Compound I (IP, 100 mg/kg, weekly×3), anti-PD-L1 (IP, 5 mg/animal, biweekly to end), and/or oxaliplatin (IP 10 mg/kg, weekly×3), and tumors were evaluated. The x-axis represents study length in days and the y-axis represents tumor volume in $mm^3$.
Figure 15:
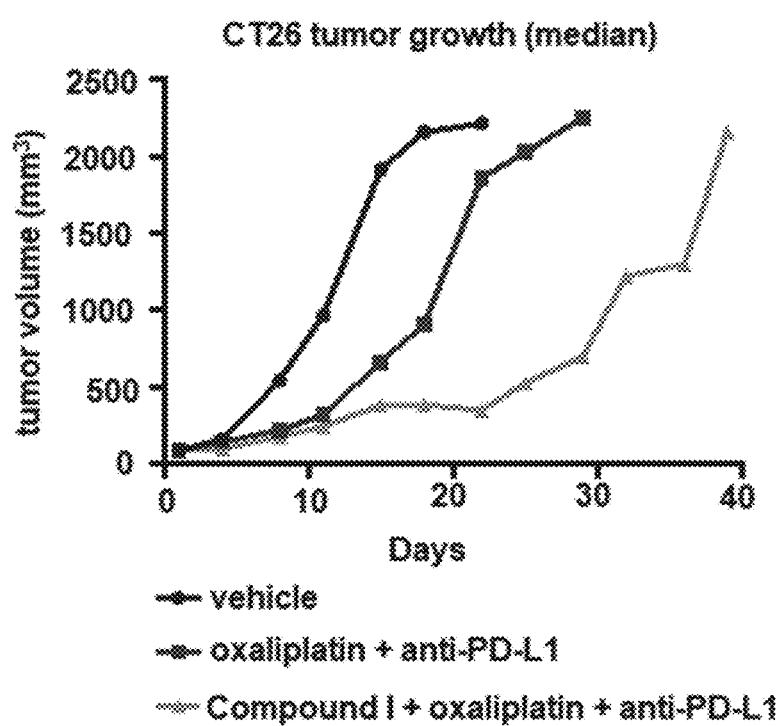

As shown in FIGS. 14 and 15, Compound I in combination with anti-PD-L 1 and oxaliplatin shows enhanced anti-tumor efficacy than any of the compounds alone or in paired combinations.

Figure 16:
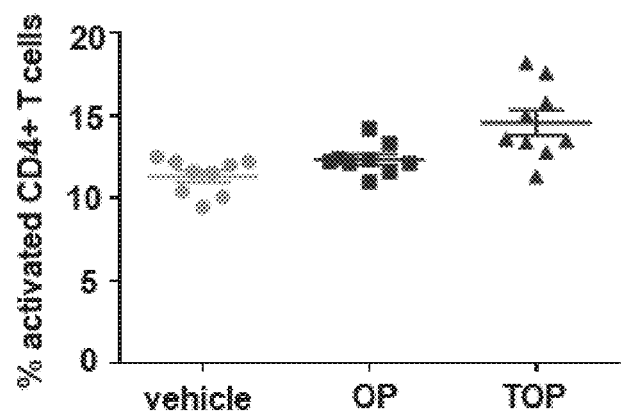
FIG. 16 depicts the activation of CD4+ T cells in MC38 tumor-bearing C5BL/6 mice as described in Example 8. The mice were treated with oxaliplatin (10 mg/kg, IP) and mouse anti-PD-L1 (clone 10F.9G2, 100 μg/mouse, IP) either (1) with Compound I (100 mg/kg, IP) (TOP) or (2) without Compound I (OP) for four days. Twenty-four hours after the last dose, the mice were euthanized and their spleens were harvested. Error bars represent SEM (standard error of the mean). The x-axis represents treatment conditions and the y-axis represents activated CD4+ T cells measured as a percentage.
Figure 17:
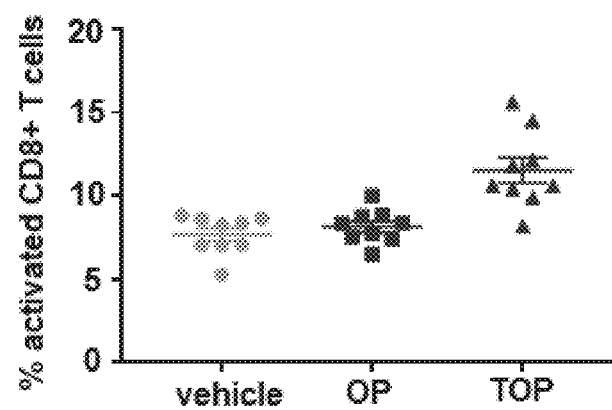
FIG. 17 depicts the activation of CD8+ T cells in MC38 tumor-bearing CSBL/6 mice as described in Example 8. The mice were treated with oxaliplatin (10 mg/kg, IP) and mouse anti-PD-L1 (clone 10F.9G2, 100 μg/mouse, IP) either (1) with Compound I (100 mg/kg, IP) (TOP) or (2) without Compound I (OP) for four days. Twenty-four hours after the last dose, the mice were euthanized and their spleens were harvested. Error bars represent SEM (standard error of the mean). The x-axis represents treatment conditions and the y-axis represents activated CD8+ T cells measured as a percentage.
Figure 18:
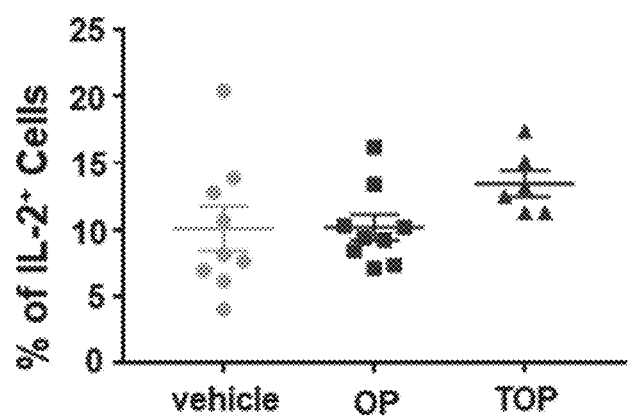
FIG. 18 depicts the percent proliferation of CD8+ T cells in the presence or absence of Tregs as described in Example 8. The mice were treated with oxaliplatin (10 mg/kg, IP) and mouse anti-PD-L1 (clone 10F.9G2, 100 μg/mouse, IP) either (1) with Compound I (100 mg/kg, IP) (TOP) or (2) without Compound I (OP) for four days. Twenty-four hours after the last dose, the mice were euthanized and their spleens were harvested. Splenocytes were stimulated ex vivo with anti-CD3/CD28 antibodies for 72 hours and then stained with IL-2 antibodies for flow cytometric analysis. Error bars represent SEM (standard error of the mean). The x-axis represents treatment conditions and the y-axis represents Il-2 expressing cells measured as a percentage.

Example 8. Adding Compound I to Oxaliplatin and Anti-PD-L1 Combination Therapy Enhanced T Cell Activation MC38 tumor bearing CSBL/6 mice were treated with oxaliplatin (10 mg/kg, IP) and mouse anti-PD-L1 (clone 10F.9G2, 100 µg/mouse, IP) with or without Compound I (100 mg/kg, IP) for four days. Twenty-four hours after the final dose, the mice were euthanized and spleens were harvested and processed to single-cell suspensions for T-cell analysis. Splenocytes were stained with anti-CD4, CD8, and CD69 antibodies for flow cytometric analysis. The percentage of activated CD4+ T cells was defined as the proportion of CD69+ cells within the CD8-CD4+ T cell fraction, while the percentage of activated CD8+ T cells was defined as the proportion of CD69+ cells within the CD8+CD4– T cell fraction, the results of which are shown in FIGS. 16 and 17. Additionally, splenocytes were also stimulated ex-vivo with anti-CD3/CD28 antibodies for 72 hours and were stained with ant-CD4, CD8, and IL-2 antibodies for flow cytometric analysis. The percentage of IL-2+ cells was defined as the proportion of IL-2+ cells within the CDK4+CD8– T cell fraction, the results of which are shown in FIG. 18.

Compared to oxaliplatin and anti-PD-L1 (OP) treated animals, Compound I, oxaliplatin, and anti-PD-L1(TOP) treated mice had proportions of activated CD4+ and CD*+ T cells and an enhanced ability of CD4+ T cells to produce the IL-2 cytokine upon ex-vivo activation.

Figure 19:
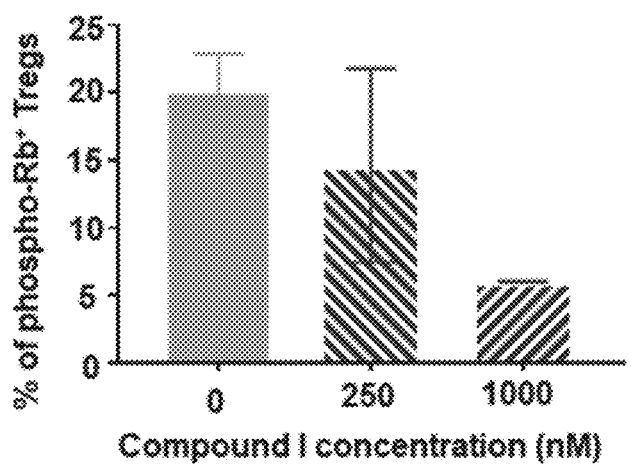
FIG. 19 depicts the ex vivo phosphorylation of Rb in Tregs isolated from C57BL/6 mice as described in Example 9. CD4+CD25+ Tregs were purified from the spleens using a two-step magnetic bead separation process-depletion of all non-CD4+ cells followed by positive selection of CD25+ cells. Purified Tregs were cultured ex vivo with anti-CD3/CD8 antibodies and IL-2 for 48 hours with either 0, 250, or 1000 nm of Compound I. The cultured Tregs were then stained with CD4, Foxp3, and phosphor-Rb antibodies for flow cytometric analysis. Error bars represent SEM (standard error of the mean). The x-axis represents nanomolar concentration of Compound I and the y-axis represents phospho-$Rb^+$ cells measured as a percentage.
Figure 20:
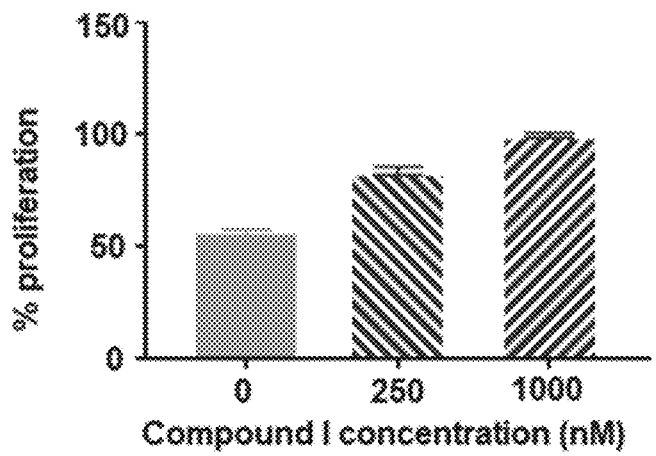
FIG. 20 represents the ex vivo proliferation of CD8+ T cells in the present of Tregs treated with Compound I as described in Example 9. The mice were treated with oxaliplatin (10 mg/kg, IP) and mouse anti-PD-L1 (clone 10F.9G2, 100 μg/mouse, IP) either (1) with Compound I (100 mg/kg, IP) (TOP) or (2) without Compound I (OP) for four days. Twenty-four hours after the last dose, the mice were euthanized and their spleens were harvested. Cells were stained with anti-CD4 and CD8 antibodies, and T cell proliferation was assessed by the dilution of the mean fluorescence intensity of CFSE in CD4-CD8+ T cells by flow cytometric analysis. Error bars represent SEM (standard error of the mean). The x-axis represents nanomolar concentration of Compound I and the y-axis represents the proliferation of CD8+ T cells measured as a percentage.

Example 9. Direct Inhibition of the CDK4/6-Rb Pathway in Regulatory T Cells (Tregs) Leads to Loss of Immuno-Suppressive Function and Enhanced CD8+ T Cell Proliferation CD4+CD25+ Tregs were purified from spleens of C57BL/6 mice using a two-step magnetic bead separation process-depletion of all non-CD4+ cells followed by positive selection of CD25+ cells. Purified Tregs were cultured ex-vivo with anti-CD3/CD8 antibodies and IL-2 for 48 hours with either 0, 250, or 1000 nM trilaciclib. As seen in Figure X, cultured Tregs were stained with CD4, Foxp3, and phospho-Rb antibodies for flow cytometric analysis. The percentage of phospho-Rb+ Tregs was defined as phospho-Rb+ cells in the CD4+Foxp3+ population. A dose-dependent down-regulation of phospho-Rb level was observed in Tregs after treatment with Compound I, indicative of inhibition of the CDK4/6-Rb pathway. CFSE-labeled splenocytes were stimulated ex-vivo with anti-CD3/CD28 antibodies for 72 hours in the presence or absence of Tregs treated with Compound I. Cells were stained with anti-CD4 and CD8 antibodies, and T cell proliferation was assessed by the dilution of the mean fluorescence intensity of CFSE in CD4–CD8+ T cells by flow cytometric analysis. Percent proliferation was calculated as (mean CFSE intensity of CD8+ T cells stimulated in the absence of Tregs)/(mean CFSE intensity of CD8+ T cells stimulated in the presence of Tregs)×100, the results of which are shown in FIG. 19 and FIG. 20.

A dose-dependent increase in proliferation was observed in CD8+ T cells in the presence of Tregs treated with Compound I, indicating that direct inhibition of the CDK4/6-Rb pathway can lead to loss of suppressive function in Tregs to inhibit T cell proliferation.

Figure 21:
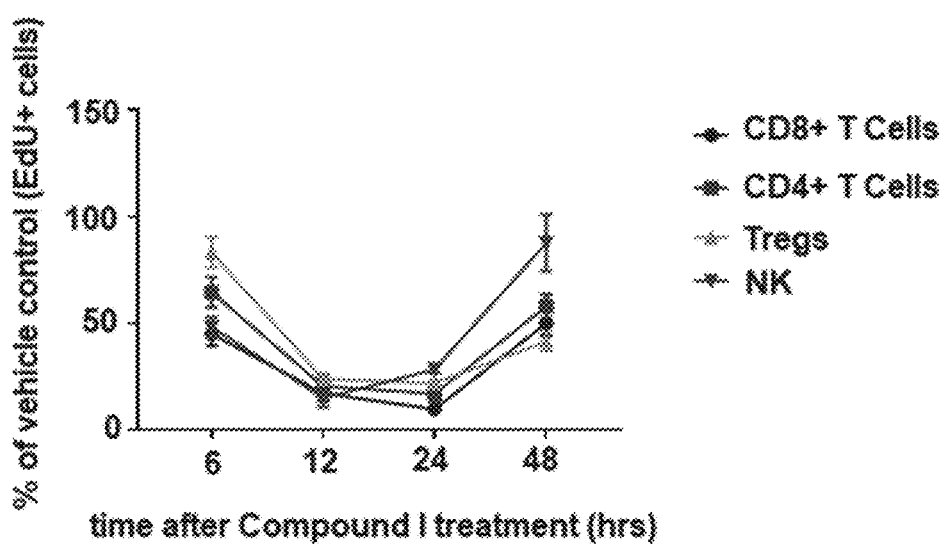
FIG. 21 and FIG. 22 depict the transient inhibition of proliferation of intra-tumor immune cells in MC38 tumor-bearing C57B1/6 mice as described in Example 10. The mice were treated with one dose of Compound I (100 mg/kg, IP) followed by EdU (200 μg/mouse, IP) incorporation 6 to 48 hours after treatment with Compound I. The mice were euthanized and the tumors harvested for analysis. Immune cells were subject to antibody labeling for the following immune cell populations: (1) CD8+ T cells; (2) CD4+ T Cells; (3) Tregs; (4) NK; (5) monocytic myeloid-derived suppressor cells (mMDSCs); (6) granulocytic myeloid-derived suppressor cells (gMDSCs); and (7) macrophages. EdU incorporation was detected by click chemistry followed by flow cytometric analysis. Error bars represent SEM (standard error of the mean). The x-axis represents treatment time in hours and the y-axis represents $EdU^+$ cells measured as a percentage.
Figure 22:
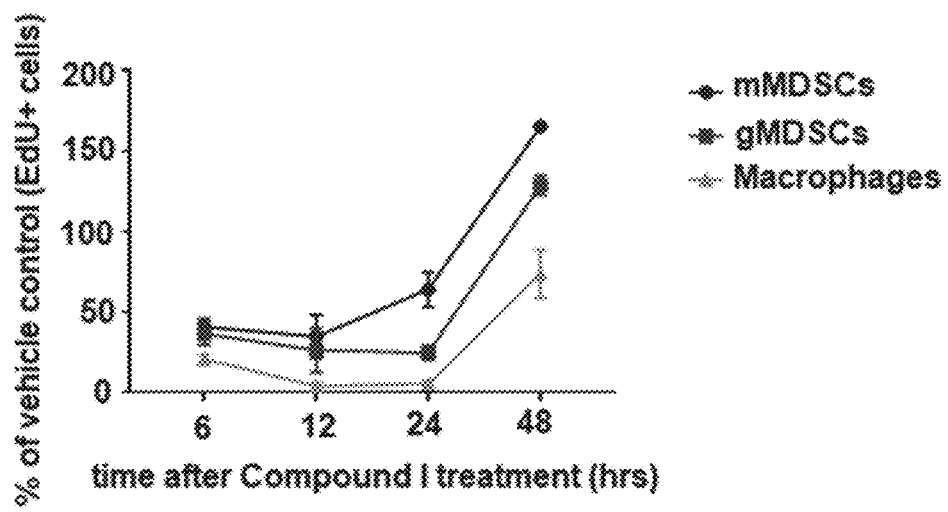

Example 10. Transient and Reversible Inhibition of Proliferation in Intra-Tumor Immune Cell Population after Treatment with Compound I MC38 tumor-bearing C57BL/6 mice were treated with one dose of Compound I (100 mg/kg, IP), followed by in vivo EdU (5-ethynyl-2'-deoxyuridine, 200 µg/mouse, IP) incorporation 6 to 48 hours after treatment with Compound I. Eighteen hours after EdU dosing, mice were euthanized and tumors were harvested for analysis. Tumors were processed to single-cell suspensions, followed by depletion of dead cells and enrichment of CD45+ immune cells prior to antibody labeling for various lymphoid and myeloid immune cell populations defined as follows: CD8+ T cells (CD4–CD8+), CD4+ T cells (CD4+CD8–Foxp3–), Tregs (CD4+CD8–Foxp3+), NK (CD3–NK1.1+), monocytic myeloid derived suppressor cells (mMDSCs, CD11b+Ly6C+Ly6G–), granulocytic myeloid derived suppressor cells (gMDSCs, CD11b+Ly6C+Ly6G+), and macrophages (CD11b+Ly6C–Ly6G–). After cell surface staining, cell samples were fixed and EdU incorporation was detected by click chemistry followed by flow cytometric analysis. Inhibition of proliferation is represented as the (% EdU+ in Compound I treated)/(% EdU+ in vehicle treated)×100 for each cell population at each time point. As can be seen in FIGS. 21 and 22, all lymphoid and myeloid immune cell populations analyzed were highly sensitive to CDK4/6 inhibition, leading to transient and reversible inhibition of cell proliferation. These results indicate that addition of Compound I to chemotherapy regimens has the potential to protect intra-tumor immune cells from chemotoxicity, leading to an enhanced anti-tumor response.

Figure 23:
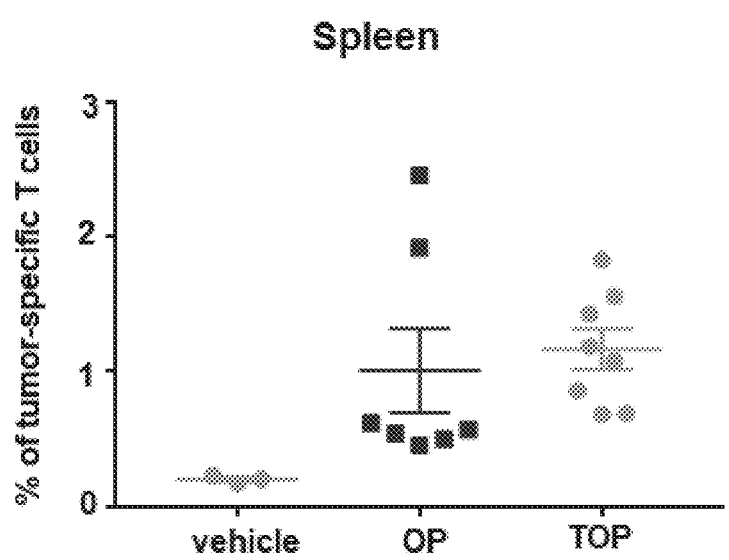
FIG. 23 and FIG. 24 depict the enhanced generation of tumor-specific T cells in MC38 tumor-bearing C57BL/6 mice as described in Example 11. The mice were treated with oxaliplatin (10 mg/kg, IP) and mouse anti-PD-L1 (clone 10F.9G2, 100 μg/mouse, IP) with (TOP) or without (OP) Compound I (100 mg/kg, IP) for 58 days following the IM schedule shown in FIG. 3. The mice were euthanized and their spleen (FIG. 23) and peripheral blood (FIG. 24) collected for analysis. The error bars represent SEM (standard error of the mean). The x-axis represents treatment conditions and the y-axis represents tumor-specific T cells measured as a percentage.
Figure 24:
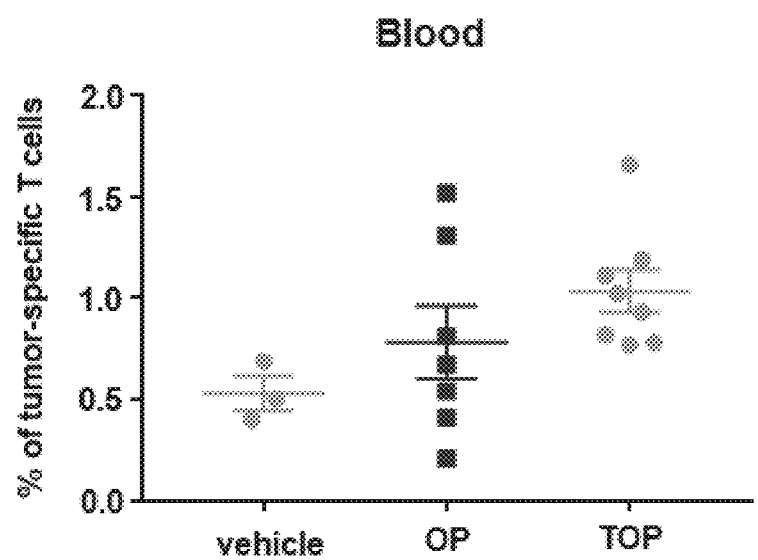

Example 11. Adding Compound I (T) to Oxaliplatin (O) and Anti-PD-L1 (P) Combination Therapy Enhances the Generation of Tumor-Specific Memory T Cells MC38 tumor-bearing C57BL/6 mice were treated with oxaliplatin (10 mg/kg, IP) and mouse anti-PD-L1 (clone 10F.9G2, 100 μg/mouse, IP) with or without Compound I (100 mg/kg, IP) for 58 days following the IM schedule as shown in FIG. 3. Spleen and peripheral blood were collected from oxaliplatin and anti-PD-L1 (OP) treated mice and Compound I, oxaliplatin, and anti-PD-L1 (TOP) treated mice on day 58 for analysis. Vehicle treated mice were euthanized for analysis on day 28 when reaching tumor-growth endpoint (tumor volume >1000 mm³). Splenocytes and red blood cell-lysed peripheral blood samples were stained with CD4, CD8, and MC38-specific dextramer (H-2 Db/ASMTNMELM). The percentage of tumor-specific T cells were identified as the proportion of dextramer+ cells within the CD4-CD8+ T cell fraction. As shown in FIGS. 23 and 24, the majority of TOP treated mice had higher proportion of tumor-specific T cells in spleen and blood compared to the OP treatment group, indicating that preservation of intra-tumor T cells by Compound I during chemotherapy/checkpoint inhibitor treatment can lead to the generation of higher number of tumor-specific memory T cells.

Figure 25:
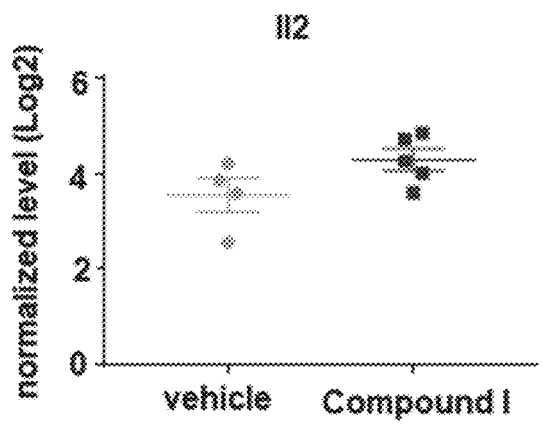
FIG. 25, FIG. 26, and FIG. 27 depict the upregulation of genes that positively regulate interferon-gamma expression in MC38 tumor-bearing C57BL/6 mice as described in Example 12. The mice were treated with two weekly doses of Compound I (100 mg/kg, IP). One day after the last dose, the mice were euthanized and the tumors harvested for analysis. Gene expression analysis for Il2 (FIG. 25), Il18 (FIG. 26), and Lta (FIG. 27) was performed on whole tumors using the PanCancer Immune Profiling Panel. Error bars represent SEM (standard error of the mean). The x-axis represents treatment conditions and the y-axis represents the normalized and Log 2 transformed expression values for the selected genes.
Figure 26:
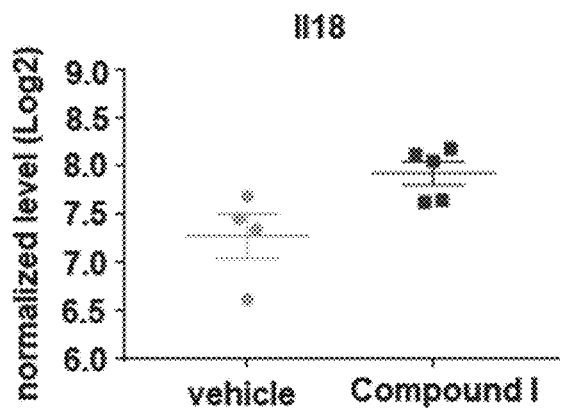
Figure 27:
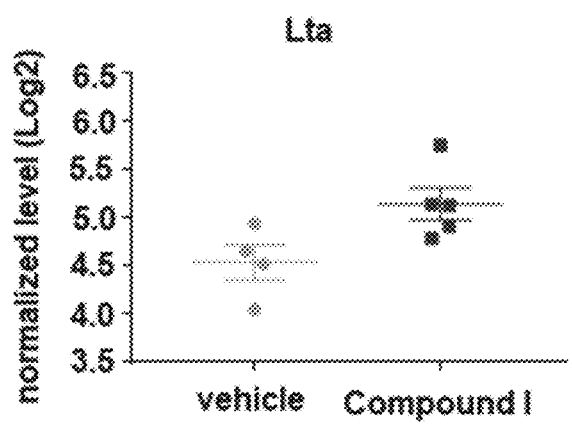
Figure 28:
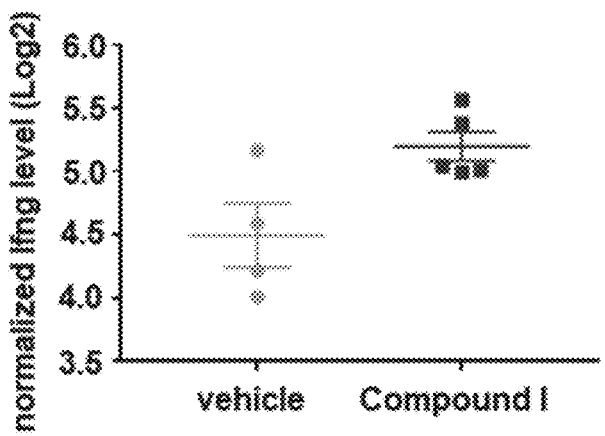
FIG. 28, FIG. 29, FIG. 30, and FIG. 31 depict the upregulation of interferon-gamma gene expression in MC38 tumor-bearing C57BL/6 mice as described in Example 13. The mice were treated with: Compound I (100 mg/kg, IP) (FIG. 28); oxaliplatin (100 mg/kg, IP) with (TO) or without (O) Compound I (100 mg/kg, IP) (FIG. 29); anti-PD-L1 (clone 10F.9G2, 100 μg/mouse, IP) with (TP) or without (P) Compound I (100 mg/kg, IP) (FIG. 30); and both oxaliplatin (100 mg/kg, IP) and anti-PD-L1 (clone 10F.9G2, 100 μg/mouse, IP) with (TOP) or without (OP) Compound I (100 mg/kg, IP) (FIG. 31) for eight days. Twenty-four hours after the final dose, the mice were euthanized and tumors were harvested for analysis. Gene expression analysis was performed on whole tumors using the PanCancer Immune Profilinf Panel. Error bars represent SEM (standard error of the mean). The x-axis represents treatment conditions and the y-axis represents the normalized and Log 2 transformed expression values for Ifng.
Figure 29:
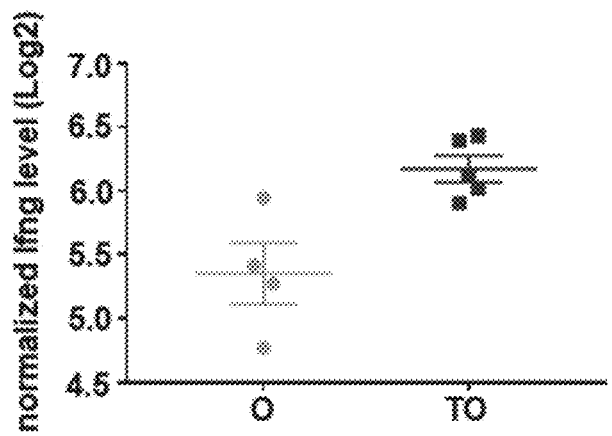
Figure 30:
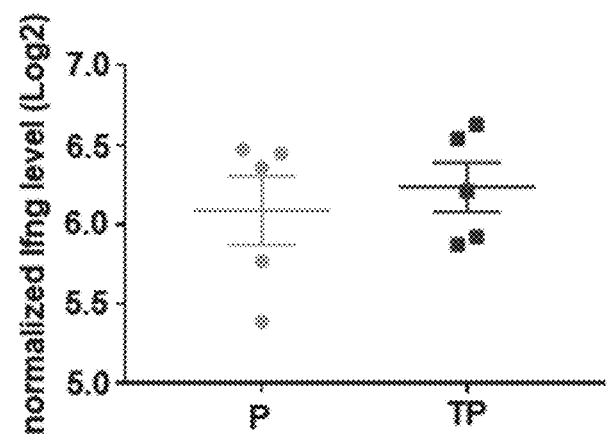
Figure 31:
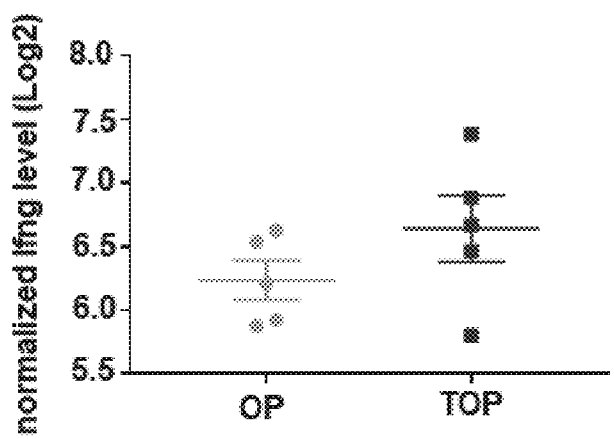
Figure 32:
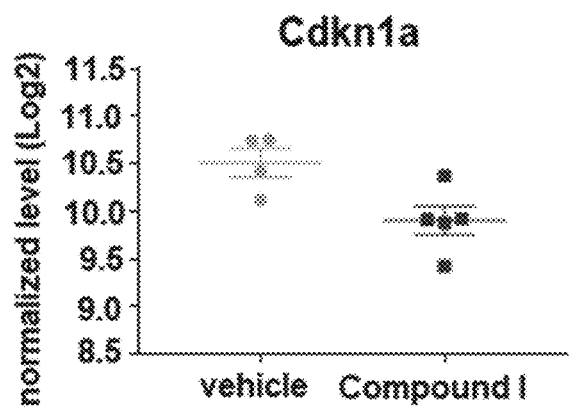
FIG. 32, FIG. 33, FIG. 34, FIG. 35, FIG. 36, and FIG. 37 depict the down-regulation of genes related to reactive oxygen species metabolism in MC38 tumor-bearing C57BL/6 mice as described in Example 14. The mice were treated with two weekly doses of Compound I (100 mg/kg, IP). One day after the last dose, the mice were euthanized and the tumors harvested for analysis. Gene expression analysis for Cdku1a (FIG. 32), Cxcl1 (FIG. 33), Il6 (FIG. 34), Il10 (FIG. 35), Il19 (FIG. 36), and Ptgs2 (FIG. 37) was performed on whole tumors using the PanCancer Immune Profiling Panel. Error bars represent SEM (standard error of the mean). The x-axis represents treatment conditions and the y-axis represents the normalized and Log 2 transformed expression values for the selected genes.
Figure 33:
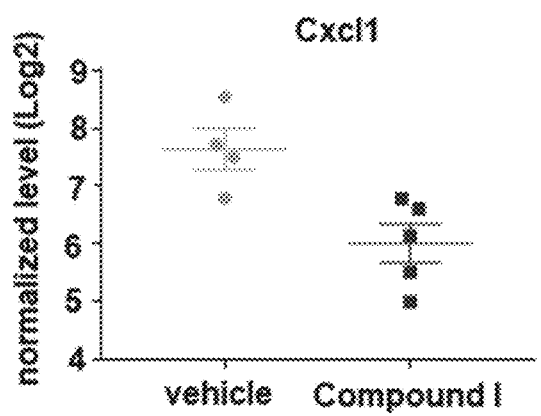
Figure 34:
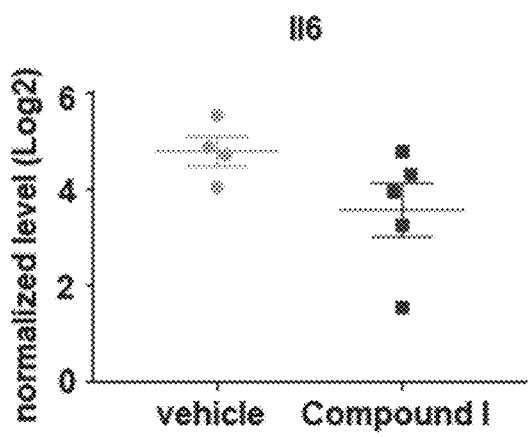
Figure 35:
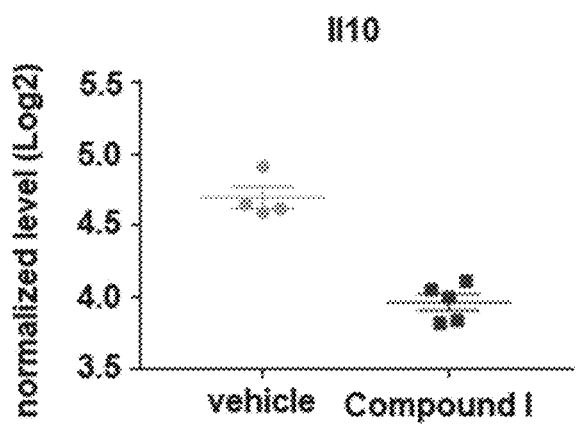
Figure 36:
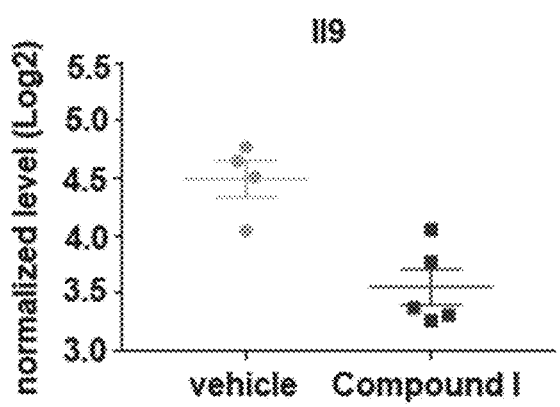
Figure 37:
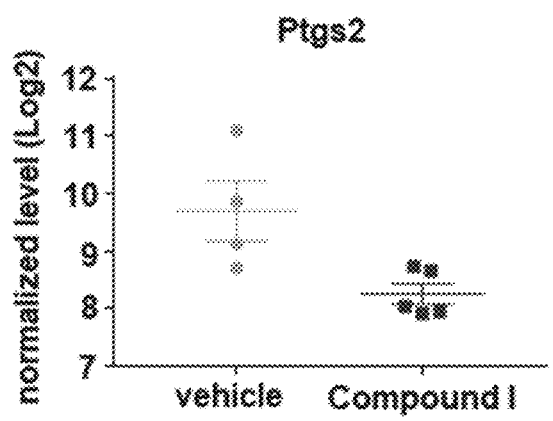

Example 12. Pulsatile Dosing of Compound I Leads to Upregulation of Genes that Positively Regulate Interferon-Gamma Expression, a Pro-Inflammatory Cytokine and a Critical Component in a T Cell Anti-Tumor Response MC38 tumor-bearing C57BL/6 mice were treated with two weekly doses of Compound I (100 mg/kg, IP). One day after the last dose, mice were euthanized and tumors were harvested for analysis. Gene expression analysis was performed on whole tumors using the PanCancer Immune Profiling Panel. Normalized and Log 2 transformed expression values were used for identification of differentially expressed genes, defined using a p-value cutoff of <0.05 and absolute fold change >1.3. Up-regulated genes were enriched for GO terms such as "positive regulation of interferon-gamma production" and "positive regulation of activated T cell proliferation", which include genes 112, 1118, and Lta as shown in FIGS. 25, 26, and 27. These results indicate that short exposure of Compound I can result in gene expression changes that promote a pro-inflammatory tumor microenvironment favorable of response to immune checkpoint blockade.

Example 13. Pulsatile Dosing of Compound I Leads to Upregulation of Interferon-Gamma Gene Expression in Tumor when Added to Oxaliplatin or Oxaliplatin/Anti-PD-L1 Combinations MC38 tumor-bearing C57BL/6 mice were treated with Compound I (100 mg/kg, IP), oxaliplatin (10 mg/kg, IP)±Compound I (100 mg/kg, IP), anti-PD-L1 (clone 10F.9G2, 100 μg/mouse, IP)±Compound I (100 mg/kg, IP), oxaliplatin (10 mg/kg, IP) and anti-PD-L1 (clone 10F.9G2, 100 μg/mouse, IP)±Compound I (100 mg/kg, IP) for eight days. Twenty-four hours after the final dose, mice were euthanized and tumors were harvested for analysis. Gene expression analysis was performed on whole tumors using the PanCancer Immune Profiling Panel. The normalized and Log 2 transformed expression level of interferon-gamma (Ifng) is plotted for each pair of treatment groups with or without Compound I. T=Compound I, O=oxaliplatin, P=anti-PD-L1. As shown in FIGS. 28 to 31, these results indicate that short exposure of Compound I can result in gene expression changes that promote a pro-inflammatory tumor microenvironment favorable of response to immune checkpoint blockade.

Example 14. Pulsatile Dosing of Compound I Leads to Down-Regulation of Genes Related to Reactive Oxygen Species Metabolism, an Important Pathway that Promotes Immuno-Suppression by Myeloid-Derived Suppressor Cells MC38 tumor-bearing C57BL/6 mice were treated with two weekly doses of Compound I (100 mg/kg, IP). One day after the last dose, mice were euthanized and tumors were harvested for analysis. Gene expression analysis was performed on whole tumors using the PanCancer Immune Profiling Panel. Normalized and Log 2 transformed expression values were used for identification of differentially expressed genes, defined using a p-value cutoff of <0.05 and absolute fold change >1.3. Down-regulated genes were enriched for the GO term "positive regulation of reactive oxygen species metabolism", including Cdkn1a, Cxcl1, Il6, Il0, Il19, Ptgs2. As shown in FIGS. 32 to 37, these results indicate that short exposure of Compound I can result in gene expression changes leading to a tumor microenvironment that is less immuno-suppressive.

Figure 39:
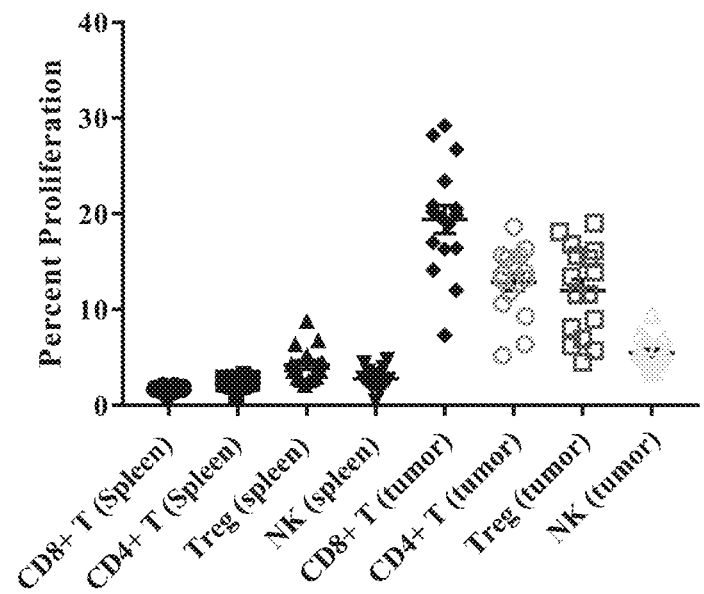
FIG. 39 and FIG. 40 depict intra-tumor immune cell proliferation in MC38 tumor-bearing C57BL/6 mice treated with Compound I as described in Example 15. Error bars represent SEM (standard error of the mean). The x-axis represents intra-tumor immune cell type and the y-axis represents proliferation measured as a percentage.
Figure 40:
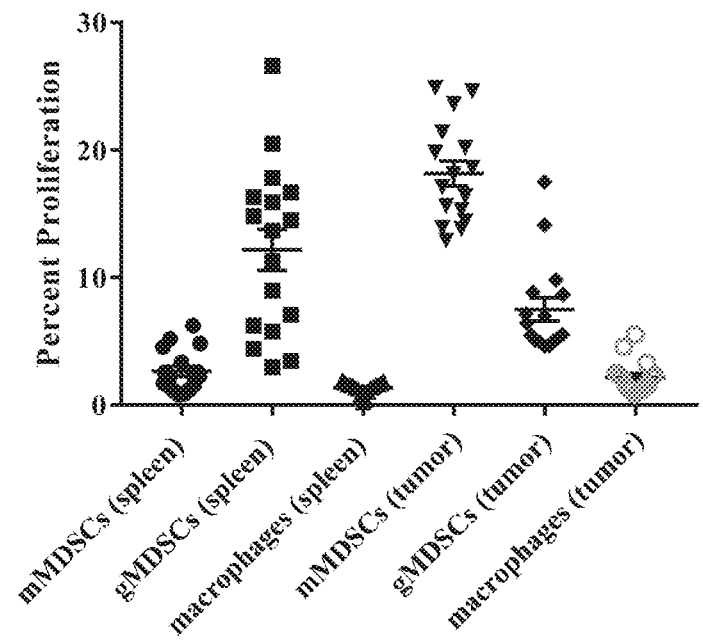
Figure 41:
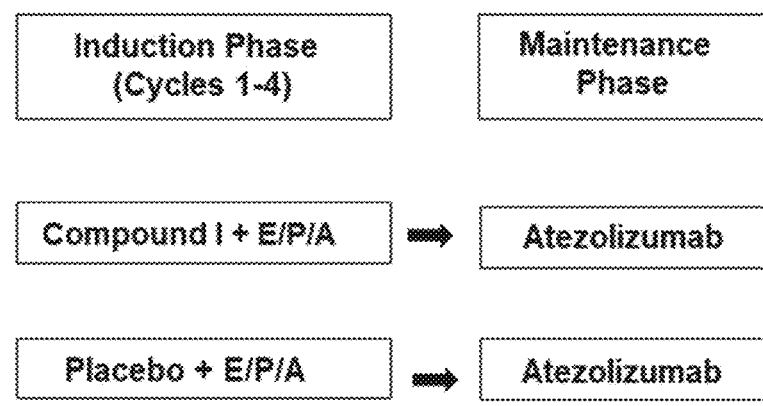
FIG. 41 depicts a flow chart outlining the organizational structure of the clinical study outlined in Example 17. The clinical trial is organized into two phases: an induction phase that may be repeated up to four times, and a maintenance phase. Compound I or placebo is combined with etoposide/carboplatin/atezolizumab (E/P/A) therapy during the induction phase. Only atezolizumab is dosed during the maintenance phase.

Example 15. Intra-Tumor Immune Cell Populations have High Levels of Proliferation Compared to their Counterparts in the Spleen, Indicating that Addition of Compound I to Chemotherapy Regimens has the Potential to Protect Intra-Tumor Immune Cells from Chemotherapy, Leading to an Enhanced Anti-Tumor Response MC38 tumor-bearing C57BL/6 mice were administered EdU (5-ethynyl-2'-deoxyuridine, 200 μg/mouse, IP). Eighteen hours after EdU dosing, mice were euthanized and tumors and spleens were harvested for analysis. Tumors and spleens were processed to single-cell suspensions, followed by depletion of dead cells and enrichment of CD45+ immune cells prior to antibody labeling for various lymphoid and myeloid immune cell populations defined as follows: CD8+ T cells (CD4−CD8+), CD4+ T cells (CD4+CD8−Foxp3−), Tregs (CD4+CD8−Foxp3+), NK (CD3−NK1.1+), monocytic myeloid derived suppressor cells (mMDSCs, CD11b+Ly6C+Ly6G−), granulocytic myeloid derived suppressor cells (gMDSCs, CD11b+Ly6C+Ly6G+), and macrophages (CD11b+Ly6C−Ly6G−). After cell surface staining, cell samples were fixed and EdU incorporation was detected by Click chemistry followed by flow cytometric analysis. The percentage of proliferation was determined as the % EdU+ within each defined cell population. As shown in FIGS. 39 and 40, all lymphocyte subsets and MDSCs in the tumors exhibit high levels of proliferation, indicating that addition of Compound I to chemotherapy regimens has the potential to protect intra-tumor immune cells from chemotoxicity, leading to an enhanced anti-tumor response.

Figure 38:
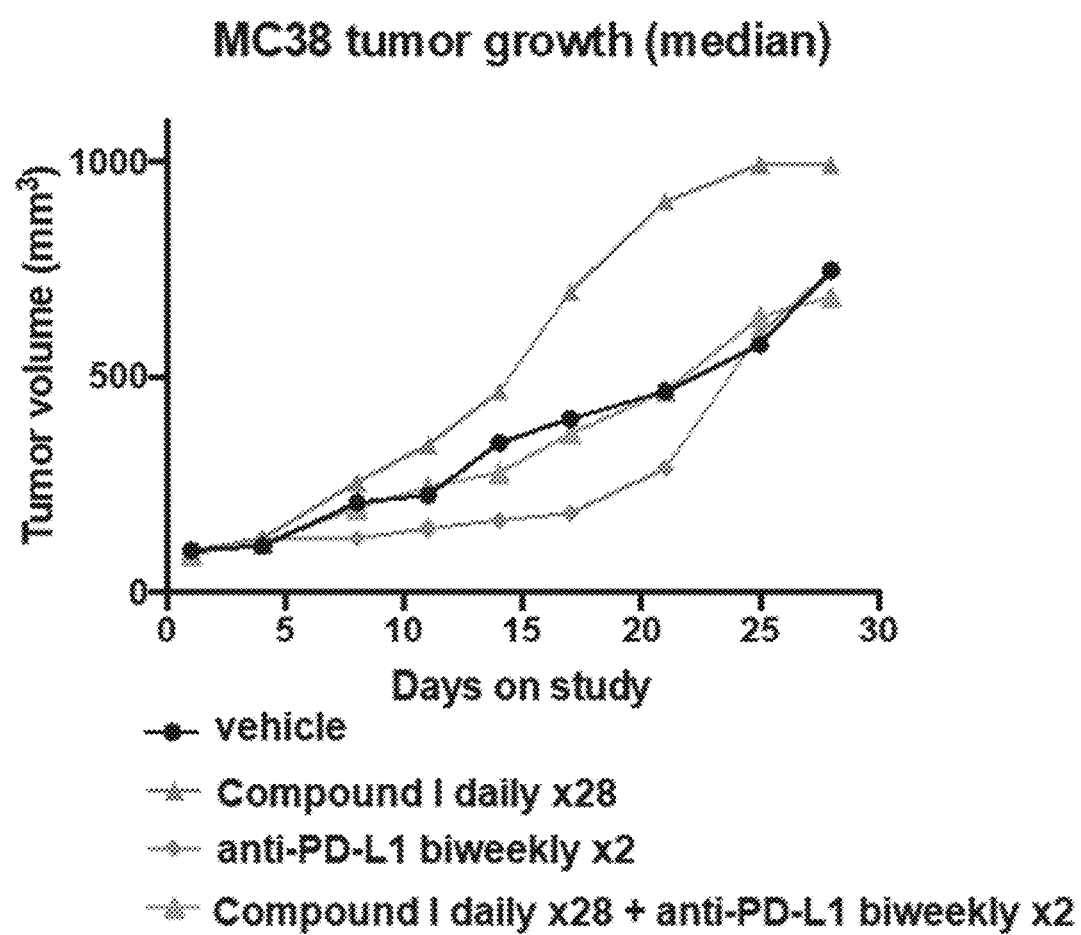
FIG. 38 depicts the growth of a MC38 tumor in mice continuous treatment with Compound I (daily×28) either with or without anti-PD-L1 (biweekly ×2). The x-axis represents study length in days and the y-axis represents tumor volume in mm³.

Example 16. Continuous Dosing of Compound I in Combination with Checkpoint Inhibitor Did not Result in Enhancement of Anti-Tumor Response MC38 tumor-bearing mice were treated with Compound I (daily×28 days, IP, 100 mg/kg) with or without anti-PD-L1 (biweekly ×2 weeks, IP, 100 ug/animal) and tumor volume was evaluated. As can be seen in FIG. 38, adding Compound I to an anti-PD-L1 regimen suppressed the minimal effect observed in the anti-PD-L1 only cohort. These data indicate the addition of continuous treatment of Compound I to anti-PD-L1 does not enhance the anti-tumor effect and, in fact, causes some attenuation.

Example 17. Clinical Study Protocol for Treatment of Patients with Small Cell Lung Carcinoma with Compound I in Combination with Atezolizumab, Etoposide, and Carboplatin A clinical trial has been designed for the treatment of small cell lung carcinoma using a combination of Compound I, atezolizumab, etoposide, and carboplatin comprising a 21-day induction phase and a 21-day maintenance phase. Up to four induction phase cycles will be completed if the patient meets the following criteria before each induction phase cycle: ANC>$1.5×10^9$/L; platelet count >$100×10^9$/L; and non-hematological drug-related toxicities (except alopecia) must be <grade 1 or returned to baseline. A maintenance phase cycle is begun directly after the latest induction phase if the patient does not meet the above criteria. Upon completion of up to four induction cycles, a 21-day maintenance phase cycle is then started. One or more additional maintenance phase cycles can be administered as tolerated up until completion of the study.

In the induction phase, patients receive Compound I (240 mg/m² diluted in 250 mL D5W or sodium chloride solution 0.9%) or placebo (250 mL of D5W or sodium chloride solution 0.9%) administered IV once daily on days 1 to 3 of each etoposide/carboplatin/atezolizumab (E/P/A) therapy cycle (up to 4 cycles in total). In the maintenance phase, patients receive atezolizumab every 21 days. Patients receive E/P/A therapy in 21-day cycles during the induction phase. The carboplatin dose is calculated using the Calvert formula [total carboplatin dose (mg)=(target AUC)×(GFR+25)] with a target AUC=5 (maximum 750 mg) IV over 30 minutes on day 1, and 100 mg/m² etoposide is administered IV over 60 minutes daily on days 1, 2, and 3 of each 21-day cycle. Atezolizumab (1200 mg) in 250 mL sodium chloride solution 0.9% is administered as an IV infusion on day 1 of each 21-day cycle in both the induction and maintenance phases. Atezolizumab is infused over 60 minutes for the first administration and, if tolerated, all subsequent infusions are delivered over 30 minutes. Atezolizumab is administered following the completion of administration of Compound I or placebo, etoposide, and carboplatin.

The interval between doses of Compound I or placebo on successive days is no greater than 28 hours. The interval between the dose of Compound I or placebo on a given day (etoposide or carboplatin) is no greater than 4 hours. Compound I or placebo is only administered with etoposide/carboplatin (E/P) therapy. If administration of E/P therapy is held or discontinued, Compound I or placebo is also held or discontinued. Chemotherapy is not administered until after completion of the Compound I or placebo infusion. In both parts of the study, study drug administration is continued until disease progression per RECIST v.1.1, unacceptable toxicity, withdrawal of consent, or discontinuation by investigator. Following disease progression per RECIST v1.1, if the patient appears to be deriving clinical benefit, the investigator believes it is in the best interest of the patient, and the patient has provided re-consent, study drug administration may be continued until loss of clinical benefit.

This specification has been described with reference to embodiments of the invention. The invention has been described with reference to assorted embodiments, which are illustrated by the accompanying Examples. The invention can, however, be embodied in different forms and should not be construed as limited to the embodiments set forth herein. Given the teaching herein, one of ordinary skill in the art will be able to modify the invention for a desired purpose and such variations are considered within the scope of the invention.

What is claimed is:

1. A method of treating a human having cancer comprising administering to the human a therapeutic regimen comprising a) an induction phase and b) a maintenance phase,
   a) the induction phase comprising:
      i) administering to the human an effective amount of a selective Cyclin Dependent Kinase 4/6 (CDK4/6) inhibitor of structure:

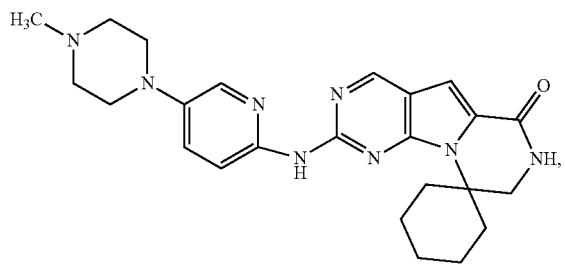

or a pharmaceutically acceptable salt thereof,
      ii) administering to the human an effective amount of a chemotherapeutic agent, and
      iii) administering to the human an effective amount of an immune checkpoint inhibitor,
   wherein, during the induction phase, the CDK4/6 inhibitor is only administered 24 hours or less prior to the administration of the chemotherapeutic agent, and
   wherein the chemotherapeutic agent is cytotoxic to immune effector cells;
   b) the maintenance phase comprising:
      i) administering to the human at least one dose of an effective amount of the immune checkpoint inhibitor, and
   wherein the maintenance phase is administered following the cessation of the induction phase.

2. The method of claim 1 wherein the immune checkpoint inhibitor is selected from the group consisting of a Programmed Cell Death-1 (PD-1) inhibitor, a Programmed Cell Death-Ligand 1 (PD-L1) inhibitor, and a cytotoxic T-lymphocyte-associated protein 4 (CTLA-4) inhibitor.

3. The method of claim 2, wherein the immune checkpoint inhibitor is a PD-L1 inhibitor.

4. The method of claim 3, wherein the PD-L1 inhibitor is selected from the group consisting of atezolizumab, avelumab, and durvalumab.

5. The method of claim 2, wherein the immune checkpoint inhibitor is a PD-1 inhibitor.

6. The method of claim 5, wherein the PD-1 inhibitor is selected from the group consisting of nivolumab, pidilizumab, and pembrolizumab.

7. The method of claim 2, wherein the immune checkpoint inhibitor is a CTLA-4 inhibitor.

8. The method of claim 7, wherein the CTLA-4 inhibitor is selected from the group consisting of ipilimumab and tremelimumab.

9. The method of claim 1, wherein the chemotherapeutic agent is selected from the group consisting of a protein synthesis inhibitor, a DNA-damaging chemotherapeutic, an akylating agent, a topoisomerase inhibitor, an RNA synthesis inhibitor, a DNA complex binder, a thiolate alkylating agent, a guanine alkylating agent, a tubulin binder, a DNA polymerase inhibitor, an anticancer enzyme, a RAC1 inhibitor, a thymidylate synthase inhibitor, an oxazophosphorine compound, an integrin inhibitor, an antifolate, a folate antimetabolite, and a combination thereof.

10. The method of claim 1, wherein the chemotherapeutic agent is selected from the group consisting of carboplatin, cisplatin, oxaliplatin, 5-fluorouracil, floxuridine, capecitabine, gemcitabine, mytomycin, cyclophosphamide, decarbazine, abraxane, ifosfamide, topotecan, irinotecan, docetaxel, temozolomide, paclitaxel, etoposide, pemetrexed, and a combination thereof.

11. The method of claim 1, wherein, during the induction phase, the CDK4/6 inhibitor is only administered about 30 minutes or less prior to the administration of the chemotherapeutic agent.

12. The method of claim 1, wherein the immune checkpoint inhibitor is administered to the subject every three weeks during the induction phase and maintenance phase.

13. The method of claim 1, wherein the cancer is selected from the group consisting of small cell lung cancer, non-small cell lung cancer, triple negative breast cancer, colorectal cancer, ovarian cancer, pancreatic cancer, bladder cancer, gastroesophageal cancer, cholangiocarcinoma, cervical cancer, and soft tissue sarcoma.

14. A method of treating a human having small cell lung cancer comprising administering to the human a therapeutic regimen comprising a) an induction phase comprising a 21-day cycle and b) a maintenance phase comprising a 21-day cycle,
a) the induction phase comprising:
i) administering to the human an effective amount of a selective CDK4/6 inhibitor of structure:

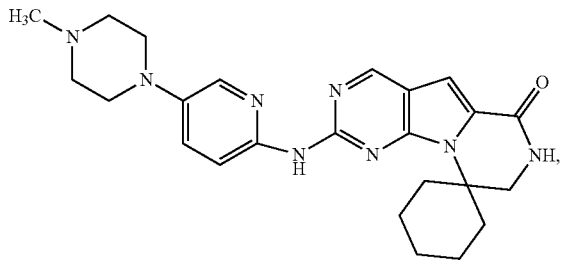 [SMILES: CN1CCN(c2ccc(Nc3ncc4cc5n(c4n3)C3(CCCCC3)CNC5=O)nc2)CC1]

or a pharmaceutically acceptable salt thereof, on day 1, day 2, and day 3 of the 21-day cycle,
ii) administering to the human an effective amount of carboplatin on day 1 of the 21-day cycle,
iii) administering to the human an effective amount of etoposide on day 1, day 2, and day 3 of the 21-day cycle, and
iv) administering to the human an effective amount of atezolizumab on day 1 of the 21-day cycle;
wherein, during the induction phase, the CDK4/6 inhibitor is only administered 24 hours or less prior to the administration of carboplatin and/or etoposide;
b) the maintenance phase comprising:
i) administering to the human an effective amount of atezolizumab on day 1 of the 21-day cycle,
wherein the maintenance phase is administered following the cessation of the induction phase.

15. The method of claim 14, wherein, during the induction phase, the CDK4/6 inhibitor is only administered about 4 hours or less prior to administration of the carboplatin and/or etoposide.

16. The method of claim 14, wherein, during the induction phase, the CDK4/6 inhibitor is only administered about 30 minutes or less prior to the administration of the carboplatin and/or etoposide.

17. The method of claim 14, wherein the CDK4/6 inhibitor is administered intravenously at a dose of between about 220 and 260 mg/m$^2$.

18. The method of claim 17, wherein the CDK4/6 inhibitor is administered intravenously at a dose of about 240 mg/m$^2$.

19. The method of claim 14, wherein the carboplatin is administered intravenously at a dose that provides an AUC of about 5.

20. The method of claim 14, wherein the etoposide is administered intravenously at a dose of about 100 mg/m$^2$.

21. The method of claim 14, wherein the atezolizumab is administered in a dose of about 1200 mg.

22. The method of claim 14, wherein the induction phase is repeated at least 2 times.

23. The method of claim 14, wherein the induction phase is repeated at least 3 times.

24. The method of claim 14, wherein the induction phase is repeated at least 4 times.

25. The method of claim 14, wherein the maintenance phase is repeated at least 2 times.

26. The method of claim 14, wherein the maintenance phase is repeated at least 3 times.

27. The method of claim 14, wherein the maintenance phase is repeated at least 4 times.

28. The method of claim 1, wherein the maintenance phase further comprises administering to the subject an effective amount of the CDK 4/6 inhibitor.

29. The method of claim 13, wherein the cancer is bladder cancer.

30. The method of claim 29, wherein the immune checkpoint inhibitor is a PD-L1 inhibitor.

31. The method of claim 30, wherein the PD-L1 inhibitor is selected from the group consisting of atezolizumab, avelumab, and durvalumab.

32. The method of claim 31, wherein the PD-L1 inhibitor is avelumab.

33. The method of claim 29, wherein the chemotherapeutic agent is selected from the group consisting of gemcitabine, carboplatin, cisplatin, and a combination thereof.

34. The method of claim 13, wherein the cancer is triple negative breast cancer.

35. The method of claim 34, wherein the immune checkpoint inhibitor is a PD-1 inhibitor selected from the group consisting of nivolumab, pembrolizumab, and pidilizumab.

36. The method of claim 35, wherein the PD-1 inhibitor is pembrolizumab.

37. The method of claim 34, wherein the chemotherapeutic agent is selected from the group consisting of cyclophosphamide, doxorubicin, paclitaxel, carboplatin, and a combination thereof.

38. A method of treating a human having urothelial carcinoma comprising administering to the human a therapeutic regimen comprising a) an induction phase and b) a maintenance phase, (a) the induction phase comprising:
i) administering to the human an effective amount of a selective CDK4/6 inhibitor of structure:

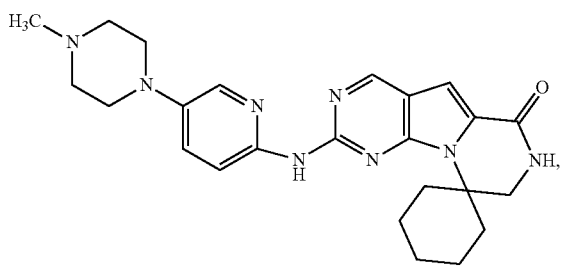 [SMILES: CN1CCN(c2ccc(Nc3ncc4cc5n(c4n3)C3(CCCCC3)CNC5=O)nc2)CC1]

or a pharmaceutically acceptable salt thereof,
ii) administering to the human an effective amount of a chemotherapeutic agent selected from the group consisting of cisplatin, carboplatin gemcitabine, and a combination thereof, wherein, during the induction phase, the CDK4/6 inhibitor is only administered 24 hours or less prior to the administration of the chemotherapeutic agent;

b) the maintenance phase comprising:
i) administering to the human an effective amount of a programmed death ligand 1 (PD-L1) inhibitor, and,
ii) administering to the human an effective amount of the CDK4/6 inhibitor, wherein the maintenance phase is administered following cessation of the induction phase.

39. The method of claim 38, wherein the CDK4/6 inhibitor and chemotherapeutic agent are administered in a 21-day cycle.

40. The method of claim 39, wherein the 21-day cycle is repeated four or more times.

41. The method of claim 38, wherein the PD-L1 inhibitor is selected from the group consisting of atezolizumab, durvalumab, and avelumab.

42. The method of claim 41, wherein the PD-L1 inhibitor is avelumab.

43. A method of treating a human having triple negative breast cancer comprising administering to the human a therapeutic regimen comprising:

i) administering to the human an effective amount of a selective CDK4/6 inhibitor of structure:

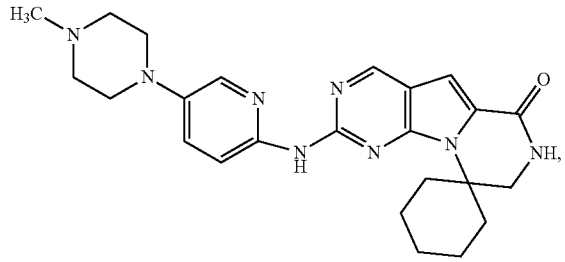 [SMILES: CN1CCN(c2ccc(Nc3ncc4cc5n(c4n3)C3(CCCCC3)CNC5=O)nc2)CC1]

or a pharmaceutically acceptable salt thereof,
ii) administering to the human an effective amount of a chemotherapeutic agent selected from the group consisting of doxorubicin, cyclophosphamide, paclitaxel, carboplatin, and a combination thereof,
iii) administering to the human an effective amount of pembrolizumab, wherein the CDK4/6 inhibitor is administered 24 hours or less prior to the administration of the chemotherapeutic agent.

44. The method of claim 13, wherein the cancer is non-small cell lung cancer.

45. The method of claim 44, wherein the immune checkpoint inhibitor is a PD-1 inhibitor selected from the group consisting of nivolumab, pembrolizumab, and pidilizumab.

46. The method of claim 45, wherein the PD-1 inhibitor is pembrolizumab.

47. A method of treating a human having metastatic non-squamous non-small cell lung cancer comprising administering to the human a therapeutic regimen comprising a) an induction phase comprising a 21-day cycle and b) a maintenance phase comprising a 21-day cycle, a) the induction phase comprising:
i) administering to the human an effective amount of a selective CDK4/6 inhibitor of structure:

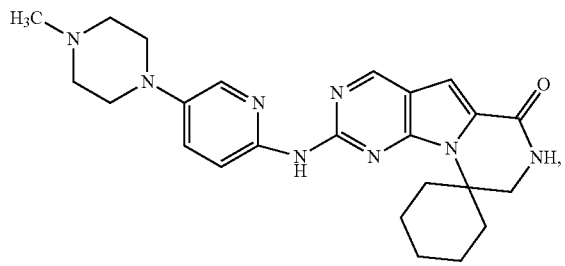 [SMILES: CN1CCN(c2ccc(Nc3ncc4cc5n(c4n3)C3(CCCCC3)CNC5=O)nc2)CC1]

or a pharmaceutically acceptable salt thereof, on day 1 of the 21-day cycle,
ii) administering to the human an effective amount of carboplatin on day 1 of the 21-day cycle,
iii) administering to the human an effective amount of pemetrexed on day 1 of the 21-day cycle, and
iv) administering to the human an effective amount of pembrolizumab on day 1 of the 21-day cycle;

wherein, during the induction phase, the CDK4/6 inhibitor is only administered 24 hours or less prior to the administration of carboplatin and/or pemetrexed;

b) the maintenance phase comprising:
i) administering to the human an effective amount of pembrolizumab on day 1 of the 21-day cycle, wherein the maintenance phase is administered following the cessation of the induction phase.

48. The method of claim 1, wherein, during the induction phase, the CDK4/6 inhibitor is only adminsitered about 4 hours or less prior to the administration of the chemotherapeutic agent.

49. The method of claim 38, wherien, during the induction phase, the CDK4/6 inhibitor is only administered about 4 hours or less prior to the administration of the chemotherapeutic agent.

50. The method of claim 43, wherein, during the induction phase, the CDK4/6 inhibitor is administered about 4 or less prior to the administration of the chemotherapeutic agent.

51. The method of claim 47, wherein, during the induction phase, the CDK4/6 inhibitor is only administered about 4 hours or less prior to the administration of carboplatin and/or pemetrexed.

* * * * *